(12) United States Patent
Wilt et al.

(10) Patent No.: US 9,518,958 B2
(45) Date of Patent: Dec. 13, 2016

(54) SYSTEM, METHOD, AND APPARATUS FOR DETECTING AIR IN A FLUID LINE USING ACTIVE RECTIFICATION

(71) Applicant: DEKA Products Limited Partnership, Manchester, NH (US)

(72) Inventors: Michael J. Wilt, Windham, NH (US); Jason M. Sachs, Chandler, AZ (US)

(73) Assignee: DEKA Products Limited Partnership, Manchester, NH (US)

( * ) Notice: Subject to any disclaimer, the term of this patent is extended or adjusted under 35 U.S.C. 154(b) by 406 days.

(21) Appl. No.: 14/101,848

(22) Filed: Dec. 10, 2013

(65) Prior Publication Data
US 2014/0165703 A1   Jun. 19, 2014

Related U.S. Application Data

(60) Provisional application No. 61/738,447, filed on Dec. 18, 2012.

(51) Int. Cl.
| | | |
|---|---|---|
| *G01N 29/02* | (2006.01) | |
| *G01N 29/032* | (2006.01) | |
| *G01N 29/44* | (2006.01) | |

(52) U.S. Cl.
CPC ............ *G01N 29/02* (2013.01); *G01N 29/032* (2013.01); *G01N 29/4427* (2013.01); *G01N 2291/02433* (2013.01)

(58) Field of Classification Search
CPC .................. G01N 29/02; G01N 29/032; G01N 2291/02433

USPC .............................................. 73/19.03, 24.06
See application file for complete search history.

(56) References Cited

U.S. PATENT DOCUMENTS

| | | | | |
|---|---|---|---|---|
| 4,068,521 A | * | 1/1978 | Cosentino | A61B 8/481 600/437 |
| 5,177,993 A | * | 1/1993 | Beckman | A61M 5/365 128/DIG. 13 |
| 5,392,638 A | * | 2/1995 | Kawahara | A61M 5/365 73/61.49 |
| 5,394,732 A | * | 3/1995 | Johnson | A61M 1/3626 73/19.03 |
| 5,658,133 A | * | 8/1997 | Anderson | A61M 5/172 417/479 |
| 6,142,008 A | * | 11/2000 | Cole | A61M 5/365 128/DIG. 13 |

(Continued)

FOREIGN PATENT DOCUMENTS

| | | | |
|---|---|---|---|
| JP | 2003-57177 | * | 2/2003 |
| WO | WO2013095459 A9 | | 6/2013 |

(Continued)

*Primary Examiner* — Daniel S Larkin
(74) *Attorney, Agent, or Firm* — James D. Wyninegar, Jr.

(57) ABSTRACT

A circuit for detecting air, a related system, and a related method are provided. The circuit for detecting air includes a receiver connection and an air-detection circuit. The receiver connection is configured to provide a receiver signal. The air-detection circuit is in operative communication with the receiver connection to process the receiver signal to generate a processed signal corresponding to detected air. The air-detection circuit includes one or more active-rectifying elements configured to actively rectify the receiver signal to provide the processed signal.

28 Claims, 40 Drawing Sheets

(56) References Cited

U.S. PATENT DOCUMENTS

| | | | |
|---|---|---|---|
| 6,282,949 B1* | 9/2001 | Axelsson | G01N 29/032 73/19.03 |
| 8,225,639 B2* | 7/2012 | Riley | A61M 5/365 73/19.03 |
| D728,779 S | 5/2015 | Sabin et al. | |
| D735,319 S | 7/2015 | Sabin et al. | |
| D736,370 S | 8/2015 | Sabin et al. | |
| 9,151,646 B2 | 10/2015 | Kamen et al. | |
| D745,661 S | 12/2015 | Collins et al. | |
| D749,206 S | 2/2016 | Johnson et al. | |
| D751,689 S | 3/2016 | Peret et al. | |
| D751,690 S | 3/2016 | Peret et al. | |
| D752,209 S | 3/2016 | Peret et al. | |
| 9,295,778 B2 | 3/2016 | Kamen et al. | |
| D754,065 S | 4/2016 | Gray et al. | |
| D756,386 S | 5/2016 | Kendler et al. | |
| D760,288 S | 6/2016 | Kendler et al. | |
| D760,289 S | 6/2016 | Kendler et al. | |
| 9,364,394 B2 | 6/2016 | Demers et al. | |
| 9,372,486 B2 | 6/2016 | Peret et al. | |
| D760,782 S | 7/2016 | Kendler et al. | |
| D760,888 S | 7/2016 | Gill et al. | |
| 9,400,873 B2 | 7/2016 | Kamen et al. | |
| 9,435,455 B2 | 9/2016 | Peret et al. | |
| 2008/0184784 A1* | 8/2008 | Dam | G01N 29/032 73/61.75 |
| 2009/0078047 A1* | 3/2009 | Dam | A61M 1/3626 73/606 |
| 2011/0313789 A1 | 12/2011 | Kamen et al. | |
| 2012/0185267 A1 | 7/2012 | Kamen et al. | |
| 2013/0091953 A1* | 4/2013 | Brown | A61M 5/365 73/642 |
| 2013/0177455 A1 | 7/2013 | Kamen et al. | |
| 2013/0182381 A1 | 7/2013 | Gray et al. | |
| 2013/0184676 A1 | 7/2013 | Kamen et al. | |
| 2013/0188040 A1 | 7/2013 | Kamen et al. | |
| 2013/0191513 A1 | 7/2013 | Kamen et al. | |
| 2013/0197693 A1 | 8/2013 | Kamen et al. | |
| 2013/0204188 A1 | 8/2013 | Kamen et al. | |
| 2013/0272773 A1 | 10/2013 | Kamen et al. | |
| 2013/0281965 A1 | 10/2013 | Kamen et al. | |
| 2013/0297330 A1 | 11/2013 | Kamen et al. | |
| 2013/0310990 A1 | 11/2013 | Peret et al. | |
| 2013/0317753 A1 | 11/2013 | Kamen et al. | |
| 2013/0317837 A1 | 11/2013 | Ballantyne et al. | |
| 2013/0336814 A1 | 12/2013 | Kamen et al. | |
| 2013/0339049 A1 | 12/2013 | Blumberg, Jr. | |
| 2013/0346108 A1 | 12/2013 | Kamen | |
| 2014/0180711 A1 | 6/2014 | Kamen et al. | |
| 2014/0188076 A1 | 7/2014 | Kamen et al. | |
| 2014/0188516 A1 | 7/2014 | Kamen et al. | |
| 2014/0195639 A1 | 7/2014 | Kamen et al. | |
| 2014/0227021 A1 | 8/2014 | Kamen et al. | |
| 2014/0318639 A1 | 10/2014 | Peret et al. | |
| 2014/0343492 A1 | 11/2014 | Kamen | |
| 2015/0002667 A1 | 1/2015 | Peret et al. | |
| 2015/0002668 A1 | 1/2015 | Peret et al. | |
| 2015/0002677 A1 | 1/2015 | Peret et al. | |
| 2015/0033823 A1 | 2/2015 | Blumberg, Jr. | |
| 2015/0154364 A1 | 6/2015 | Biasi et al. | |
| 2015/0157791 A1 | 6/2015 | Desch et al. | |
| 2015/0238228 A1 | 8/2015 | Langenfeld et al. | |
| 2015/0257974 A1 | 9/2015 | Demers et al. | |
| 2015/0314083 A1 | 11/2015 | Blumberg, Jr. et al. | |
| 2015/0332009 A1 | 11/2015 | Kane et al. | |
| 2016/0055397 A1 | 2/2016 | Peret et al. | |
| 2016/0055649 A1 | 2/2016 | Peret et al. | |
| 2016/0061641 A1 | 3/2016 | Peret et al. | |
| 2016/0063353 A1 | 3/2016 | Peret et al. | |
| 2016/0073063 A1 | 3/2016 | Peret et al. | |
| 2016/0084434 A1 | 3/2016 | Janway et al. | |
| 2016/0097382 A1 | 4/2016 | Kamen et al. | |
| 2016/0131272 A1 | 5/2016 | Yoo | |
| 2016/0158437 A1 | 6/2016 | Biasi et al. | |
| 2016/0179086 A1 | 6/2016 | Peret et al. | |
| 2016/0184510 A1 | 6/2016 | Kamen et al. | |

FOREIGN PATENT DOCUMENTS

| | | |
|---|---|---|
| WO | WO2013096713 A2 | 6/2013 |
| WO | WO2013096718 A2 | 6/2013 |
| WO | WO2013096722 A2 | 6/2013 |
| WO | WO2013096909 A2 | 6/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 9/2014 |
| WO | WO2015017275 A1 | 2/2015 |

* cited by examiner

150 CONT.

SYSTEM, METHOD, AND APPARATUS FOR DETECTING AIR IN A FLUID LINE USING ACTIVE RECTIFICATION

CROSS-REFERENCE TO RELATED APPLICATION

The present application is a Non-Provisional application which claims the benefit of U.S. Provisional Patent Application Ser. No. 61/738,447, filed Dec. 18, 2012 and entitled System, Method, and Apparatus for Detecting Air in a Fluid Line Using Active Rectification, which is hereby incorporated herein by reference in its entirety.

BACKGROUND

Relevant Field

The present disclosure relates to detecting (e.g., for estimating, tracking, or categorizing) gas (e.g., air bubbles) in a fluid line. More particularly, the present disclosure relates to a system, method, and apparatus for detecting air in a fluid line using active rectification. For example, the present disclosure relates to a system, method, and/or an apparatus for detecting air bubbles in a fluid line used in various medical applications, such as intravenous infusion therapy, dialysis, transfusion therapy, peritoneal infusion therapy, bolus delivery, enteral nutrition therapy, parenteral nutrition therapy, hemoperfusion therapy, fluid resuscitation therapy, or insulin delivery, among others.

Description of Related Art

In many medical settings, one common mode of medical treatment involves delivering fluids into a patient. The need may arise to rapidly infuse therapeutic fluid into the patient, accurately infuse the fluid into the patient, and/or slowly infuse the fluid into the patient. Occasionally, air bubbles may form within the fluid line coupled to the patient which may then deliver the bubbles to the patient's tissue with the therapeutic fluid.

Too much air delivered to a patient may be detrimental for a patient. For example, too much total air delivered to a patient during a treatment or too much air delivered to a patient during a timeframe (e.g., the last 10 minutes) may have adverse effects on the patient. Furthermore, air bubbles within the fluid line may offset the amount of therapeutic fluid delivered to the patient. Patient outcomes may be improved to account for any displaced therapeutic fluid by increasing the amount of fluid infused to ensure that the desired amount of therapeutic fluid is delivered to the patient.

Delivery of fluid into the patient may be facilitated by use of a gravity-fed line (or tube) inserted into the patient. Typically, a fluid reservoir (e.g., an IV bag) is hung on a pole and is connected to the fluid tube. The fluid tube is sometimes coupled to a drip chamber for trapping air and estimating fluid flow. Below the fluid tube may be a manually actuated valve used to adjust the flow of fluid. For example, by counting the number of drops formed in the drip chamber within a certain amount of time, a caregiver can calculate the rate of fluid that flows through the drip chamber and adjust the valve (if needed) to achieve a desired flow rate.

Certain treatments require that the fluid delivery system strictly adhere to the flow rate set by the caregiver. Typically, such applications use an infusion pump, but such pumps may not be used in all situations or environments. Air detection may be used by a gravity fed infusion treatment or an infusion pump assisted infusion treatment, among other medical applications.

SUMMARY

In one embodiment of the present disclosure, a system for detecting air (e.g., a bubble) is provided. The system may be part of an infusion pump or may be part of a dialysis apparatus. The system includes a transmitter, a receiver, and an air-detection circuit. The transmitter is configured to transduce a driver signal to ultrasonic vibrations. The receiver is configured to receive the ultrasonic vibrations and transduce the ultrasonic vibrations to provide a receiver signal.

The air-detection circuit is in operative communication with the receiver to process the receiver signal to generate a processed signal corresponding to detected air. In an embodiment, the air-detection circuit may include a rectification circuit, such as one having one or more active rectifiers. For example, the air-detection circuit may include one or more active-rectifying elements each configured to actively rectify the receiver signal to provide the processed signal. The receiver signal and the processed signal may be digital signals embodied in a digital circuit or may be analog signals.

The transmitter and receiver are configured to pass the ultrasonic vibrations through a tube such that the processed signal corresponds to detected air within the tube. The tube may be a medical tube, an intravenous fluid tube, and/or may carry blood.

The air-detection circuit may compare the processed signal to a predetermined threshold to determine if a bubble exists within the tube In some embodiments, the system may include an amplifier. The amplifier may amplify the receiver signal or the processed signal.

In yet another embodiment, the system includes a sample-and-hold circuit configured to sample the processed signal to hold the processed signal for at least a predetermined amount of time.

In yet another embodiment, the transmitter and receiver are configured to pass the ultrasonic vibrations through a tube such that the processed signal corresponds to detected air within the tube. The air-detection circuit may be configured to calculate a total amount of air passing through the tube utilizing a flow rate of fluid through the tube and the processed signal.

In yet another embodiment, the system includes first and second conductive paths, first and second switches, a first amplifier, and a first filter. The first conductive path provides a first polarity of the receiver signal from the receiver. The second conductive path provides a second polarity of the receiver signal from the receiver. The first switch is electrically coupled to the first and second conductive paths. The first switch is configured to switch a first switch output to between the first and second polarities of the receiver signal. The first switch is an active-rectifying element. The second switch is electrically coupled to the first and second conductive paths. The first switch is configured to switch a first switch output to between the first and second polarities of the receiver signal. The first amplifier has a positive input and a negative input. The positive input is coupled to the first switch output and the negative input is coupled to the second switch output. The first amplifier provides a first amplifier output in accordance with the positive and negative inputs.

The first filter is electrically coupled to the first amplifier output of the first amplifier to provide a first filter output.

One or more of the receiver signal, the processed signal, the first amplifier output, and a first filter output is a digital signal embodied in a digital circuit and/or an analog signal.

The first filter may be an integrator. The integrator may be reset after a predetermined period of integration time. In another embodiment, the first filter may be a low-pass filter.

The first and second switches may be electronically controlled. The first and second switches may be configured to receive a switching signal. The switching signal and the first and second switches may be configured to switch a polarity of the electrical coupling between the first amplifier and the receiver in accordance with the switching signal.

In yet another embodiment of the present disclosure, the first and second switches are configured to receive a switching signal. The first and second switches switch such that the first switch output is coupled to the first polarity of the receiver signal about when the second switch output is coupled to the second polarity. The first and second switches switch such that the first switch output is coupled to the second polarity of the receiver signal about when the second switch output is coupled to the first polarity. The first and second switches switch in response to the switching signal. The switching signal may have a frequency that is at least substantially the same as (or equal to) a frequency of the ultrasonic vibrations. The switching signal may have a frequency equal to a frequency of the driver signal. The switching signal has a phase angle relative to the driver signal, which may be zero degrees or 90 degrees.

In yet another embodiment, the system further includes third and fourth switches, a second amplifier, and a second filter. The third switch is electrically coupled to the first and second conductive paths. The third switch is configured to switch a third switch output to between the first and second polarities of the receiver signal. The fourth switch is electrically coupled to the first and second conductive paths. The fourth switch is configured to switch a fourth switch output to between the first and second polarities of the receiver signal. The second amplifier has a positive input and a negative input. The positive input of the second amplifier is coupled to the third switch output and the negative input of the second amplifier is coupled to the fourth switch output. The second amplifier provides a second amplifier output in accordance with the positive and negative inputs. The second filter is coupled to the second amplifier to provide a second filter output. The second filter may be another integrator or a low-pass filter. The second filter (e.g., another integrator) may be reset after a predetermined period of integration time. The third and/or fourth switches may be electronically controlled.

The first and second switches may be configured to receive a first switching signal. The first switching signal and the first and second switches are configured to switch a polarity of the electrical coupling between the first amplifier and the receiver in accordance with the first switching signal. The third and fourth switches may be configured to receive a second switching signal. The second switching signal may have a phase angle of 90 degrees relative to the first switching signal. The second switching signal and the third and fourth switches are configured to switch a polarity of the electrical coupling between the second amplifier and the receiver in accordance with the second switching signal. The first switching signal and the second switching signal is a digital signal embodied in a digital circuit and/or is an analog signal.

The processed signal may be a square root of: a squared first filter output summed with a squared second filter output. A processor may determine that air exists in a fluid tube when the processed signal is below a predetermined threshold. The processor may estimate a bubble volume using the flow rate of fluid within the tube and a period of time the processed signal is below the predetermined threshold. The processor may be one of a microprocessor, a microcontroller, a CPLD, and a FPGA, which may generate the first and second switching signals.

In yet another embodiment of the present disclosure, the first and second switches are configured to receive a first switching signal. The first and second switches switch in response to the first switching signal. The first and second switches switch such that the first switch output is coupled to the first polarity of the receiver signal about when the second switch output is coupled to the second polarity. The first and second switches switch such that the first switch output is coupled to the second polarity of the receiver signal about when the second switch output is coupled to the first polarity. The third and fourth switches are configured to receive a second switching signal. The third and fourth switches switch in response to the second switching signal. The third and fourth switches switch such that the third switch output is coupled to the first polarity of the receiver signal about when the fourth switch output is coupled to the second polarity. Finally, the third and fourth switches switch such that the third switch output is coupled to the second polarity of the receiver signal about when the fourth switch output is coupled to the first polarity. The first and second switching signals may each have a frequency at least substantially the same as a frequency of the ultrasonic vibrations. The first and second switching signals may each have a frequency at least substantially the same as a frequency of the driver signal. The first switching signal may have a phase angle of about 90 degrees relative to the second switching signal. The first switching signal may have a phase angle of 90 degrees relative to the second switching signal.

The air-detection circuit may include one or more amplifiers and the processed signal is used to mitigate at least one offset error of the amplifier using the processed signal.

In some embodiments, a temporal window of the processed signal in which the receiver is not receiving the ultrasonic vibrations is used to mitigate at least one offset error of the amplifier.

In yet another embodiment, the system further wherein the driver signal is configured to be generated in predetermined bursts having a predetermined burst frequency.

In yet another embodiment of the present disclosure, the one or more active-rectifying elements may be one or more single-pole, double-throw switches. The single-pole, double-throw switches may be solid-state switches.

In yet additional embodiments, the one or more active-rectifying elements may be one or more single-pole, single-throw switches, which may be solid-state switches.

In yet an additional embodiment of the present disclosure, the system includes first and second single pole, single throw switches. The first single pole, single throw switch may be one of the active-rectifying elements and is configured to provide electrical communication between the receiver signal and a first switch output in accordance with a first switching signal. The second single pole, single throw switch may be configured to provide electrical communication between receiver signal and a second switch output in accordance with an inverted signal of the switching signal. One or both of the first switching signal and the inverted signal of the switching signal may be digital signals embodied in a digital circuit and/or analog signals.

The system may further includes a first amplifier configured to amplify the receiver signal prior to electrical coupling with the first single pole, single throw switch. The system further may also include a second amplifier configured to amplify the receiver signal prior to electrical coupling with the second single pole, single throw switch.

In yet another embodiment, the system includes third and fourth single pole, single throw switches. The third single pole, single throw switch is configured to provide electrical communication between an inversion of the receiver signal and a third switch output in accordance with a second switching signal. The fourth single pole, single throw switch is configured to provide electrical communication between the inversion of the receiver signal and a fourth switch output in accordance with an inverted signal of the switching signal. The first and second switching signals have a quadrature phase relationship.

An amplifier may be used and is configured to amplify the inversion of the receiver signal prior to electrical communication with one of the third and fourth single, pole, single throw switches.

The system may further include a first integrator such that the first switch output and a second switch output are in electrical communication with the first integrator to integrate a signal therefrom to provide a first integrator output. The first integrator may be reset after a first predetermined period of time. The system may include a first sample-and-hold circuit configured to operatively sample and hold the first integrator output.

The system may yet also include a second integrator such that the third switch output and the fourth switch output are in electrical communication with the second integrator to integrate a signal therefrom to provide a second integrator output. The second integrator may be reset after a second predetermined period of time. The system may include a second sample-and-hold circuit configured to operatively sample and hold the second integrator output.

The first and second switching signals may be synchronized to the driver signal.

The processed signal is a square root of: a squared first integrator output summed with a squared second integrator output. The system may further include a processor configured to determine whether air exists when the processed signal is below a predetermined threshold.

The first and second integrators may integrate for a predetermined number of cycles of the driver cycles a predetermined period of time after the driver signal is driving the transmitter.

The first integrator can integrate for a predetermined number of cycles of the driver signal for a predetermined period of time after the driver signal drives the transmitter such that the ultrasonic vibrations have passed the receiver. The first integrator output is used to adjust an offset of the first integrator.

The second integrator may integrate for a predetermined period to capture all of the ultrasonic vibrations passing the receiver. The second integrator output may be used to adjust an offset of the first second.

The system may further include a first sample-and-hold circuit to hold a voltage of the first integrator output for the processor to determine the processed signal, a first diagnostic sample-and-hole circuit to hold the voltage of the first integrator output to adjust an offset of the first integrator, a second sample-and-hold circuit to hold a voltage of the second integrator output for the processor to determine the processed signal, and a second diagnostic sample-and-hole circuit to hold the voltage of the second integrator output to adjust an offset of the second integrator.

The first and second switching signals may be generated using at least one of a processor, a FPGA, a CPLD, and an oscillator. The processed signal may a vector defined by the first integrator output and the second integrator output and a processor may perform an integrity check by determining if a phase angle of the processed signal is within a predetermined range.

In one embodiment of the present disclosure, a method of detecting air is provided. The method for detecting air may include transmitting ultrasonic energy, receiving the ultrasonic energy, transducing the received ultrasonic energy into a receiver signal, and actively rectifying the receiver signal to provide a processed signal. The method may also include determining whether the processed signal is less that a predetermined threshold.

The method may include the transmitting act is performed by an ultrasonic transducer. The ultrasonic transducer may be a piezoelectric ceramic. In another embodiment the transducing act may be performed by an ultrasonic transducer. The ultrasonic transducer may be a piezoelectric ceramic.

In yet some additional embodiments, the act of actively rectifying the receiver signal to provide the processed signal may be synchronously rectifying the receiver signal to provide the processed signal. In some embodiments, the act of transmitting the ultrasonic energy may include transmitting the ultrasonic energy through a tube.

In yet another embodiment of the method, the act of actively rectifying the receiver signal to provide the processed signal includes: inverting the receiver signal to provide an inverted receiver signal, switching between the receiver signal and the inverted receiver signal in accordance with a first switching signal to provide a first switch output, integrating the first switch output to provide a first integrated output, switching between the receiver signal and the inverted receiver signal in accordance with a second switching signal to provide a second switch output, integrating the second switch output to provide a second integrated output, and calculating a magnitude using the first and second integrated outputs, wherein the magnitude defines the processed signal.

The method may further include determining that air exists within a tube if the magnitude is less that the predetermined threshold.

In yet some additional embodiments of the method, the first and second switching signals may each have a frequency equal to a dominant frequency of the ultrasonic energy. The first and second switching signal may be ninety degrees out of phase relative to each other. The first and second switching signal may be about ninety degrees out of phase relative to each other.

In some embodiments, at least one of the receiver signal, the inverted receiver signal, the first switch output, the second switch output, the first integrate output, and the second integrated output may be amplified by an amplifier.

In yet other embodiments, the act of switching between the receiver signal and inverted receiver signal in accordance with a first switching signal to provide a first switch output may be configured using at least one of a semiconductor switch, a MOSFET, a single pole, single throw switch, a single pole double throw switch, a single pole changeover switch, a double pole double throw switch, a four-way switch, a transistor, a BJT transistor, and a relay switch.

In some embodiments, the method may be at least partially implemented by a circuit on an infusion pump configured to detect air in an intravenous tube.

In some embodiments, the act of actively rectifying the receiver signal to provide the processed signal may include: activating a first switching network configured to switch between the receiver signal and an inverted receiver signal to provide a first switching network signal, switching between the receiver signal and the inverted receiver signal in accordance with a first switching signal to provide the first switching network signal, integrating the first switching network signal to provide a first integrated output, activating a second switching network configured to switch between the receiver signal and an inverted receiver signal to provide a second switching network signal, switching between the receiver signal and the inverted receiver signal in accordance with a second switching signal to provide the second switching network signal, wherein the second switching signal is about 90 degrees out of phase with the first switching signal, integrating the second switching network signal to provide a second integrated output, and generating a processed signal using the first and second integrated outputs.

In some embodiments, the first switching network may comprise two single pole, double throw switches. The second switching network may comprise two single pole, double throw switches. The processed signal may be a magnitude calculated by using the first and second integrated outputs.

In some embodiments, the act of actively rectifying the receiver signal to provide a processed signal may comprise: amplifying the receiver signal with a positive gain using a first amplifier, amplifying the receiver signal with a negative gain using a second amplifier, switching between outputs of the first and second amplifiers in accordance with a first switching signal to generate a first switch output, filtering the first switch output to provide a first filtered output, switching between the outputs of the first and second amplifiers to generate a second switch output. The second switching signal may be one of equal to or about equal to ninety degrees out of phase with the first switching signal. The second switching output may be filtered to provide a second filtered output. A processed signal may be generated using the first and second filtered outputs.

In another embodiment of this method, the processed signal is a magnitude. The method may further include the acts of: resetting the first filtered output (e.g., resetting the first integrated output); and resetting the second filtered output (e.g., resetting the second integrated output).

In some embodiments, the act of filtering the first switch output to provide the first filtered output is the act of integrating the first switch output to provide a first integrated output, wherein the first filtered output is the first integrated output. Additionally or alternatively, the act of filtering the second switch output to provide the second filtered output may be the act of integrating the second switch output to provide a second integrated output, wherein the second filtered output is the second integrated output.

The act of generating the processed signal using the first and second filtered outputs may be the act of generating the processed signal using the first and second integrated outputs. The act of determining whether the processed signal is less that a predetermined threshold may be the act of determining that air exists within the tube if the magnitude is less that a predetermined threshold.

In some additional embodiments, the method may include: sampling the processed signal and holding the processed signal; determining whether air exists within a tube using the processed signal; determining a total volume of air passing within the tube using the processed signal and a flow rate of fluid within the tube; and/or adjusting at least one offset gain using the processed signal during a period where there is an absence of the ultrasonic energy. The act of sampling the processed signal and holding the processed signal may be performed by a sample-and-hold circuit.

In yet another embodiment of the present disclosure, a system for detecting air includes a transmitter means, a receiver means, and an air-detection means. The transmitter means is a means for transducing a driver signal to ultrasonic vibrations. The receiver means is a means for receiving the ultrasonic vibrations and transducing the ultrasonic vibrations to provide a receiver signal. The air-detection means is a means for actively rectifying the receiver signal to provide a processed signal In yet another embodiment of the present disclosure, a method for detecting air includes the acts of: a transmitting step for transmitting ultrasonic energy; a receiving step for receiving the ultrasonic energy; a transducing step for transducing the received ultrasonic energy into a receiver signal; a rectifying step for actively rectifying the receiver signal to provide a processed signal; and a determining step for determining whether the processed signal is less that a predetermined threshold.

In yet another embodiment of the present disclosure, a circuit includes a receiver connection and an air-detection circuit. The receiver connection is configured to provide a receiver signal. The air-detection circuit is in operative communication with the receiver connection to process the receiver signal to generate a processed signal corresponding to detected air. The air-detection circuit comprising one or more active-rectifying elements configured to actively rectify the receiver signal to provide the processed signal. The air-detection circuit may compare the processed signal to a predetermined threshold to determine if a bubble exists within a tube.

In yet another embodiment of the present disclosure, the circuit also includes first and second conductive paths, first and second switches, a first amplifier, and a first filter. The first conductive path provides a first polarity of the receiver signal from the receiver connection. The second conductive path provides a second polarity of the receiver signal from the receiver connection. The first switch is electrically coupled to the first and second conductive paths. The first switch is configured to switch a first switch output to between the first and second polarities of the receiver signal. The first switch defines the at least one active-rectifying element. The second switch is electrically coupled to the first and second conductive paths. The first switch configured to switch a first switch output to between the first and second polarities of the receiver signal. The first amplifier having a positive input and a negative input. The positive input is coupled to the first switch output and the negative input is coupled to the second switch output, wherein the first amplifier provides a first amplifier output in accordance with the positive and negative inputs. The first filter electrically coupled to the first amplifier output of the first amplifier to provide a first filter output. The first filter may be an integrator.

The first and/or second switches may be configured to receive a switching signal. The first and/or second switches may switch such that the first switch output is coupled to the first polarity of the receiver signal about when the second switch output is coupled to the second polarity. The first and/or second switches may switch such that first switch output is coupled to the second polarity of the receiver signal about when the second switch output is coupled to the first polarity. The first and/or second switches may switch in response to the switching signal.

A third switch may be electrically coupled to the first and second conductive paths. A third switch may be configured to switch a third switch output to between the first and second polarities of the receiver signal. A fourth switch electrically coupled to the first and second conductive paths. A fourth switch may be configured to switch a fourth switch output to between the first and second polarities of the receiver signal. The third and/or fourth switches may be electronically controlled. A second amplifier may have a positive input and a negative input such that the positive input of the second amplifier is coupled to the third switch output and the negative input of the second amplifier is coupled to the fourth switch output. The second amplifier provides a second amplifier output in accordance with the positive and negative inputs. The second filter coupled to the second amplifier to provide a second filter output. The second filter may be another integrator. The another integrator is reset after a predetermined period of integration time. The second filter may be a low-pass filter.

The first and second switches may be configured to receive a first switching signal. The first switching signal and/or the first and second switches may be configured to switch a polarity of the electrical coupling between the first amplifier and the receiver connection in accordance with the first switching signal. The third and fourth switches may be configured to receive a second switching signal. The second switching signal may have a phase angle of 90 degrees relative to the first switching signal. The second switching signal and/or the third and fourth switches may be configured to switch a polarity of the electrical coupling between the second amplifier and the receiver connection in accordance with the second switching signal.

The first and/or second switches may be configured to receive a first switching signal. The first and/or second switches may switch in response to the first switching signal. The first and/or second switches may switch such that the first switch output is coupled to the first polarity of the receiver signal about when the second switch output is coupled to the second polarity. The first and/or second switches may switch such that the first switch output is coupled to the second polarity of the receiver signal about when the second switch output is coupled to the first polarity. The third and/or fourth switches may be configured to receive a second switching signal. The third and/or fourth switches may switch in response to the second switching signal. The third and/or fourth switches may switch such that the third switch output is coupled to the first polarity of the receiver signal about when the fourth switch output is coupled to the second polarity. The third and/or fourth switches may switch such that the third switch output is coupled to the second polarity of the receiver signal about when the fourth switch output is coupled to the first polarity.

In yet some additional embodiments, the circuit includes first and second single pole, single throw switches. The first single pole, single throw switch defines the one or more active-rectifying elements configured to provide electrical communication between the receiver signal and a first switch output in accordance with a first switching signal. The second single pole, single throw switch may be configured to provide electrical communication between receiver signal and a second switch output in accordance with an inverted signal of the switching signal.

A third single pole, single throw switch may be configured to provide electrical communication between an inversion of the receiver signal and a third switch output in accordance with a second switching signal. A fourth single pole, single throw switch may be configured to provide electrical communication between the inversion of the receiver signal and a fourth switch output in accordance with an inverted signal of the switching signal.

A first integrator may be used by the circuit. The first switch output and a second switch output may be in electrical communication with the first integrator to integrate a signal therefrom to provide a first integrator output. Also, a second integrator may be used by the circuit such that the third switch output and the fourth switch output are in electrical communication with the second integrator to integrate a signal therefrom to provide a second integrator output.

The first integrator may integrate for a predetermined number of cycles of the driver cycles for a predetermined period of time after the driver signal is driving a transmitter such that the ultrasonic vibrations have passed a receiver coupled to the receiver connector. The first integrator output may be used to adjust an offset of the first integrator. The second integrator may integrate for the predetermined period to capture all of the ultrasonic vibrations passing a receiver coupled to the receiver connection. The second integrator output is used to adjust an offset of the first second.

This embodiment may also include first and second sample-and-hold circuits, and first and second diagnostic sample-and-hole circuits. The first sample-and-hold circuit may hold a voltage of the first integrator output for the processor to determine the processed signal. The first diagnostic sample-and-hole circuit may hold the voltage of the first integrator output to adjust an offset of the first integrator. The second sample-and-hold circuit may hold a voltage of the second integrator output for the processor to determine the processed signal. The second diagnostic sample-and-hole circuit may hold the voltage of the second integrator output to adjust an offset of the second integrator.

DETAILED DESCRIPTION

Figure 1:
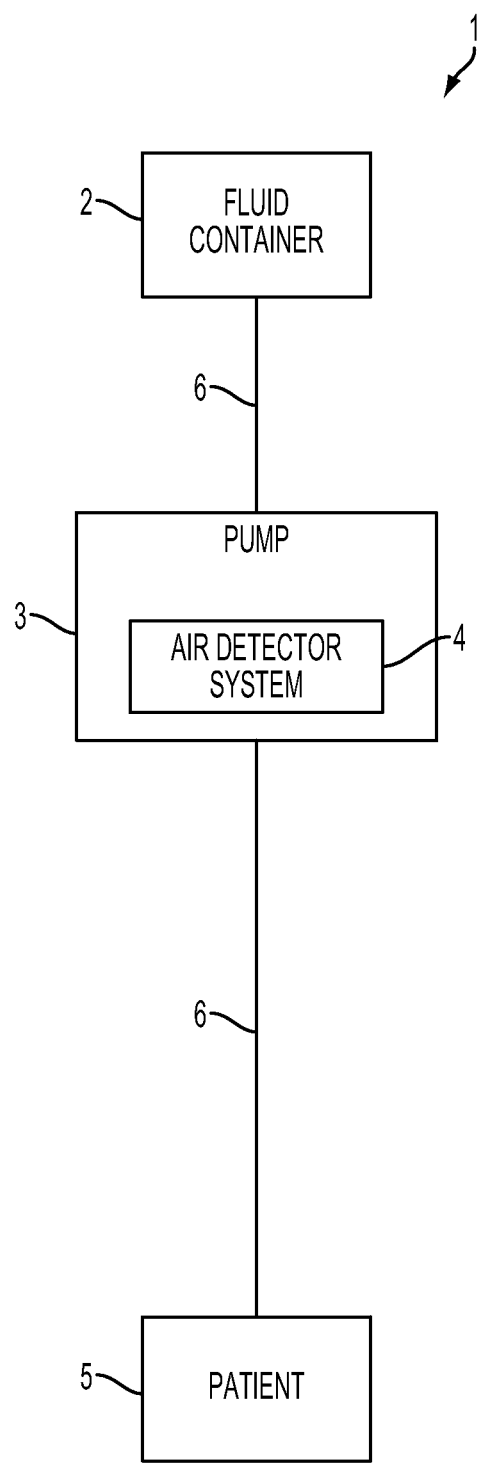
FIG. 1 shows a block diagram of a system for infusing fluid into a patient having an air detector system that detects air a fluid line using active rectification in accordance with an embodiment of the present disclosure.

FIG. 1 shows a block diagram of a system 1 for infusing fluid into a patient 5 having an air detector system 4 that detects air in a fluid line 6 using active rectification in accordance with an embodiment of the present disclosure. The system 1 may be used to treat a patient 5, such as a human or animal (e.g., pets). The system 1 may be part of an intravenous infusion therapy, a dialysis therapy, a transfusion therapy, a peritoneal infusion therapy, a bolus delivery, an enteral nutrition therapy, a parenteral nutrition therapy, a hemoperfusion therapy, a fluid resuscitation therapy, or insulin delivery, among others.

The system 1 includes a fluid container 2 that contains fluid coupled to a fluid line 6. The fluid may flow from the fluid container 2, through the fluid line 6, through a pump 3 and into a patient 5 through a distal portion of the fluid line 6.

The pump 3 includes an air detector system 4 for detecting (e.g., estimating, tracking, or categorizing) air that flows through the pump 3. The pump 3 may be a peristaltic pump, such as a finger-type peristaltic pump. The pump 3 may modify, adjust, or account for air delivered to the patient as determined by the air detector system 4.

The air detector system 4 may use active rectification (described below), such as synchronous rectification. The pump 3 may issue an alarm or alert when: (1) the total amount of air that passes the air detector system 4 during a therapy session exceeds a first predetermined threshold; (2) the amount of air that passes the air detector system 4 during a predetermined period of time exceeds a second predetermined threshold; and/or (3) the amount of air that passes the air detector system 4 during the latest predetermined amount of time exceeds a third predetermined threshold. The first, second, and/or third predetermined thresholds may be the same or may be different from each other. The air detector system 4 may keep track of the air by volume or by weight, and/or may account for the temperature of the air and/or the fluid within the fluid line 6 when detecting the air flowing therethrough.

Figure 2:
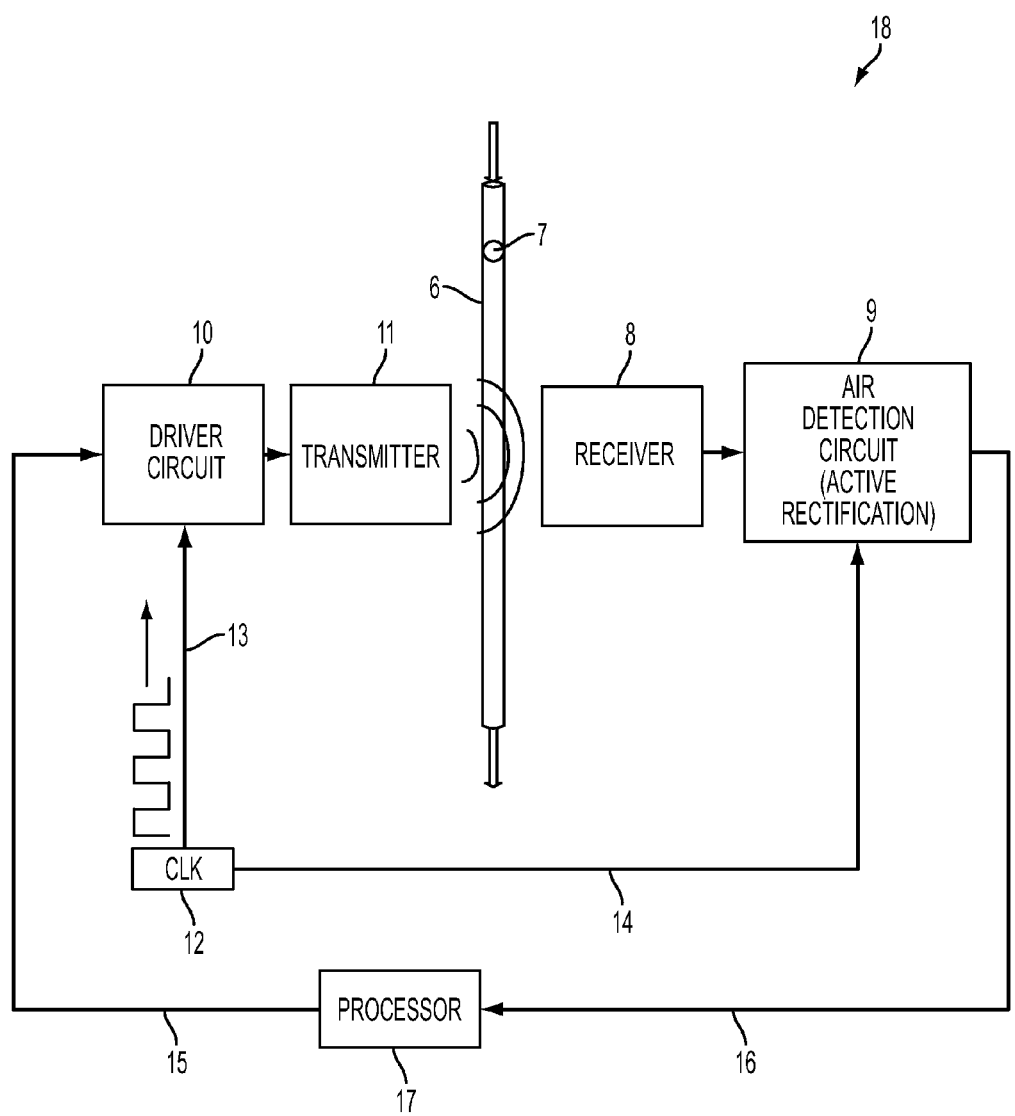
FIG. 2 shows a block diagram of a system for detecting air in a fluid line using active rectification in accordance with an embodiment of the present disclosure.

FIG. 2 shows a block diagram of a system 18 for detecting air (e.g., a bubble 7) in the fluid line 6 using active rectification in accordance with an embodiment of the present disclosure. The system 18 of FIG. 2 may be the air detector system 4 of FIG. 1. The system 18 includes a driver circuit 10, a transmitter 11, a receiver 8, an air detection circuit 9, a clock 12 and a processor 17. The system 18 detects air, such as the air bubble 7, in the fluid line 6. The system 18 uses active rectification, and in some embodiments it uses synchronous rectification, in the air detection circuit 9 to detect air 7 within the fluid line 6, as described below.

The processor 17 signals the driver circuit 10 (via path 15) to drive the transmitter 11 with a drive signal. The transmitter 11 receives the drive signal from the driver circuit 10 to generate ultrasonic energy which is transmitted through the tube 6 to the receiver 8. The receiver 8 receives the ultrasonic energy and transduces the ultrasonic energy into an electric signal. The air detection circuit 9 receives the electric signal for processing therein to provide a processed signal. The processed signal corresponds to air and/or the absence of air within the fluid tube 6.

The air detection circuit 9 provides the processed signal to the processor 17 via path 16. The processor 17 uses the processed signal to detect air within the tube 6. For example, the processor 17 may issue an alarm or an alert when (1) the total amount of air that passes between the transmitter 11 and receiver 8 during a therapy session exceeds a first predetermined threshold; (2) the amount of air that passes between the transmitter 11 and receiver 8 during a predetermined period of time exceeds a second predetermined threshold; and/or (3) the amount of air that passes between the transmitter 11 and receiver 8 during the latest predetermined amount of time exceeds a third predetermined threshold.

The air detection circuit 9 uses active rectification to rectify the electric signal from the receiver 8 to provide the processed signal to the processor 17 via a path 16. In some embodiments of the present disclosure, the air detection circuit 9 and the driver circuit 10 receive a clock signal from a common clock 12 from a path 14 and a path 13, respectively, such that the air detection circuit 9 synchronizes the active rectification with the ultrasonic energy from the transmitter or with the clock 12 to thereby perform synchronous rectification.

The clock 12 generates a reference signal that is sent to the air detection circuit 9 via a path 14 and to the driver circuit 10 via a path 13. The clock 12 may be a semiconductor device, a crystal-based device, a 555-timer configured to generate a cyclical signal, a waveform generator, or any circuit, semiconductor or device that can provide a time reference. The signals sent from the clock 12 may be in the form of a square wave, a pulse-width-modulation signal, a periodic wave, a digital signal, or any other way of communicating information about a time reference. In some embodiments of the present disclosure, the clock 12 is part of or is generated by the processor 17. In yet additional embodiments of the present disclosure, the clock 12 is used as the system clock by the processor 17. Additionally or alternatively, the processor 17 may receive a clock signal from the clock 12 to coordinate its operation with other components that utilizes the clock 12.

The driver circuit 10 is configured to drive the transmitter 11 and receives a clock signal via the path 13. The driver circuit 10 may include appropriate buffers, amplifiers, and power-related circuitry to drive the transmitter 11. The driver circuit 10 may be a single semiconductor device, may be multiple semiconductor devices, may use no semiconductor devices, may comprise one or more passive components, and/or may be a prepackaged driver circuit. The driver circuit 10 may receive electrical power from a power supply (not shown in FIG. 2) to provide sufficient power to drive the transmitter 11. The driver circuit 10 may receive an enable signal via a path 15 from the processor 17. The enable signal from the processor 17 may be in the form of a square wave, a pulse-width-modulation signal, a pulse signal, a digital signal, or any other way of communicating information to the driver circuit. In one specific embodiment of the present disclosure, the driver circuit 10 amplifies the clock signal from the clock 12. The driver circuit 10 may drive the transmitter 11 for a predetermined number of cycles (e.g., 6 cycles).

The transmitter 11 tranduces an electric signal received from the driver circuit 10 to ultrasonic energy. The transmitter 11 may be an ultrasonic transducer, a magnetostrictive transducer, a piezoelectric transducer, a piezoelectric crystal, a piezoelectric ceramic, a capacitive actuation transducer, or other transducer technology.

The transmitter 11 transmits ultrasonic energy through the tube 6. The tube 6 may be a medical tube, such as, for example, an intravenous tube used for intravenous therapy or a tube used in dialysis. The tube 6 may be flexible or rigid and may be held in place by a holder (not shown).

The receiver 8 receives the ultrasonic energy that has, preferably, been propagated through the tube 6. The receiver 8 transduces the ultrasonic energy into a receiver signal that is an electrical signal and provides it for processing by the air detection circuit 9. The receiver 8 may be made of the same material as the transmitter 11 or may utilize the same technology as previously described.

The air detection circuit 9 uses the signal from the receiver 8 to actively rectify the signal therefrom to provide a processed signal. The processed signal may correspond to the magnitude of the ultrasonic energy received by the receiver 8 and/or the magnitude of the receiver signal from the receiver 8. The air detection circuit 9, in some specific embodiments, may use active rectification and thereby may be synchronized with the signal from the clock 12. The air detection circuit 9 may comprise one or more of: (1) a semiconductor device, (2) an analog device, (3) an amplifier, (4) a quadrature signal, (5) a processing device, such as a processor, a microprocessor, a microcontroller, a FPGA, a CPLD, a PAL, a PLD, etc., or (6) any other circuitry. In some embodiments, the processor 17 is part of the air detection circuit 9.

The processor 17 uses the processed signal from the air detection circuit 9 to determine if/when air exists within the tube 6, e.g., the bubble 7. The processor 17 may, for example, determine that air does not exist within the tube 6 between the transmitter 11 and the receiver 8 if the processed signal is above a predetermined threshold. Likewise, the processor 17 may determine that air does exist within the tube 6 if the processed signal is below a predetermined threshold.

The various paths 13, 14, 15, and 16 that couple various components together within the system 18 may be conductive paths (e.g., metal layers in a PCB board), may be analog lines, may be digital lines, may be optical lines, may be electromagnetic lines, or may be another other sufficient communications paths.

Figure 3:
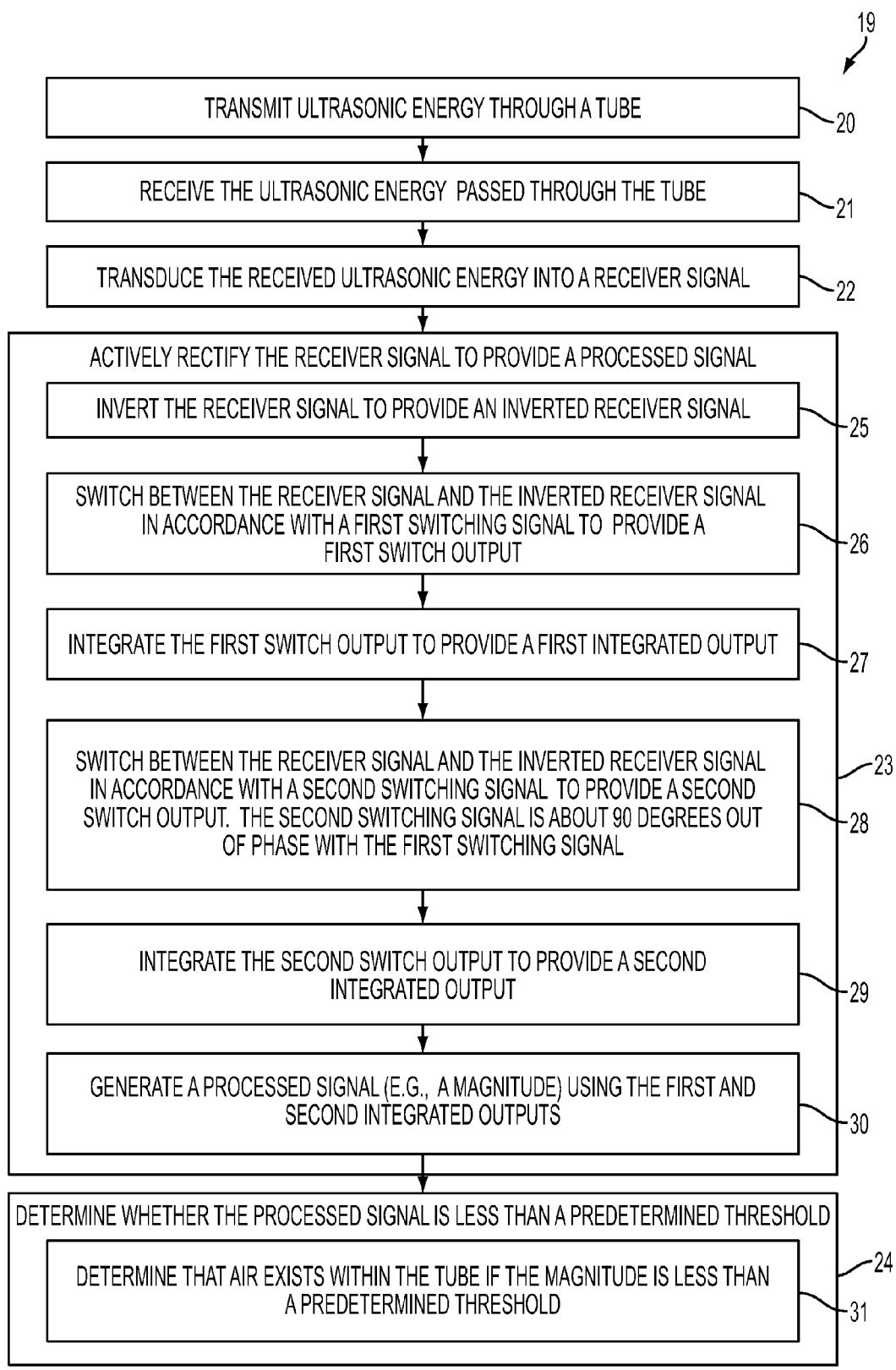
FIG. 3 shows a flow chart diagram of a method for detecting air in a fluid line using active rectification in accordance with an embodiment of the present disclosure.

FIG. 3 shows a flow chart diagram of a method 19 for detecting air in a fluid line using active rectification in accordance with an embodiment of the present disclosure. The method 19 may be implemented using the system 18 of FIG. 2. The method 19 includes acts 20-24, in which act 23 includes acts 25-30 and act 24 includes act 31.

Act 20 transmits ultrasonic energy through a tube. Act 20 may be performed by using, for example, the transmitter 11 of FIG. 2. Act 21 receives the ultrasonic energy passed through the tube. Act 22 transduces the received ultrasonic energy into a receiver signal, e.g., using the receiver 8 of FIG. 2. Act 23 actively rectifies the receiver signal to provide a processed signal. Act 23 may be performed by an air detection circuit, such as the air detection circuit 9 of FIG. 2.

In one specific embodiment of the present disclosure, act 23 includes act 25 through act 30. Acts 25-30 may be performed by an air detection circuit, e.g., the air detection circuit 9 of FIG. 1. Act 25 inverts the receiver signal to provide an inverted receiver signal. Act 26 switches between the receiver signal and the inverted receiver signal in accordance with a first switching signal to provide a first switch output. In some specific embodiments, act 26 may be performed by using one or more switches. Act 27 integrates the first switch output to provide a first integrated output. Act 27 may integrate the first switch output for a predetermined number of cycles (e.g., a predetermined number of cycles of the ultrasonic energy or of the clock, such as the clock 12 of FIG. 2). Act 27 may further include resetting any integrator circuit or algorithm prior to integrating, if appropriate. Act 28 switches between the receiver signal and the inverted receiver signal in accordance with a second switching signal to provide a second switch output. The second switching signal is about 90 degrees out of phase with the first switching signal. Act 28 may be performed by using one or more switches. Act 29 integrates the second switch output to provide a second integrated output. Act 30 generates a processed signal (e.g., a magnitude) using the first and second integrated outputs.

Act 24 determines whether the processed signal is less that a predetermined threshold. Act 24 may include act 31. Act 31 determines that air exists within the tube if the magnitude is less that a predetermined threshold. The magnitude of act 31 is the magnitude of the processed signal.

Figure 4:
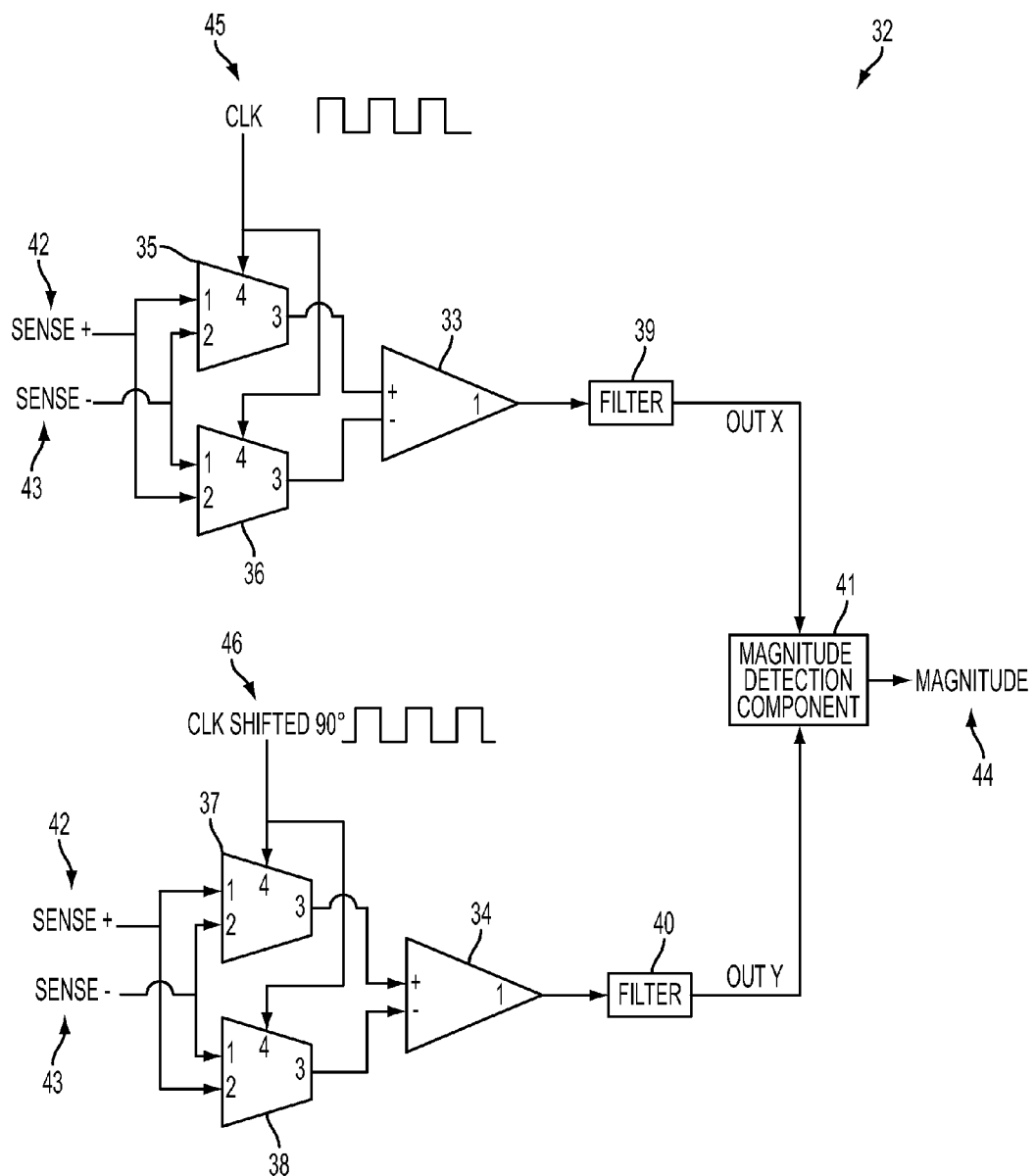
FIG. 4 shows a schematic diagram of a circuit for detecting air in a fluid line using active rectification in accordance with an embodiment of the present disclosure.

FIG. 4 shows a schematic diagram of a circuit 32 for detecting air in a fluid line using active rectification in accordance with an embodiment of the present disclosure. The circuit 32 of FIG. 4 may be the air detection circuit 9 of FIG. 2, in some specific embodiments.

The circuit 32 is coupled to a receiver, such as the receiver 8 of FIG. 2, via positive sense 42 and negative sense 43. The positive sense 42 is coupled to one of the terminals of a receiver, and the negative sense 43 is coupled to another terminal of the receiver. In some embodiments of the present disclosure, one of the positive or negative senses 42 or 43 is coupled to a common reference; for example, the negative sense 43 may be coupled to a ground of the circuit 32.

The positive sense 42 is electrically coupled to a first switch 35 via its terminal 1 and to a second switch 36 via its terminal 2. The negative sense 43 is electrically coupled to the first switch 35 via its terminal 2 and to the second switch 36 via its terminal 1. The switches 35, 36 are single-pull, double throw switches. The switches 35, 36 receive a clock signal 45 (operating as a switching signal) via respective terminals 4. That is, in the arrangement shown in FIG. 4, the switches 35, 36 are electronically controlled by the clock 45. For example, for both of the switches 35, 36, a high value from the clock 45 may cause the switch output at terminal 3 to be electrically coupled to the terminal 1 and a low value from the clock 45 may cause the switch output at terminal three to be electrically coupled to terminal 2. In some embodiments, the terminal selection caused by the clock signal 45 may be reversed. In yet additional embodiments, the transition of the clock 45 can cause the switches 35, 36 to change states (i.e., which input terminal is electrically coupled to the output terminal).

The switch output (terminal 3) of the first switch 35 is electrically coupled to the positive terminal of the first amplifier 33 and the switch output (terminal 3) of the second switch 36 is coupled to the negative terminal of the first amplifier.

The arrangement shown for the first and second switches 35, 36, and the amplifier 33 are such that the polarity of the signal received from the receiver changes depending on the whether the clock 45 is high or low. That is, the clock 45 causes the first amplifier 33 to either amplify the signal from the receiver or its inverted signal in accordance with the clock 45.

In some embodiments of the present disclosure, the amplifier 33 may have a gain of 1, may be a buffer, may have a gain of less than 1, or may have a gain of more than 1. The output of the first amplifier 33 is fed into a first filter 39.

The first filter 39 may be a first integrator that integrates the signal from the amplifier 33 to provide a first integrated output (i.e., a first integrated signal). For example, the first filter 39 may integrate the output from the first amplifier 33 for a predetermined amount of time corresponding to an expected time in which the receiver receives ultrasonic energy; the integrator may be reset for each pulse of ultrasonic energy. In some embodiments, the predetermined amount of time may include periods of time before and after the ultrasonic energy is expected to be received by the receiver to ensure all of the ultrasonic energy is used to generate the first integrated output. The ultrasonic energy may be generated in a pulse of energy having a plurality of periodic waveforms, such as, for example, 6 cycles of a sine wave. The first filter 39 provides the first integrated output (labeled as Out X) that is fed into the magnitude detection component 41.

Also coupled to the positive sense 42 and the negative sense 43 are a third switch 37 and a fourth switch 38. The outputs of the third and fourth switches 37, 38 are fed into a second amplifier 34. The third and fourth switches 37, 38 and the second amplifier 34 are arranged such that the polarity of the signal from the receiver (received as the positive sense 42 and the negative sense 43) is switched in accordance with a quadrature clock 46. That is, the clock 46 has the same frequency as the clock 45 but is out of phase by 90 degrees relative to the clock 45.

The clock 45 and the quadrature clock 46 may be generated from the clock 12 of FIG. 2, or may be generated by the clock 12 and sent via a path 14 to the circuit 32. In yet additional embodiments of the present disclosure, the clock 45 may be generated by the clock 12 of FIG. 2 which is used to generate the quadrature clock 46, e.g., using a phase-locked loop. In yet additional embodiments, a logic device, such as a CPLD or a FPGA, is used to generate the clock 45 and quadrature clock 46 which may also generate a clock used in generating the driver signal to the transmitter 11 (see FIG. 2).

The output of the second amplifier 34 is fed into a second filter 40, which may be a second integrator. The second filter 40 provides a second integrated output (labeled as output Y) which is fed into the magnitude detection component 41.

The magnitude detection component 41 calculates the magnitude of the signal received by the receiver via the positive sense 42 and the negative sense 43. The out X signal may define an x-component of a vector and the out Y signal may define a y-component of the same vector. Therefore, the magnitude 44 is calculated using by taking the square root of the squared output from the first filter 39 summed with the squared output from the second filter 40. That is, the magnitude 44 is calculated using Formula (1) as follows:

$$\text{Magnitude} = \sqrt{Outx^2 + Outy^2} \qquad (1).$$

In other embodiments of the present disclosure, a reference value may be used to ensure that any signal swings are within a predetermined range. For example, one or more op-amps that are used within a circuit may output a signal between ground and the power supply. A reference voltage may be used to offset the output of the op-amps such that the output signal does not reach a limit of the op-amp's voltage range (e.g., a rail of the op-amp). In this embodiment, Formula (1) above is modified to include the reference voltage as illustrated in Formula (2) as follows:

$$\text{Magnitude} = \sqrt{(Outx - referenceVoltage_1)^2 + (Outy - referenceVoltage_2)^2} . \qquad (2)$$

In some embodiments, the referenceVoltage$_1$ may be equal to the referenceVoltage$_2$.

In some embodiments of the present disclosure, outputs of any op-amps used may produce an offset error, which may be accounted for. In some embodiments of the present disclosure, these errors are accounted for in accordance with Formula (3) as follows:

$$\text{Magnitude} = \sqrt{\begin{array}{l}(Outx - referenceVoltage_1 - offsetVoltage_1)^2 + \\ (Outy - referenceVoltage_2 - offsetVoltage_2)^2\end{array}} . \qquad (3)$$

In some embodiments, the referenceVoltage$_1$ may be equal to the referenceVoltage$_2$. In yet some additional embodiments, the offsetVoltage$_1$ may be equal to the offsetVoltage$_2$. In some embodiments of the present disclosure, the reference voltage is modified to account for any error offsets such that the reference voltage is a compensating reference voltage. That is, the compensating reference voltage compensates for offset errors. Therefore, Equation (2) may be used because the reference voltages are modified prior to being used in the circuit.

The magnitude 44 corresponds to the magnitude of the ultrasonic energy received by the receiver that is coupled to the circuit 32 via the positive sense 42 and the negative sense 43.

Figure 5:
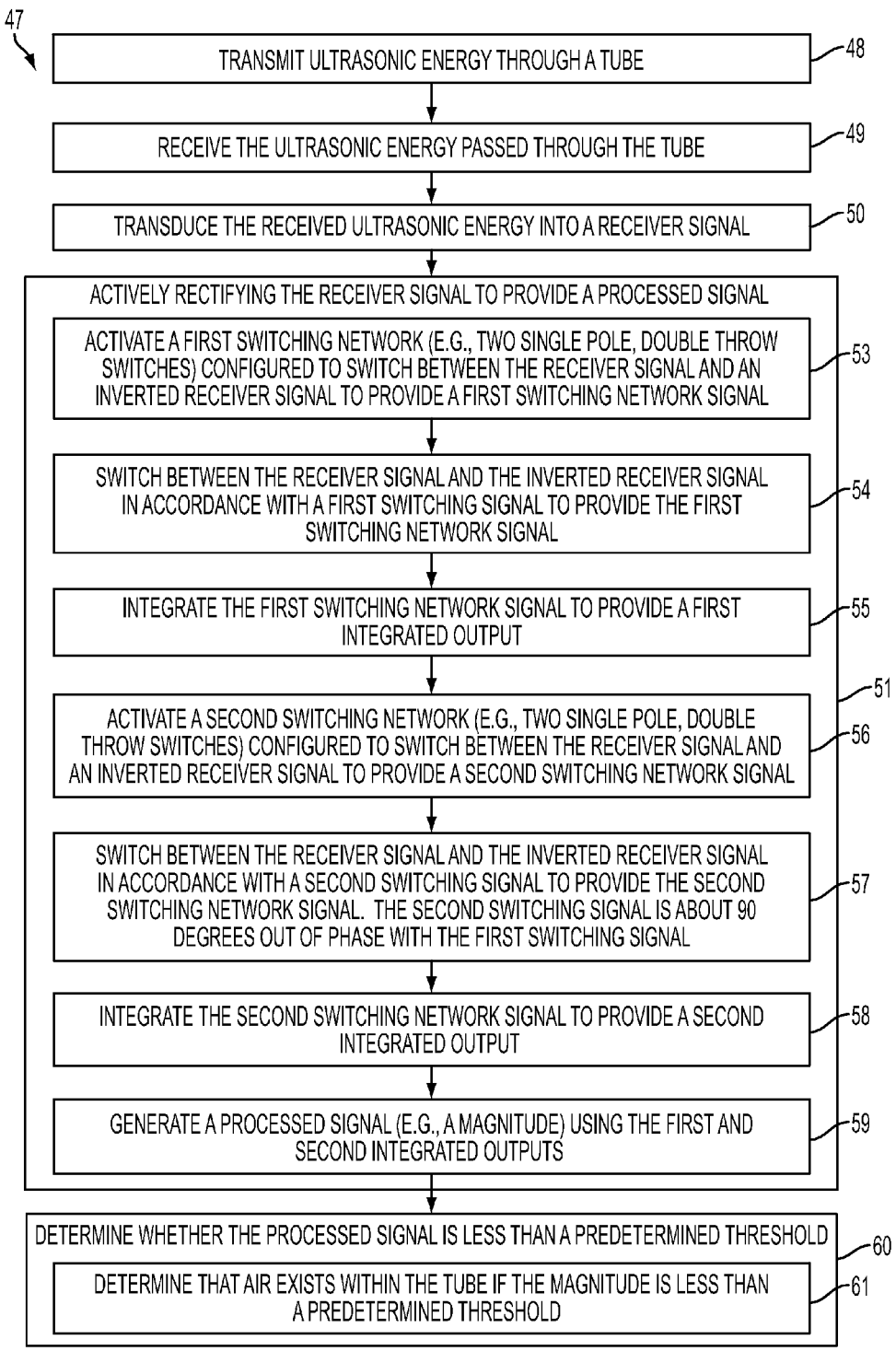
FIG. 5 shows a flow chart diagram of a method for detecting air in a fluid line, e.g., using the circuit of FIG. 4, in accordance with an embodiment of the present disclosure.

FIG. 5 shows a flow chart diagram of a method 47 for detecting air in a fluid line, e.g., using the circuit of FIG. 4, in accordance with an embodiment of the present disclosure.

The method 47 includes acts 48, 49, 50, 51 and 60. Act 51 may include acts 53-59 as subparts. Act 60 may include act 61 as a subpart.

Act 48 transmits ultrasonic energy through a tube. Act 49 receives the ultrasonic energy passed through the tube. Act 50 transduces the received ultrasonic energy into a receiver signal. Act 51 actively rectifies the receiver signal to provide a processed signal. Act 60 determines whether the processed signal is less that a predetermined threshold.

Act 51 may include acts 53 through act 59. Act 53 activates a first switching network (e.g., the two single pole, double throw switches 35 and 36 of FIG. 4) configured to switch between the receiver signal and an inverted receiver signal to provide a first switching network signal. For example, act 51 may activate the first switching network by providing power thereto and/or starting a first switching signal.

Act 54 switches between the receiver signal and the inverted receiver signal in accordance with a first switching signal to provide the first switching network signal. Optionally, an amplifier, e.g., the amplifier 33 of FIG. 4, is part of the switching network and amplifies the first switching network signal. Act 55 integrates the first switching network signal to provide a first integrated output. Act 56 activates a second switching network (e.g., the two single pole, double throw switches) configured to switch between the receiver signal and an inverted receiver signal to provide a second switching network signal. Act 57 switches between the receiver signal and the inverted receiver signal in accordance with a second switching signal to provide the second switching network signal. The second switching signal is about 90 degrees out of phase with the first switching signal. Optionally, an amplifier, e.g., the amplifier 34 of FIG. 4, is part of the switching network and amplifies the second switching network signal. Act 58 integrates the second switching network signal to provide a second integrated output. Act 59 generates a processed signal (e.g., a magnitude) using the first and second integrated outputs.

Act 60 may include act 61, which determines that air exists within the tube if the magnitude is less that a predetermined threshold.

Figure 6:
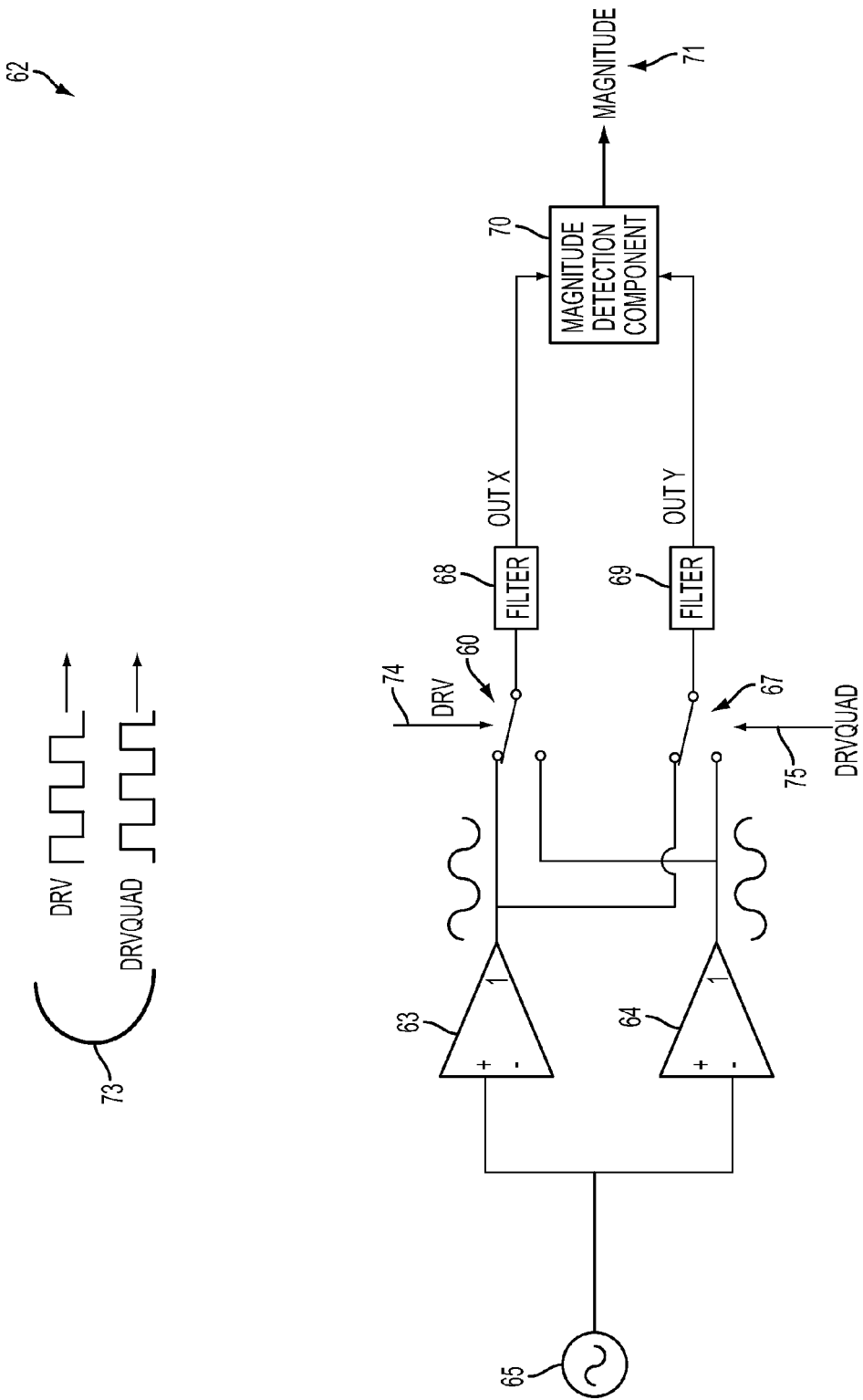
FIG. 6 shows a schematic diagram of a circuit for detecting air in a fluid line using active rectification in accordance with an embodiment of the present disclosure.

FIG. 6 shows a schematic diagram of a circuit 62 for detecting air in a fluid line using active rectification in accordance with an embodiment of the present disclosure. The circuit 62 includes a first amplifier 63, a second amplifier 64, a first filter 68, a second filter 69, and a magnitude detection component 70.

A source 65 represents the signal from an ultrasonic transducer that receives ultrasonic energy, e.g., a receiver signal electrically coupled to the ultrasonic transducer. The source 65 is amplified by an amplifier 63 to provide an amplified receiver signal. The source 65 is also amplified by an inverting amplifier 64 to provide an inverted and amplified receiver signal. The amplification by the amplifier 63 may be less than 1, equal to 1, or more than 1. The amplification by the amplifier 64 may be less than −1, equal to −1, or more than −1. For example, the amplifier 63 may be a voltage follower, and the amplifier 64 may be an inverter.

Both of the outputs from the amplifiers 63, 64 are provided to a first switch 66 and a second switch 76. The first switch 66 switches between the output of the first amplifier 63 and the output of the second amplifier 64 in accordance with a switching signal 74. The switching signal 74 is synchronized with the ultrasonic energy, e.g., the switching signal 74 is synchronized with the signal used to drive the ultrasonic transducer (e.g., the transmitter 11 of FIG. 2).

The second switch 67 also switches between an amplified receiver signal and an inverted and amplified receiver signal in accordance with a second switching signal 75 (e.g., a quadrature signal). The second switching signal 75 is synchronized with the first switching signal 74, and the second switching signal 75 is synchronized with the driving signal and has a phase angle that is about 90 degrees out of phase relative to the first switching signal 74 (as illustrated by the timing diagram 73).

The circuit 62 also includes a first filter 68 and a second filter 69, which may be integrators. That is, the first filter 68 may integrate the signal from the first switch (forming an Out X value) and the second filter 69 may integrate the signal from the second filter 60 (forming an Out Y value).

The first and second filters 68, 69 may integrate for a predetermined amount of time and may also be reset prior to the beginning of the predetermined amount of time. The magnitude detection component 70 may determine the magnitude 71 by using Formula 1, provided above.

Figure 7:
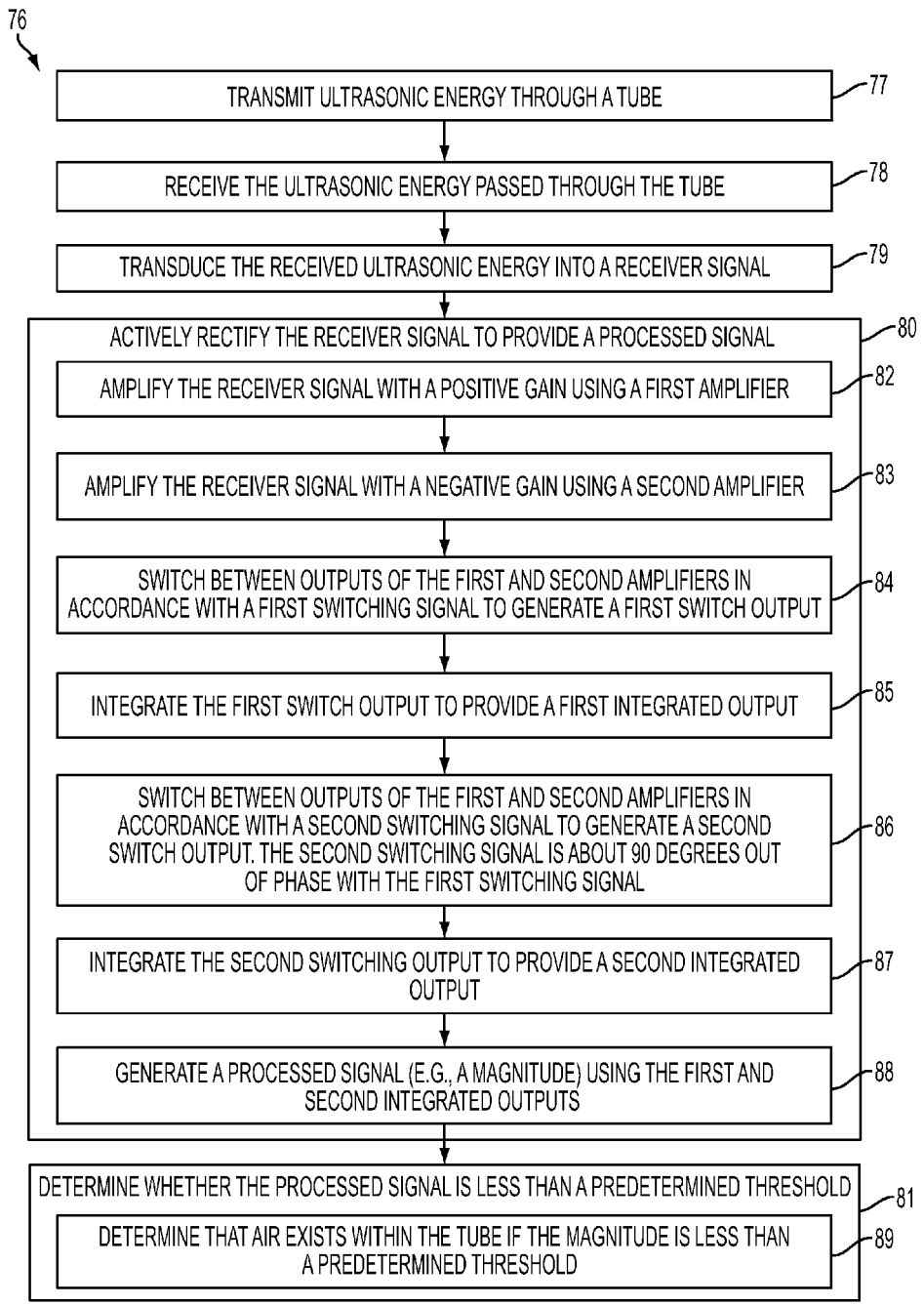
FIG. 7 shows a flow chart diagram of a method for detecting air in a fluid line, e.g., using the circuit of FIG. 6, in accordance with an embodiment of the present disclosure

FIG. 7 shows a flow chart diagram of a method 76 for detecting air in a fluid line, e.g., using the circuit of FIG. 6, in accordance with an embodiment of the present disclosure. The method 76 includes acts 77-81. Act 80 includes acts 82-88, in certain embodiments. Act 81 includes act 89, in certain embodiments.

Act 77 transmits ultrasonic energy through a tube. Act 78 receives the ultrasonic energy passed through the tube. Act 79 transduces the received ultrasonic energy into a receiver signal. Act 80 actively rectifies the receiver signal to provide a processed signal. Act 81 determines whether the processed signal is less that a predetermined threshold.

Act 80 may include acts 82-88. Act 82 amplifies the receiver signal with a positive gain using a first amplifier. Act 83 amplifies the receiver signal with a negative gain using a second amplifier. Act 84 switches between outputs of the first and second amplifiers in accordance with a first switching signal to generate a first switch output. Act 85 integrates the first switch output to provide a first integrated output. Act 86 switches between outputs of the first and second amplifiers in accordance with a second switching signal to generate a second switch output. The second switching signal is about 90 degrees out of phase with the first switching signal. Act 87 integrates the second switch output to provide a second integrated output. Act 88 generates a processed signal (e.g., a magnitude) using the first and second integrated outputs.

As previously mentioned, act 81 may include act 89. Act 89 determines that air exists within the tube if the magnitude is less that a predetermined threshold.

Figure 8A:
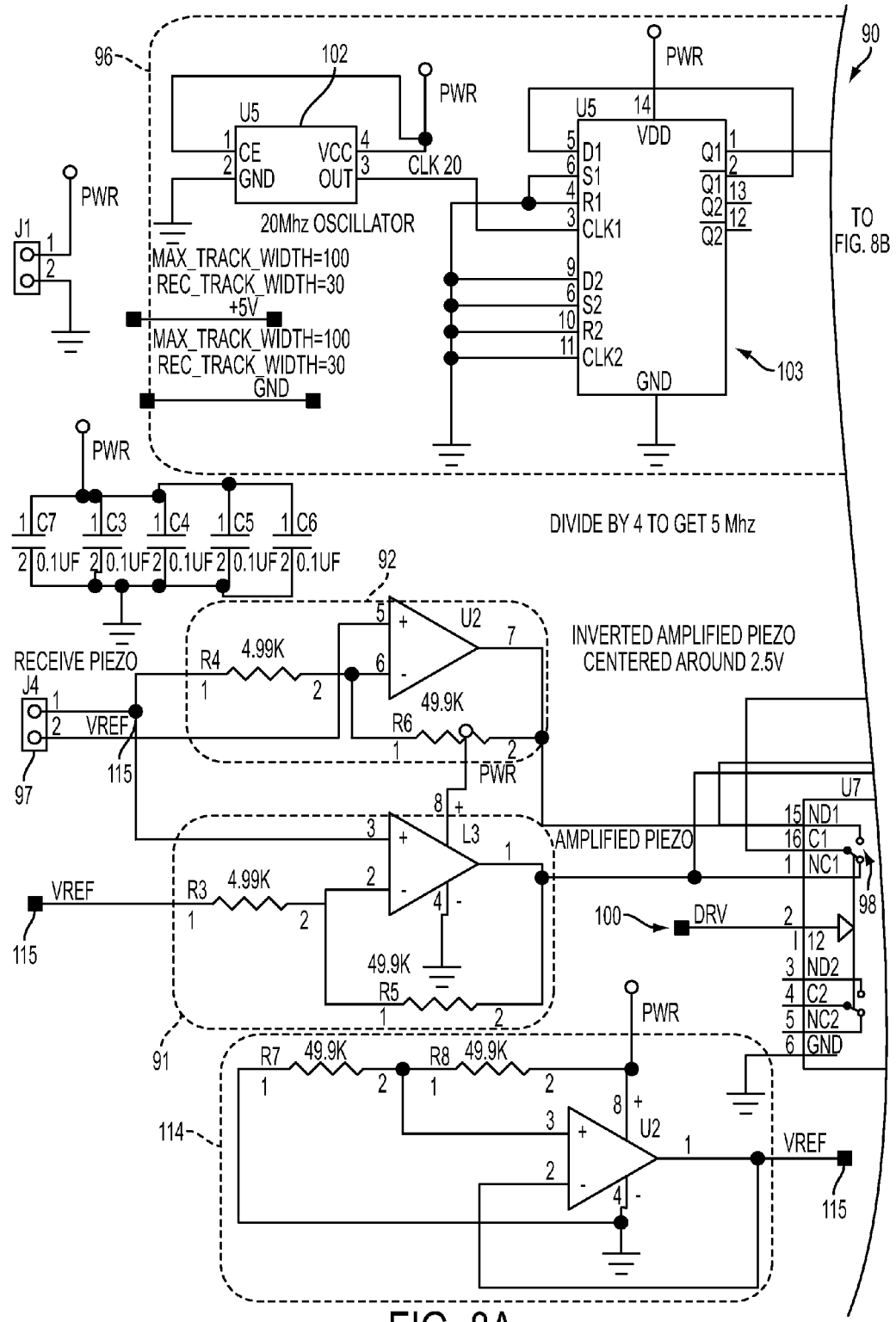
FIGS. 8A-8B show a circuit schematic for detecting air in a fluid line using active rectification in accordance with an embodiment of the present disclosure.
Figure 8B:
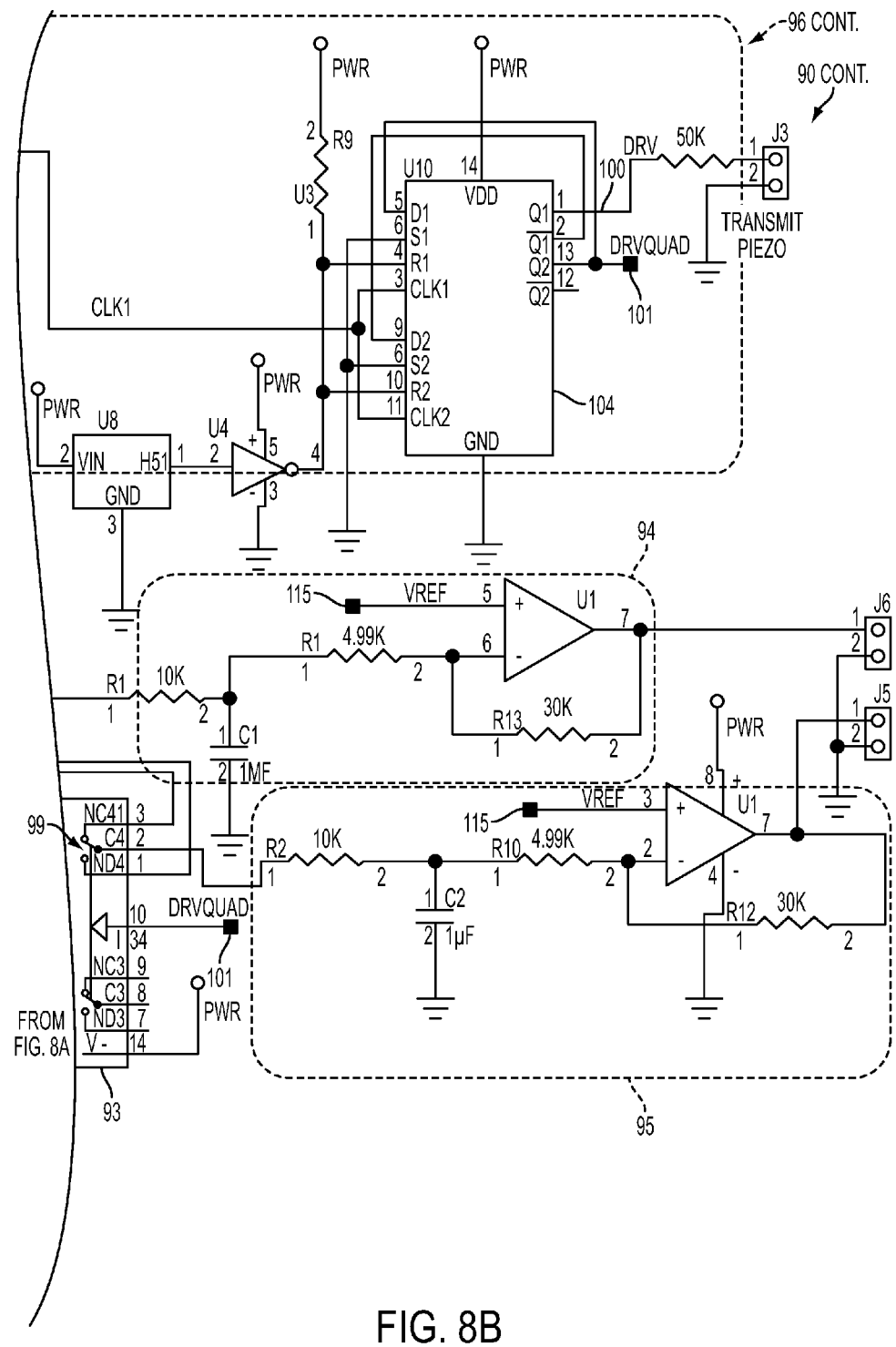

FIGS. 8A-8B show a circuit schematic 90 for detecting air in a fluid line using active rectification in accordance with an embodiment of the present disclosure.

The circuit 90 receives a receiver signal via connection 97 from a receiver. A first amplifier 91 amplifies the receiver signal and a second amplifier 92 inverts and amplifies the receiver signal from the connection 97. The first and second amplifiers 91, 92 use a reference voltage 115.

A semiconductor device 93 includes switches 98 and 99, which switch between the amplified signal from the first amplifier 91 and the amplified and inverted signal from the second amplifier 92. The first switch 98 switches in accordance with a first switching signal 100 and the second switch 99 switches in accordance with a second switching signal 101 (e.g., a quadrature signal).

The circuit 90 also includes a first filter 94 and a second filter 95. The output of the first switch 98 is sent to the first filter 94. The output of the second switch 99 is likewise sent to the second filter 95. The first and second filters 94 and 95 are inverting filters. The outputs of the first and second filters 94, 95 may be used to calculate a magnitude and thus determine if air exists within a tube, e.g., the tube 6 of FIG. 2.

A reference generating circuit 114 generates the reference voltage 115 that is used as a reference from the first and second amplifiers 91, 92, and the first and second filters 94, 95. The reference voltage 115 may be subtracted out of the results of the first and second filters 94, 95 when determining the magnitude.

The first and second switching signals 100 and 101 may be generated by a signal generating circuit 96. The signal generating circuit 96 includes a reference clock 102, a divider 103 (the divider may formed using a dual D-type flip flop), and a dual D-type flip flop 104 to generate the first and second switching signals 100, 101, such that the second switching signal 101 is 90 degrees out of phase relative to the first switching signal 100. The first and second switching signals 100, 101 generated by the signal generating circuit 96 are fed into the semiconductor device 93 that includes switches 98 and 99.

FIGS. 9-12 show several signal vs. time traces to illustrate the operation of the circuit shown in the circuit schematic of FIG. 8 in accordance with an embodiment of the present disclosure.

Figure 9:
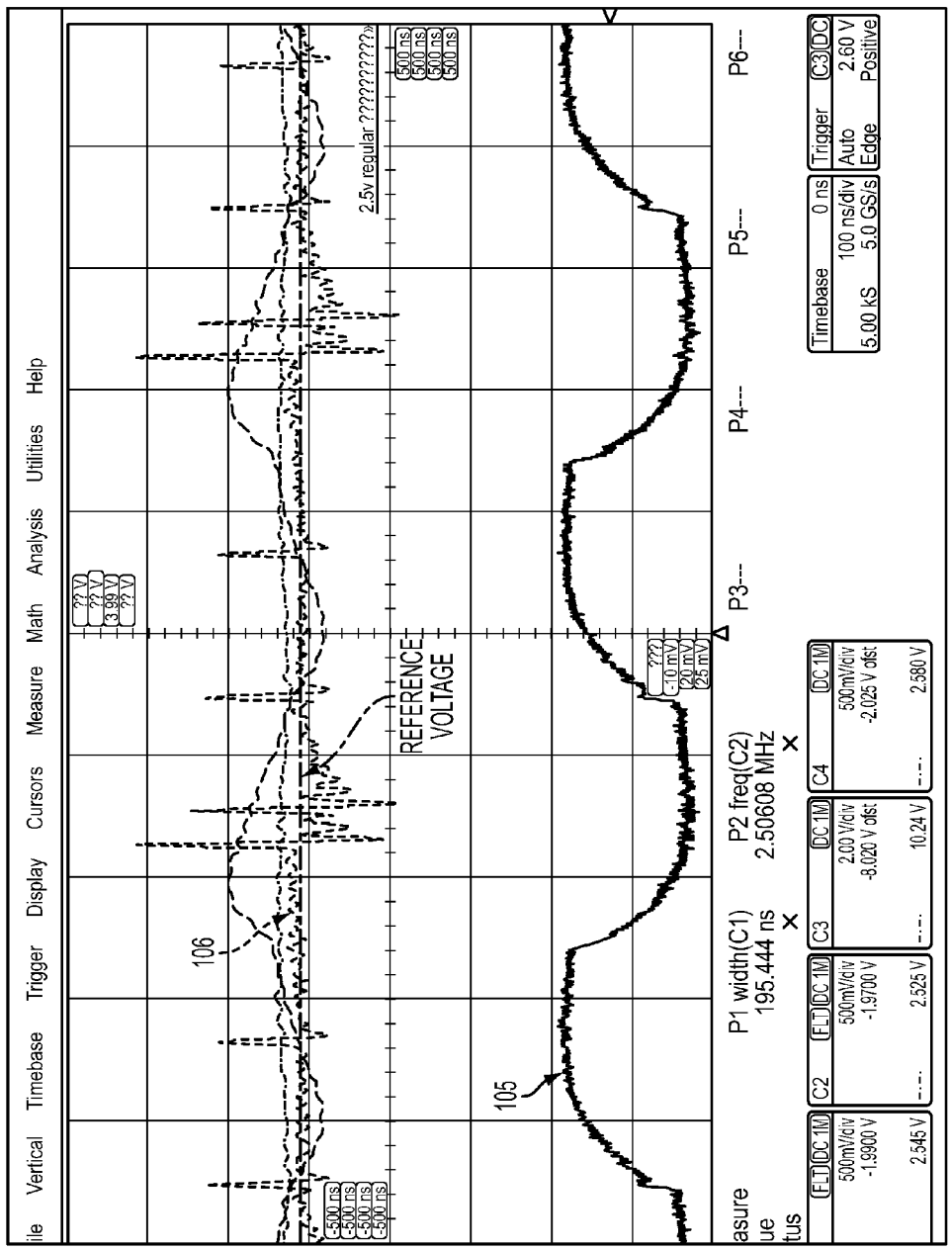
FIGS. 9-12 show several signal vs. time traces to illustrate the operation of the circuit shown as the circuit schematic of FIGS. 8A-8B in accordance with an embodiment of the present disclosure.

FIG. 9 shows a signal trace 105 that is the signal used to drive a transmitter, such as a piezoelectric element, (e.g., the first switching signal 100 may be used to drive a piezoelectric element). FIG. 9 also shows a signal trace 106 that is the result of the synchronous rectification with no water in a tube (note that it is centered around the reference voltage). The signal trace 106 may be a result from either of the outputs from the switches 98 or 99. Note that the signal trace 106 shows little relative ac movement around the reference voltage. When air exists within the tube, very little (or none) of the ultrasonic energy reaches the receiver, therefore, the outputs of the first filter 94 and the second filter 95 should be about equal to the reference voltage (however, some offset errors of the amplifiers may skew the results by a DC voltage).

Figure 10:
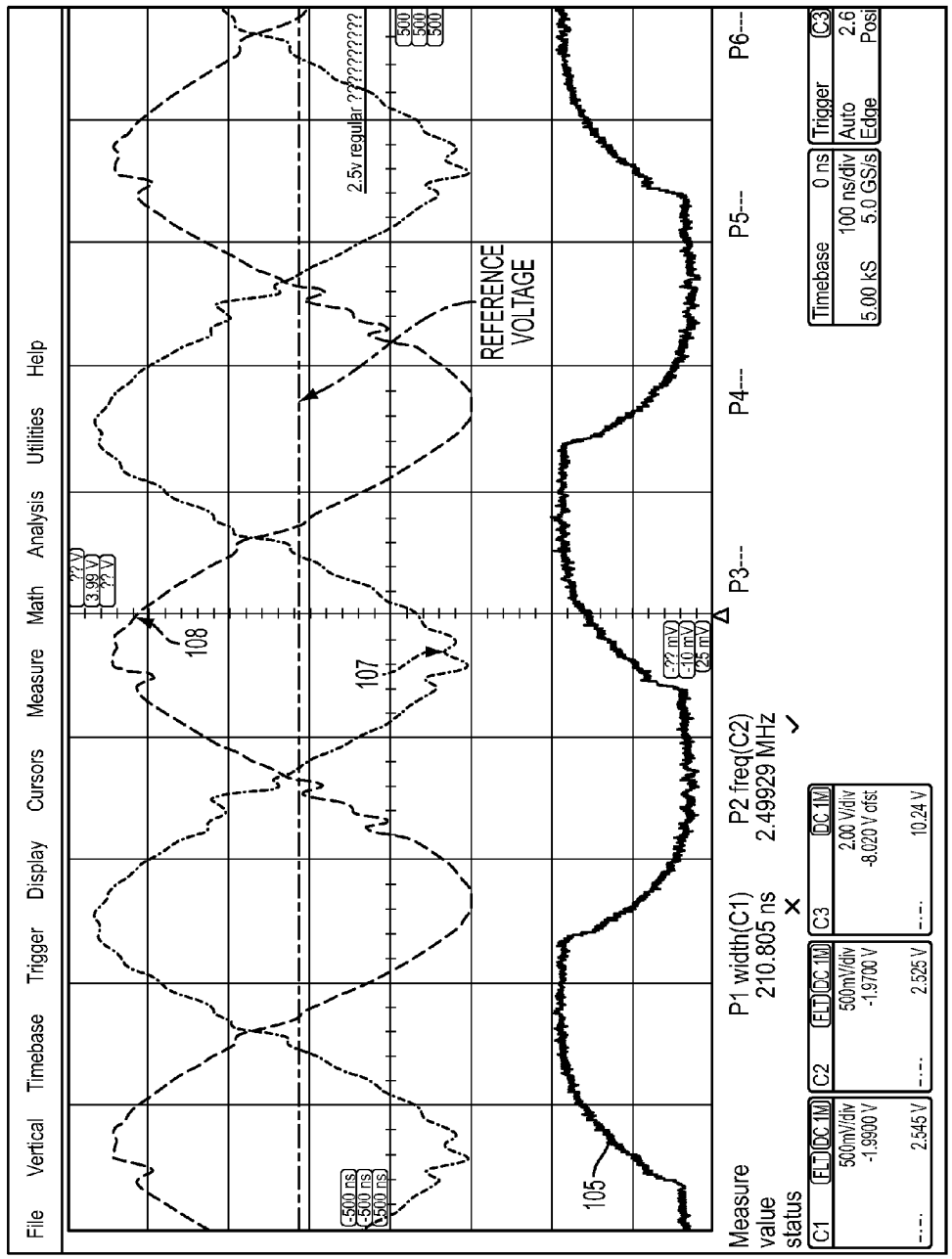

FIG. 10 shows signal traces 105, 107 and 108. The signal trace 105 is the voltage applied to the ultrasonic transducer. Trace 107 shows the amplified signal from the first amplifier 91 and trace 108 shows the inverted and amplified signal from the second amplifier 92. FIG. 10 shows the case in which water is completely in the tube (i.e., no air is located between the transmitter). The alternating waveforms (e.g., the traces 107 and 108) that result from a relative strong receiver signal is a results of the ultrasonic energy reaching the receiver because there is water within the tube. That is, the water helps more of the ultrasonic energy reach the receiver (e.g., the receiver 8 of FIG. 2).

Figure 11:
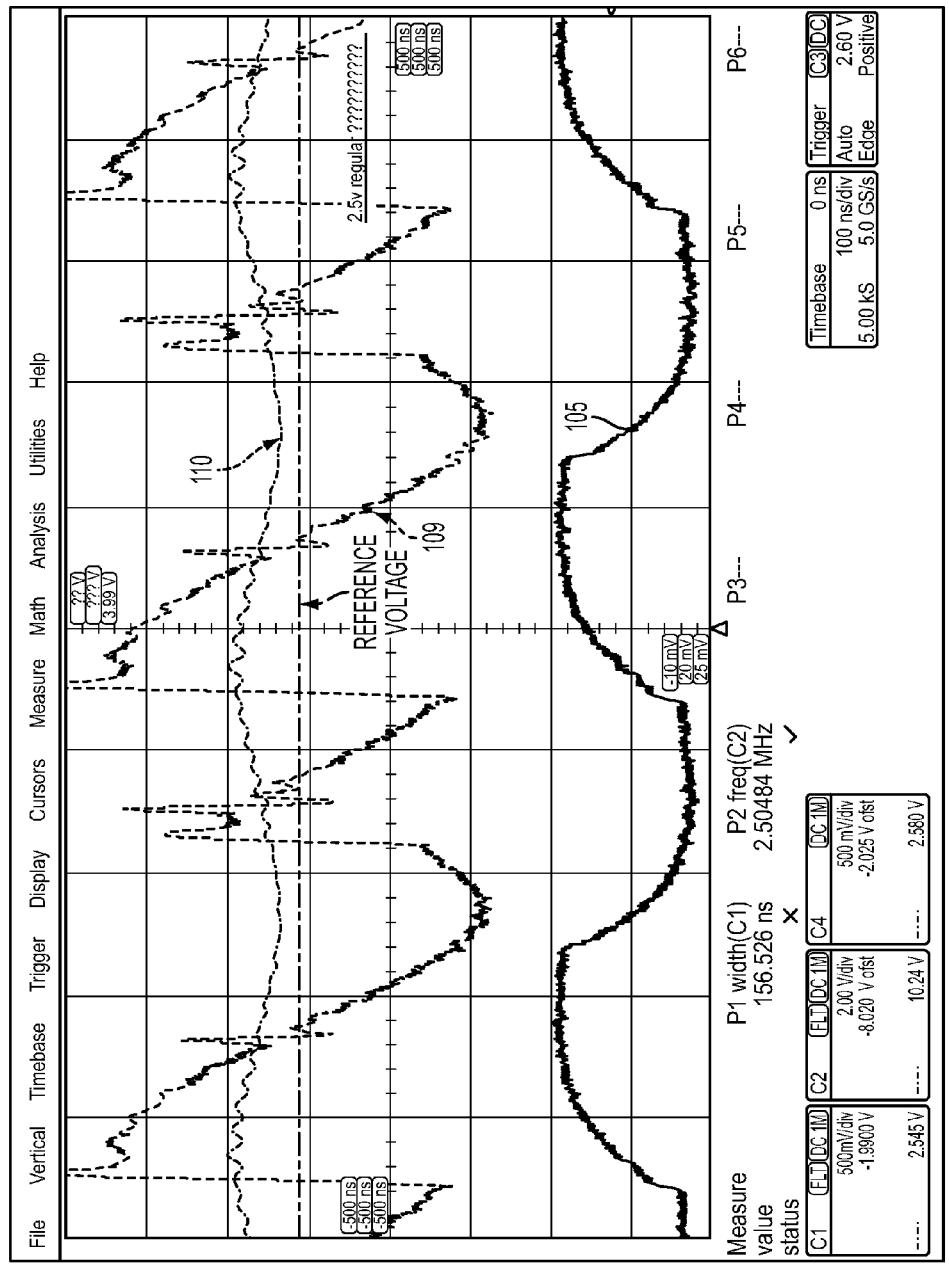

FIG. 11 shows signal traces 105, 109, and 110. The signal trace 105 is the voltage applied to the ultrasonic transducer. The signal trace 109 shows the result of the synchronous rectification for the in-phase signal (e.g., the output of the switch 98 of FIGS. 8A-8B). The trace signal 110 shows the filtered, inverted and amplified result of the output of the switch 98, i.e., the output of the filter 94. The trace signal 110 illustrates a condition in which the filtered results from a filter 94 does not deviate much from the reference voltage; in this condition, the phase of the signal from the amplifier is such that not much of the signal is output from the filter 94, but may instead predominantly show up as output from the second filter 95 (see FIGS. 8A-8B).

Figure 12:
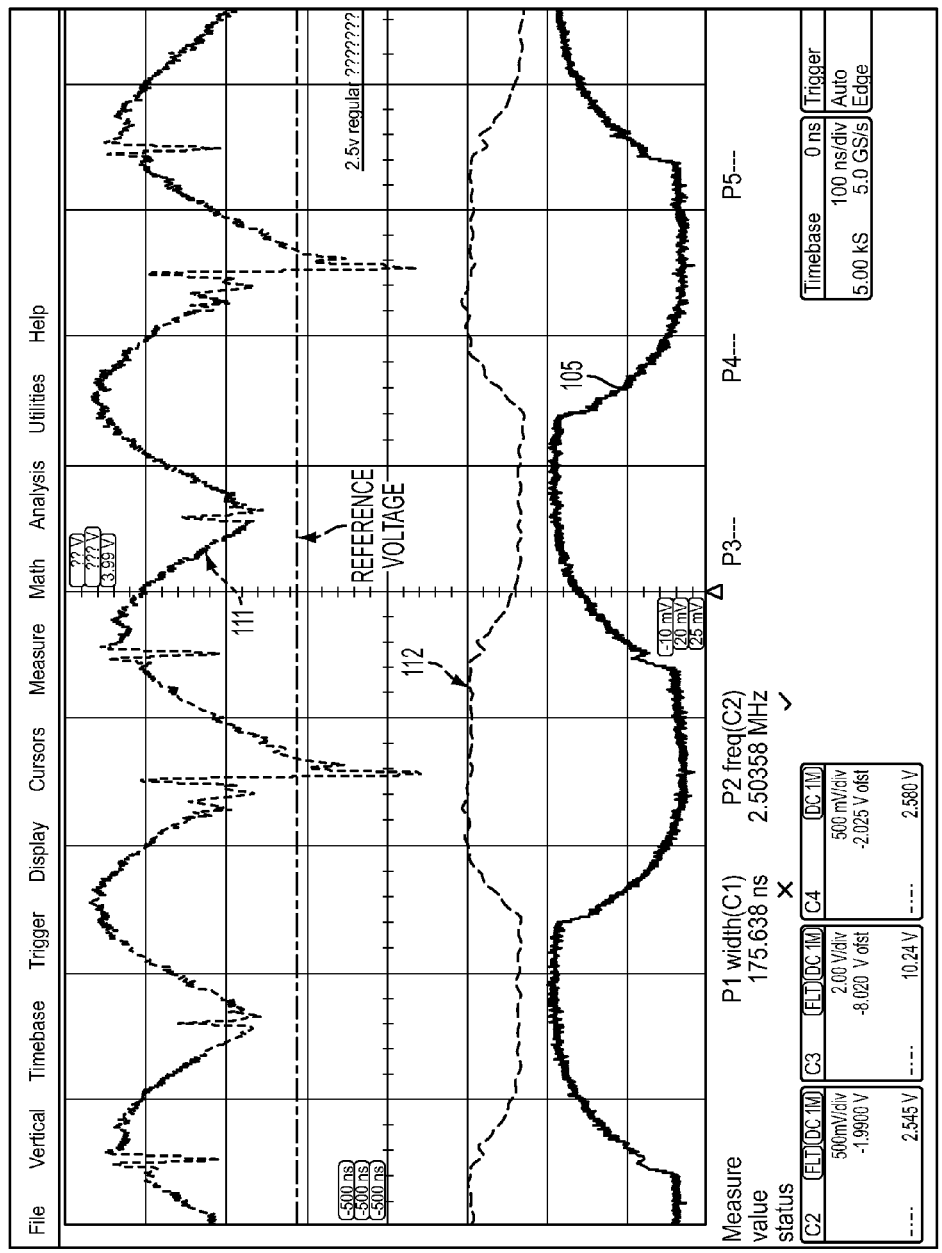

FIG. 12 shows signal traces 105, 111, and 112. The signal trace 105 is the voltage applied to the ultrasonic transducer. Signal trace 111 shows the results of the synchronous rectification for the quadrature phase, e.g., the output of the second switch 99. Note that the signal trace 111 deviates significantly from the reference voltage. Signal trace 112 is the filtered/inverted/amplified result from the signal represented by the signal trace 111. That is, the signal trace 112 shows the output of the second filter 95. Note that the signal 112 is significantly below the reference voltage because water in the tube carries much of the ultrasonic energy to the receiver.

FIGS. 13A-15 illustrate a schematic of a circuit 113 for detecting air in a fluid line using active rectification in accordance with an embodiment of the present disclosure. The circuit 113 receives a receiver signal via a connection 300. The circuit 113 includes a first amplifier 116 and a second amplifier 117. The first amplifier 116 is an inverting amplifier that amplifies and inverts the receiver signal from the connection 300. The second amplifier 117 amplifies the receiver signal from the connection 300. A reference generating circuit 200 provides a reference voltage to the first and second amplifiers 116, 117. The outputs of the first and second amplifiers 116, 117 are fed into first and second switching networks 118, 119.

The first switching network 118 switches between the amplified signal from the second amplifier 117 and the amplified and inverted signal from the first amplifier 116. The first switching network 118 is switched in accordance with a first switching signal. That is, the first switching network 118 includes a first switch 302 that is a single-pull, single-throw switch and a second switch 304 that is also a single-pull, single-throw switch. The first and second switches 302, 304 switch in accordance with the first switching signal such that: (1) when the first switch 302 is closed, the second switch 304 is open; and (2) when the first switch 302 is opened, the second switch 304 is closed. That is, the first switch 302 may receive the first switching signal such that a high value from the first switching signal closes the first switch 302, and the second switch 304 receives an inversion of the first switching signal that causes the second switch 304 to close when the inversion of the first switching signal is high.

The output of the first switching network 118 is fed into a first integrator 120 that can be sampled by a first sample-and-hold circuit 122 and/or by a second sample-and-hold circuit 123. The first sample-and-hold circuit 122 works in conjunction with the first integrator 120 to integrate the output of the first switching network 118 during a time that includes the time in which the ultrasonic energy is received by the receiver. The second sample-and-hold circuit 122 works in conjunction with the first integrator 120 to integrate the output of the first switching network 118 during a time in which the receiver signal receives no ultrasonic energy. The second sample-and-hold circuit 122 integrates the output of the first switching network 118 to produce a diagnostic signal in order to determine at least one error that occurs in various places within the circuit 120, such as offset errors in produced by the first and second amplifiers 116, 117. The error may be used to adjust the reference voltage to null out the offset voltages from op-amps contained within the circuit 113 that is part of the path which generates the output from the second sample-and-hold circuit 123. Additionally, alternatively, or optionally, if the diagnostic signal is above a threshold, the CPLD and/or a processor may determine that a fault condition exists and may then alarm or halt operation of the infusion pump, for example.

The second switching network 119 switches between the amplified signal from the second amplifier 117 and the amplified and inverted signal from the first amplifier 116. The second switching network 118 is switched in accordance with a second switching signal that is 90 degrees out of phase (or is about 90 degrees out of phase) with the first switching signal.

The output of the second switching network 119 is fed into a second integrator 121 that can be sampled by a third sample-and-hold circuit 124 and/or a fourth sample-and-hold circuit 125. The third sample-and-hold circuit 124 works in conjunction with the second integrator 121 to integrate the output of the second switching network 119 during a time that includes the time in which the ultrasonic energy is received by the receiver. The fourth sample-andhold circuit 125 works in conjunction with the second integrator 121 to integrate the output of the second switching network 119 during a time in which no ultrasonic energy is received in order to determine at least one error (to produce a quadrature diagnostic signal). The error may be used to adjust the reference voltage to null out the offset voltages from op-amps contained within the circuit 113 that is part of the path which generates the output from the fourth sample-and-hold circuit 123.

Figure 14A:
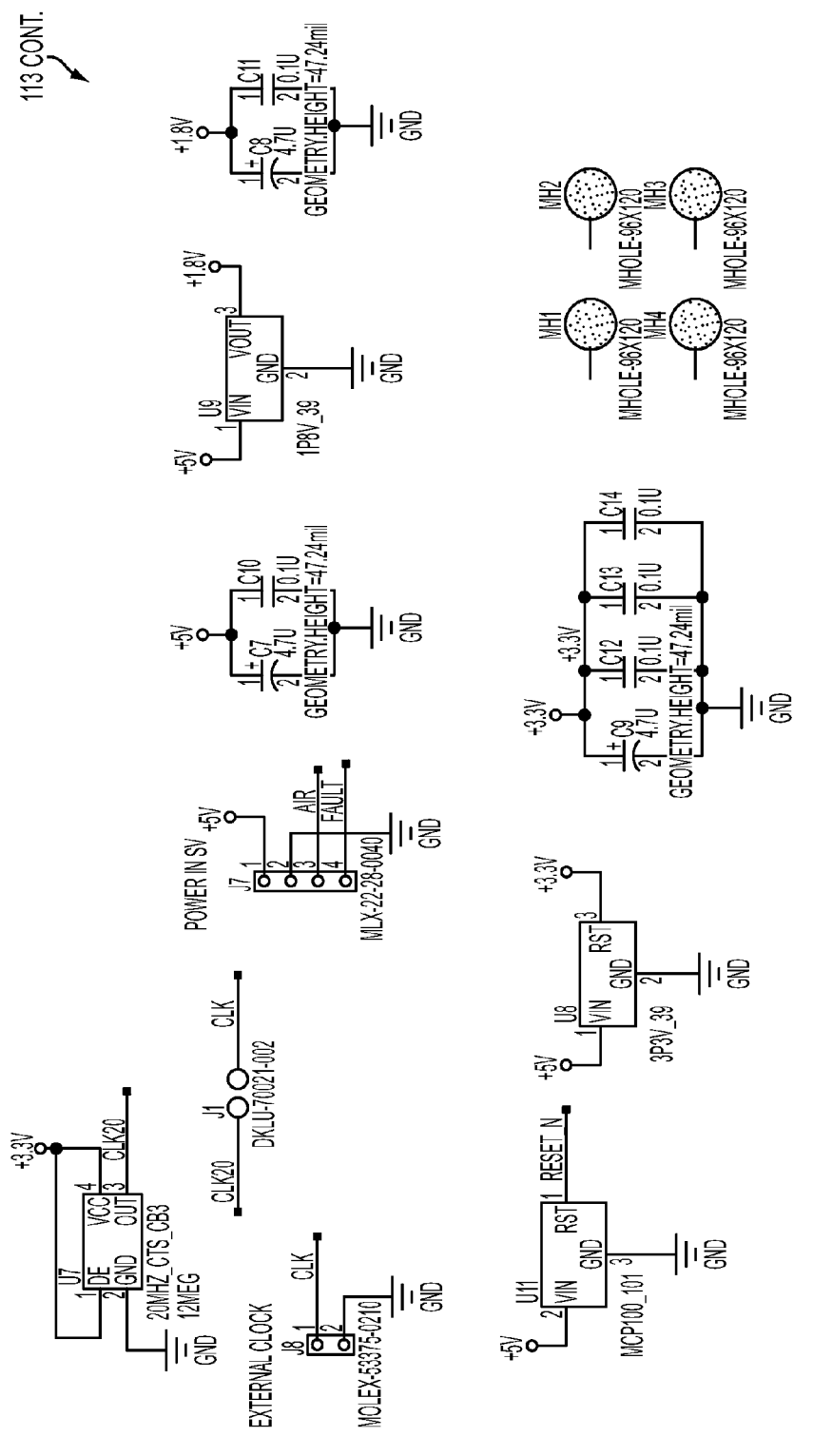
Figure 14B:
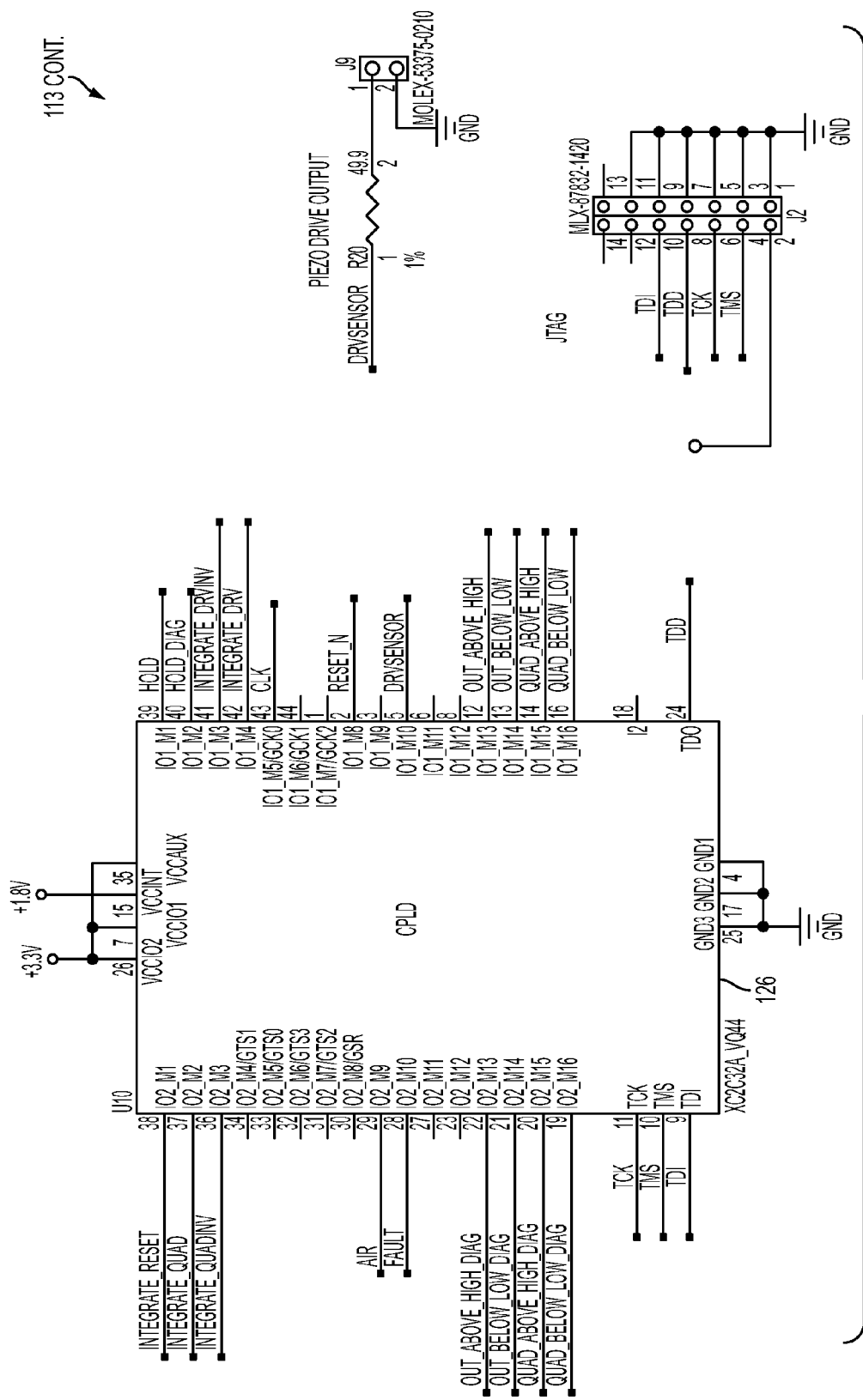

FIG. 14A shows various power supplies used by the circuit 113. FIG. 14B shows a CPLD 126 that can generate the first and second switching signals and can receive various signals. The CPLD 126 can generate the first and second switching signals. The CPLD 126 can also generate an inversion of the first switching signal and an inversion of the second switching signal.

Figure 15:
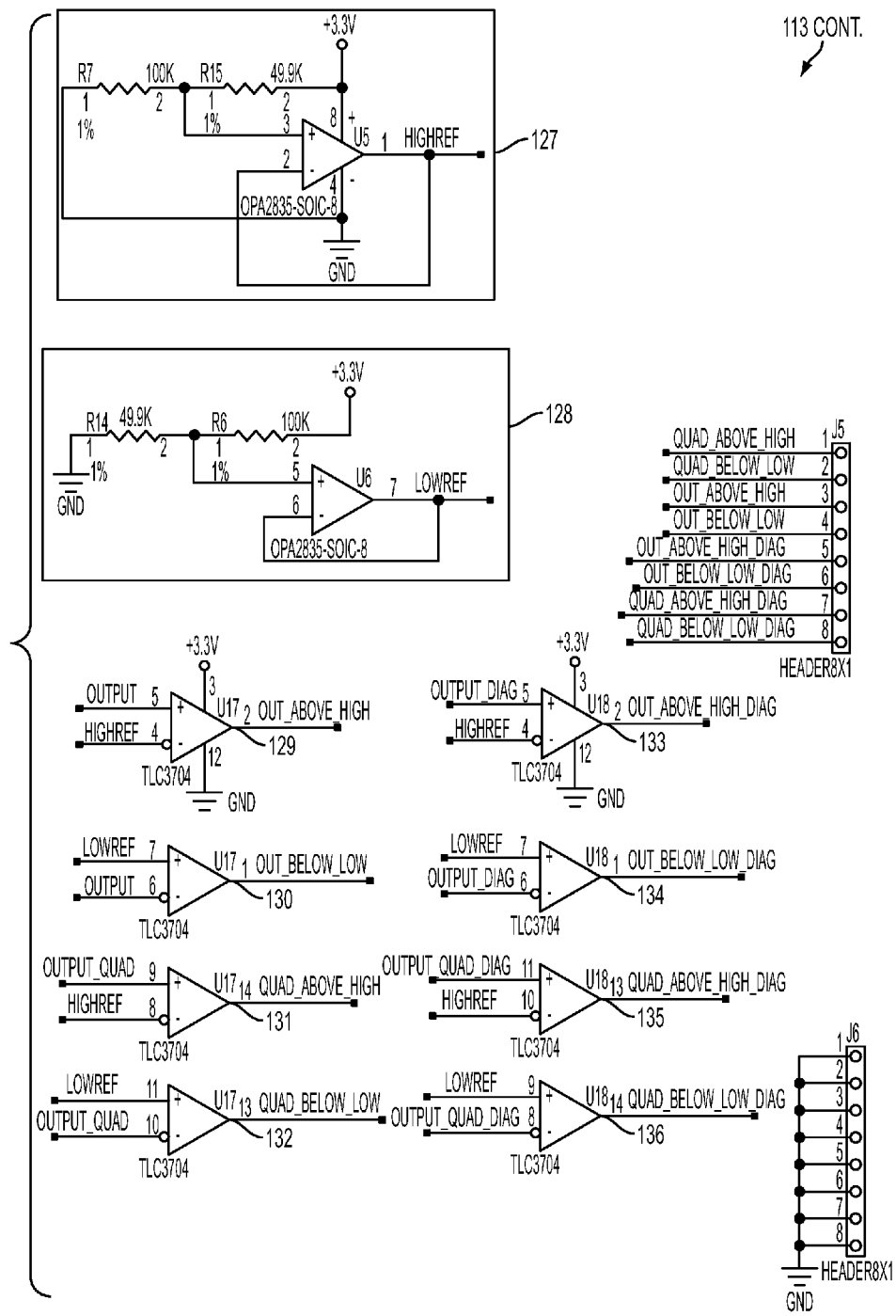

Furthermore, the CPLD 126 receives the gross comparison signals from the comparators 129-136 shown in FIG. 15. A high-threshold circuit 127 generates a high threshold reference value, and a low-threshold circuit 128 generates a low threshold. The high and low thresholds are used by the comparators 129-136. The outputs of the comparators 129-136 are fed to the CPLD 126. In some embodiments, the CPLD 126 uses only the outputs of the comparators 129-136. However, in some specific embodiments of the present disclosure, the CPLD 126 is coupled to an analog-to-digital converter so that the CPLD 126 can receive one or more digital signals that represent an analog signal, such as the analog OUTPUT signal (i.e., the output of the first sample-and-hold circuit 122), the analog OUTPUT_DIAG signal (i.e., the output of the second sample-and-hold circuit 123), the analog OUTPUT_QUAD_DIAG signal (i.e., the output of the third sample-and-hold circuit 124), and the analog OUTPUT_QUAD signal (i.e., the output of the fourth sample-and-hold circuit 124); this allows the CPLD 126 to use these signals without the need for the comparators 129-136 (however, the comparators 129-132 may still be present for redundancy, in some embodiments).

The comparator 129 compares the output of the first integrator 122 to the high threshold. The comparator 130 compares the output of the first integrator 122 to the low threshold. The comparator 131 compares the output of the second integrator 122 (e.g., the quadrature output) to the high threshold. The comparator 132 compares the output of the second integrator 122 to the low threshold.

The comparator 133 compares the output diagnostic to the high threshold. The comparator 134 compares the output diagnostic to the low threshold. The comparator 135 compares the output quadrature diagnostic to the high threshold. The comparator 136 compares the quadrature output diagnostic to the low threshold.

When one of the comparators 129-132 outputs a true value (after an appropriate sample-and-hold has been performed), then the CPLD 126 may determine that water exists within the tube. When none of the comparators 129-132 are true, the CPLD 126 may determine that air exists within the tube. Comparators 133-136 may be used to determine that there is a fault condition which is causing the circuit to malfunction.

FIGS. 16-19 show several signal vs. time traces to illustrate the operation of the circuit shown in the circuit schematic of FIGS. 13A-15 in accordance with an embodiment of the present disclosure.

Figure 16:
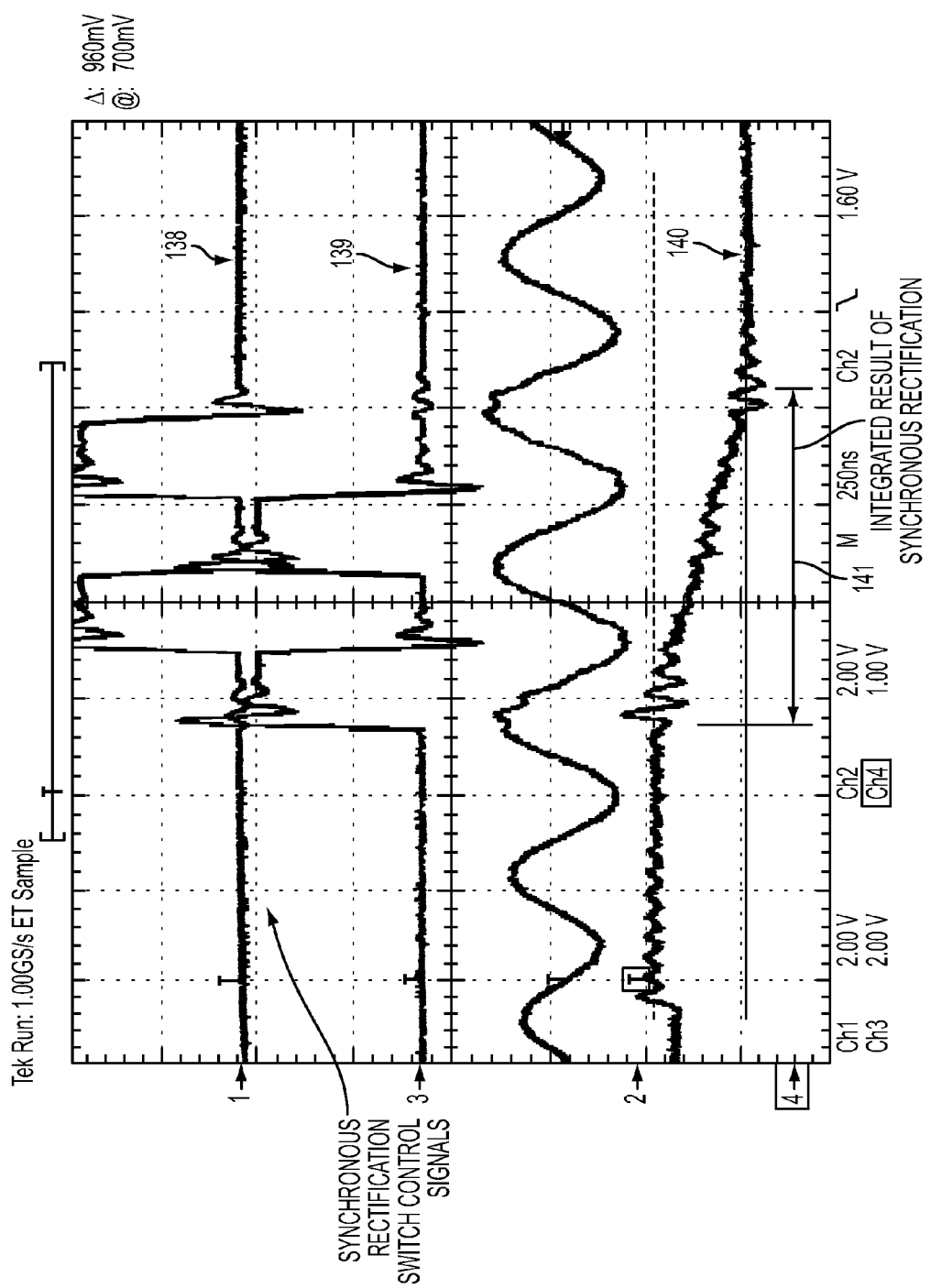
FIGS. 16-19 show several signal vs. time traces to illustrate the operation of the circuit shown in the circuit schematic of FIGS. 13A-15 in accordance with an embodiment of the present disclosure.

FIG. 16 shows the synchronous rectification switch control signals 138 and 139 (e.g., a first switching signal 138 and an inverse of the first switching signal 139 used to control the two switches 302, 304 within the switching network 118). FIG. 16 also shows the integrated result 140 of the synchronous rectification (e.g., the output of the integrator 120). An active portion 141 of the integrated result 140 is shown in which the receiver receives the ultrasonic energy.

Figure 17:
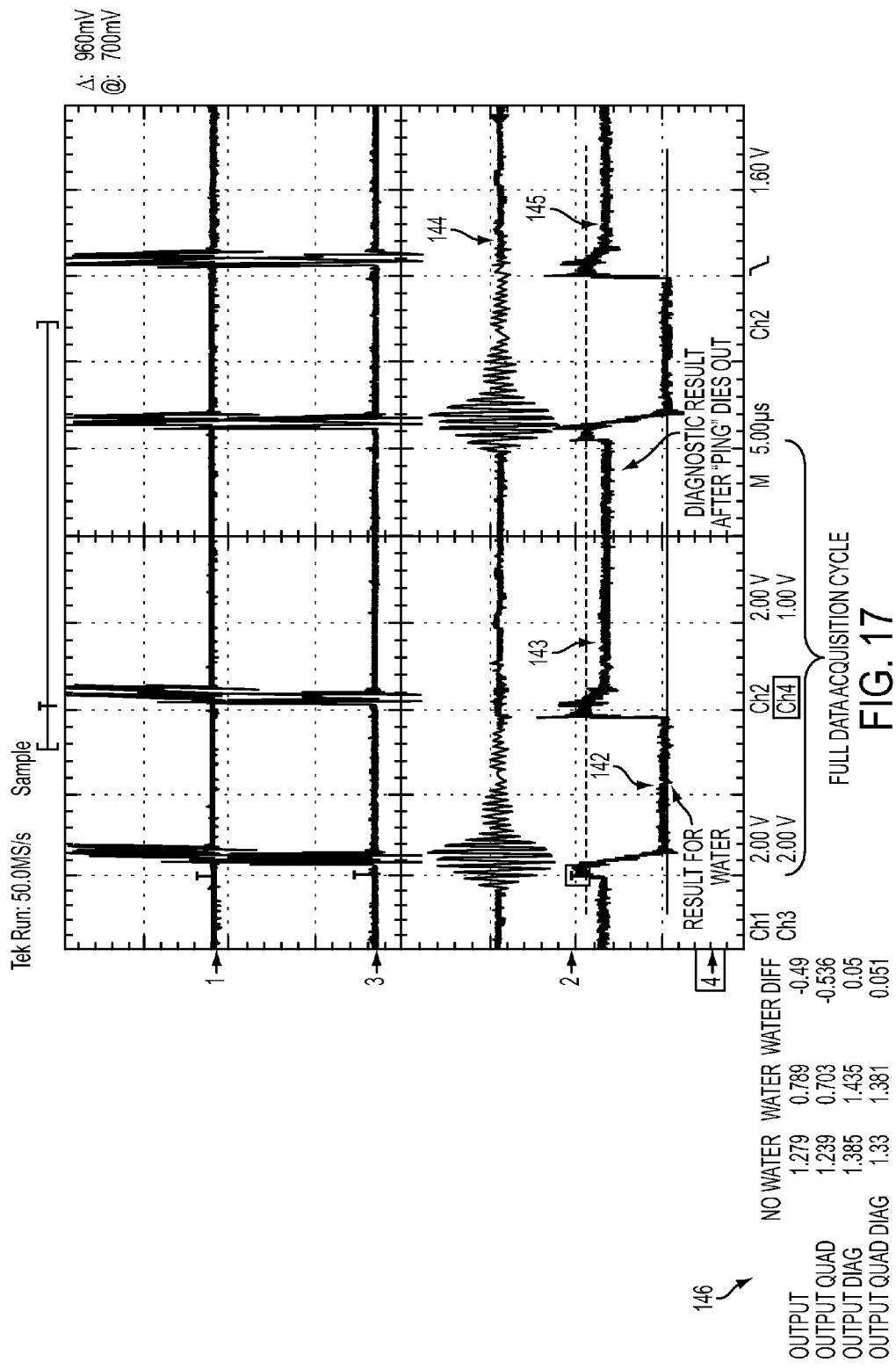
Figure 18:
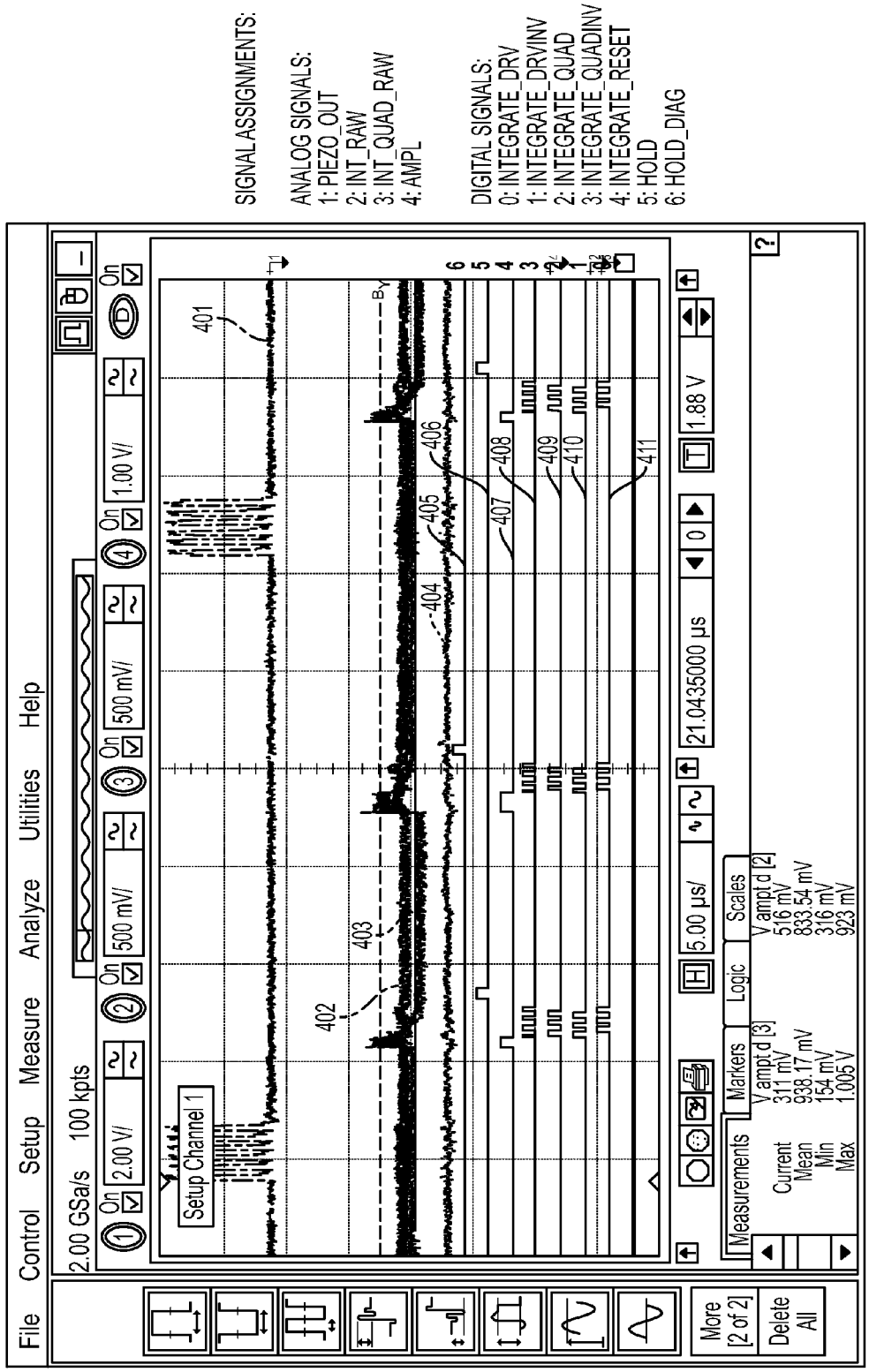
Figure 19:
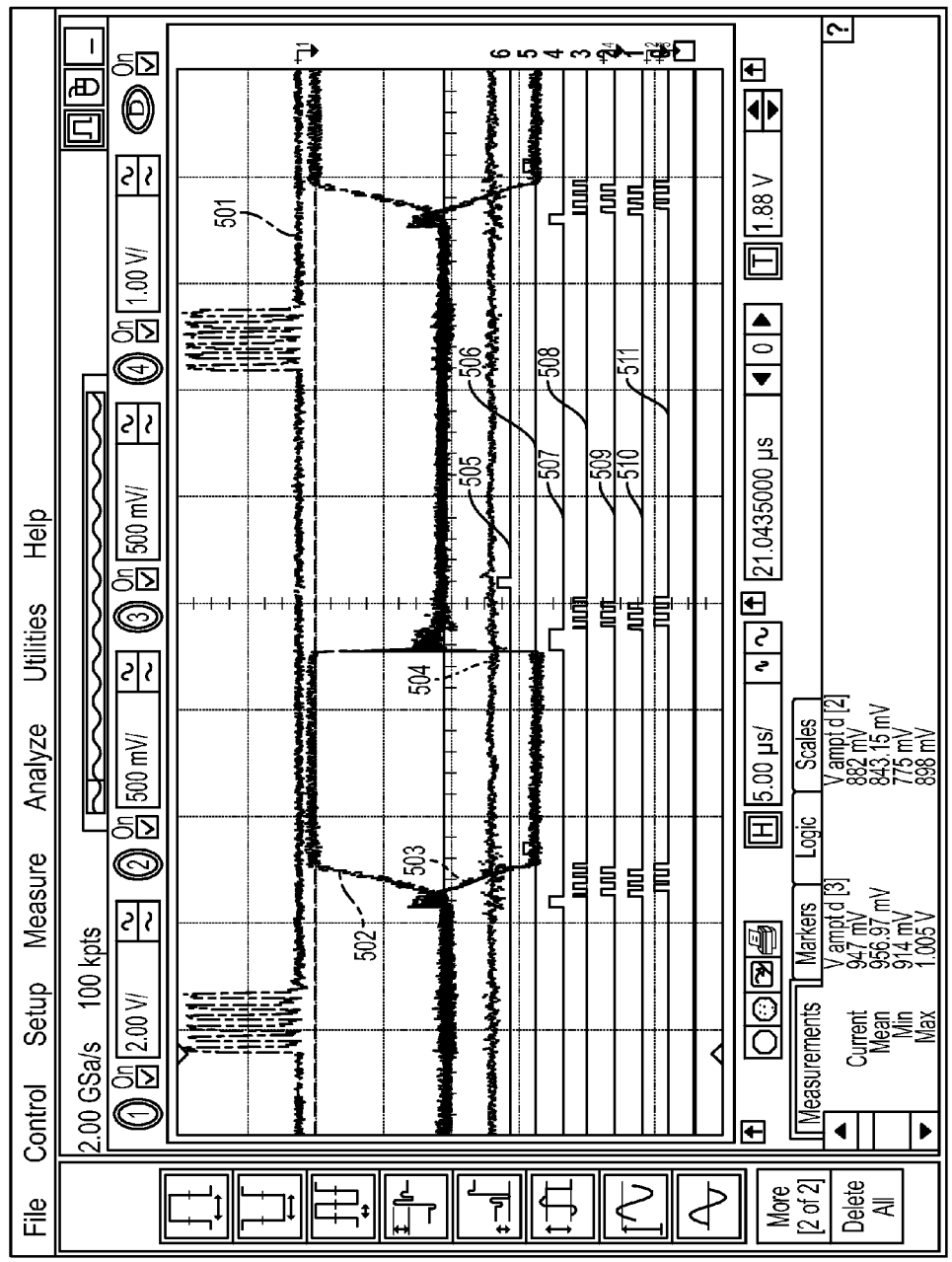

FIG. 17 shows the results 145 of the integrator (e.g., the output of the integrator 120) which includes a portion 142 that corresponds to water and a portion that corresponds to the diagnostic result 143. The receiver signal 144 is also shown for reference. Note that in the portion 143 that corresponds to the diagnostic portion, the "ping" had largely dissipated. The diagnostic portion 143 may be sampled by a sample-and-hold circuit (e.g., the sample-and-hold circuit 123 of FIG. 13C) which may be used to adjust the voltage fed into the op-amps as a reference such that the reference voltage nulls out some of the op-amp errors). FIG. 18 shows various output voltages for the output of the sample-and-hold circuits 122, 123, 124, 125 for the condition in which the tube has no water, and FIG. 19 shows the condition in which the tube does have water. The output values of the sample-and-hold circuits 122, 123, 124, 125 are summarized in chart 146 of FIG. 17 for various conditions.

FIG. 18 shows several traces 401-411 to illustrate various signals of the circuit 113 of FIGS. 13A-15. FIG. 18 shows the condition in which air is within the tube. Signal trace 401 is the signal sent to drive the transmitting ultrasonic transducer. Signal trace 402 is the output of the first integrator 118. Signal trace 403 is the output of the second integrator 119. Signal trace 404 is the analog signal from the receiver via connection 300. Signal trace 405 is the signal sent to the second and third sample-and-hold circuits 123, 124 to signal them to sample and hold the diagnostic signals (i.e., to generate the OUTPUT_DIAG and the OUTPUT_QUAD_DIAG signals).

Signal trace 406 is the signal sent to the first and fourth sample-and-hold circuits 122, 125 to signal them to sample and hold the outputs of the integration results (i.e., to generate the OUTPUT and the OUTPUT_QUAD signals). Signal trace 407 is the integrator reset signal to reset the first and second integrators 120, 121. Signal traces 408 and 409 are the switching signals sent to the second switching network 119. Signal trace 410 and 411 are the switching signals sent to the second switching network 119.

FIG. 19 shows several traces 501-511 to illustrate various signals of the circuit 113 of FIGS. 13A-15. FIG. 19 shows the condition in which water is within the tube. Signal trace 501 is the signal sent to drive the transmitting ultrasonic transducer. Signal trace 502 is the output of the first integrator 118. Signal trace 503 is the output of the second integrator 119. Signal trace 504 is the analog signal from the receiver via connection 300. Signal trace 505 is the signal sent to the second and third sample-and-hold circuits 123, 124 to signal them to sample and hold the diagnostic signals (i.e., to generate the OUTPUT_DIAG and the OUTPUT_QUAD_DIAG signals).

Signal trace 506 is the signal sent to the first and fourth sample-and-hold circuits 122, 125 to signal them to sample and hold the outputs of the integration results (i.e., to generate the OUTPUT and the OUTPUT_QUAD signals). Signal trace 507 is the integrator reset signal to reset the first and second integrators 120, 121. Signal traces 508 and 509 are the switching signals sent to the second switching network 119. Signal trace 510 and 511 are the switching signals sent to the second switching network 119.

Referring now to FIGS. 18 and 19, note that when water is present within the tube, the outputs 502, 503 of the integrators 118, 119 deviate significantly more from the reference voltage than when there is water within the tube as shown in traces 402, 403.

Figure 20:
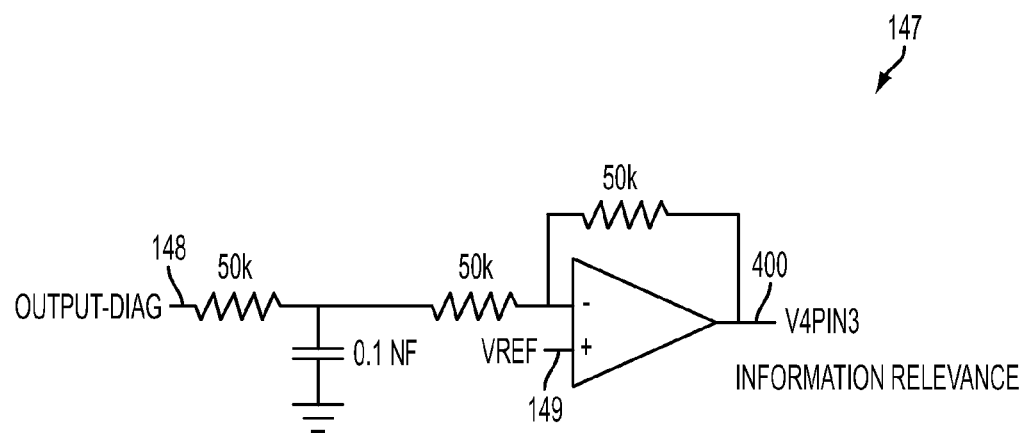
FIG. 20 shows a schematic for providing a compensating reference voltage in accordance with an embodiment of the present disclosure.

FIG. 20 shows a schematic 147 for providing a compensating reference voltage in accordance with an embodiment of the present disclosure. That is, the circuit 147 receives the diagnostic signal 148 from the sample-and-hold circuit 123 which is fed through a connection 148. The output of the circuit 147 may be used as the compensating reference voltage for the op-amps and/or elsewhere within the circuit 113 of FIGS. 13A-15 (or any other embodiment described herein that uses a reference voltage). The circuit 147 adjusts the reference voltage 149 to supply the op-amps with a compensating reference voltage 400 (i.e., the compensating reference voltage) so that the diagnostic signals approach the reference voltage 149. That is, the compensating reference voltage 400 is adjusted to compensate for voltage errors of the op-amps. A second circuit 147 may be used to adjust the op-amps of the quadrature output (e.g., such as the opamp of the second integrator 121) by using the output quadrature diagnostic (e.g., the output of the third sample-and-hold circuit 124 of FIG. 13C).

Figure 21A:
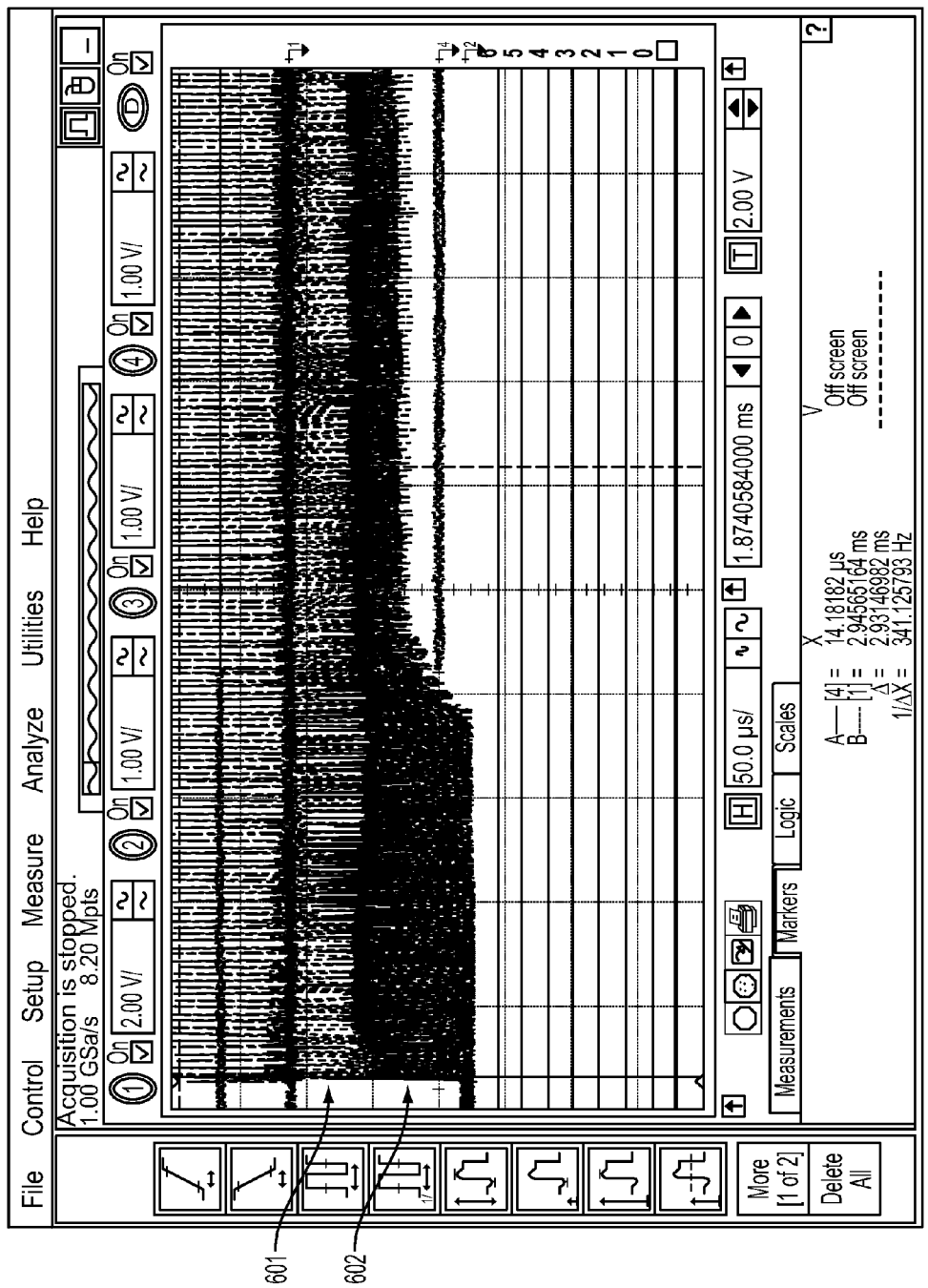
FIGS. 21A and 21B show the operation of the compensating reference voltage in accordance with an embodiment of the present disclosure.
Figure 21B:
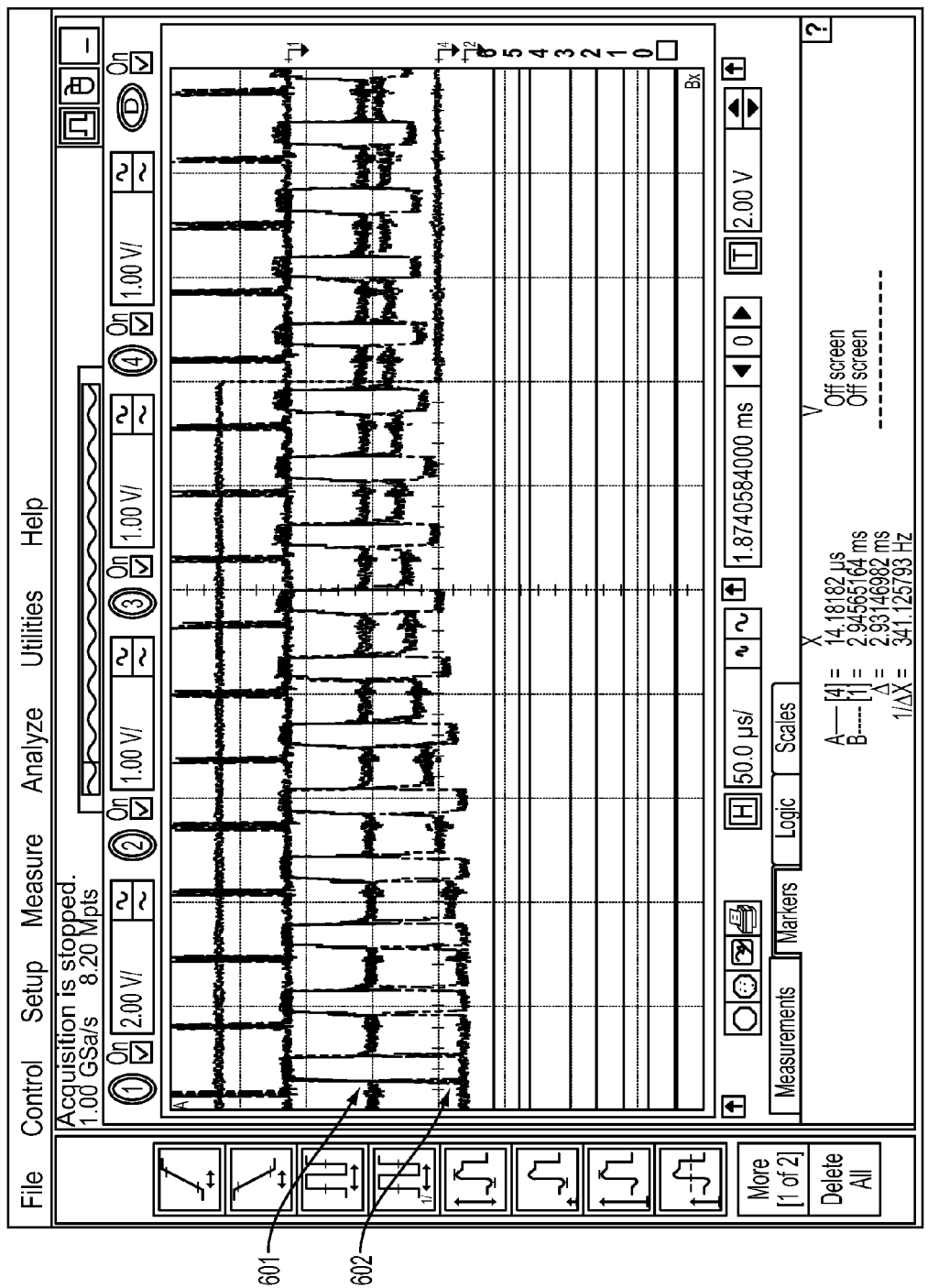

FIGS. 21A and 21B show the operation of the compensating reference voltage 400 starting from power on, demonstrating how the integrator reference voltage 400 converges on the correct value to null out offset errors and provides optimal sensitivity to the signal indicating the presence of water. Signal trace 601 shows the compensating reference voltage from an offset adjusting circuit 151 of FIG. 22B (described below) and signal trace 602 shows the compensating reference voltage from an offset adjusting circuit 152 of FIG. 22B (described below).

FIGS. 22A-23B show a circuit 150 for detecting the presence of air within a tube in accordance with another embodiment of the present disclosure. The circuit 150 includes wires 306 to receive a receiver signal from a receiver, a first amplifier 308 (inverting), a second amplifier 310 (non-inverting), a first switching network 312 that switches in accordance with a first switching signal, a second switching network 314 that switches in accordance with a second switching signal (e.g., a quadrature switching signal), a first integrator 153, a second integrator 154, and first, second, third and fourth sample-and-hold circuits 316, 318, 320, 322. The circuit 150 also includes a CPLD 155.

Figure 13A:
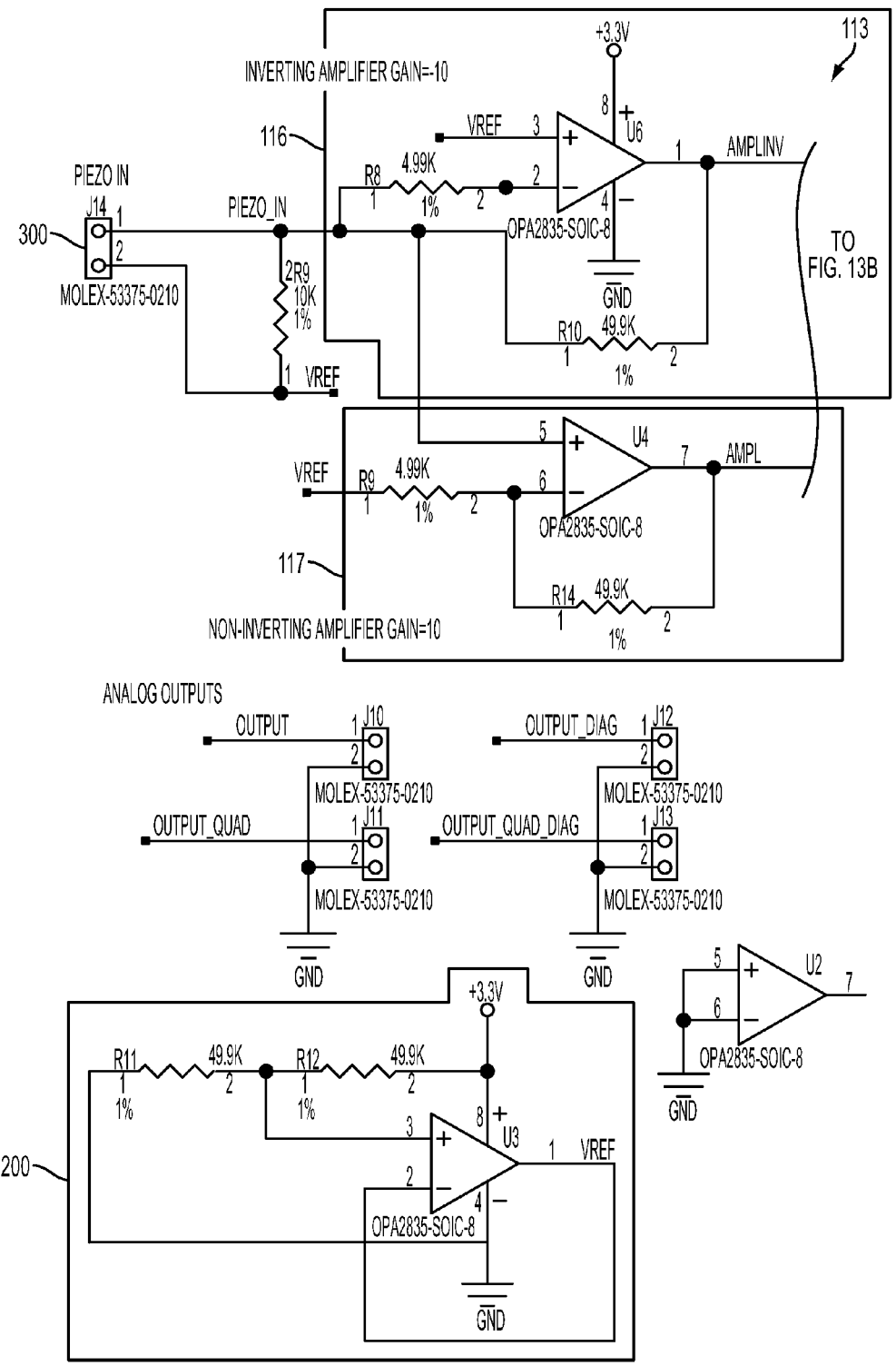
FIGS. 13A-15 illustrate a schematic of a circuit for detecting air in a fluid line using active rectification in accordance with an embodiment of the present disclosure.
Figure 13B:
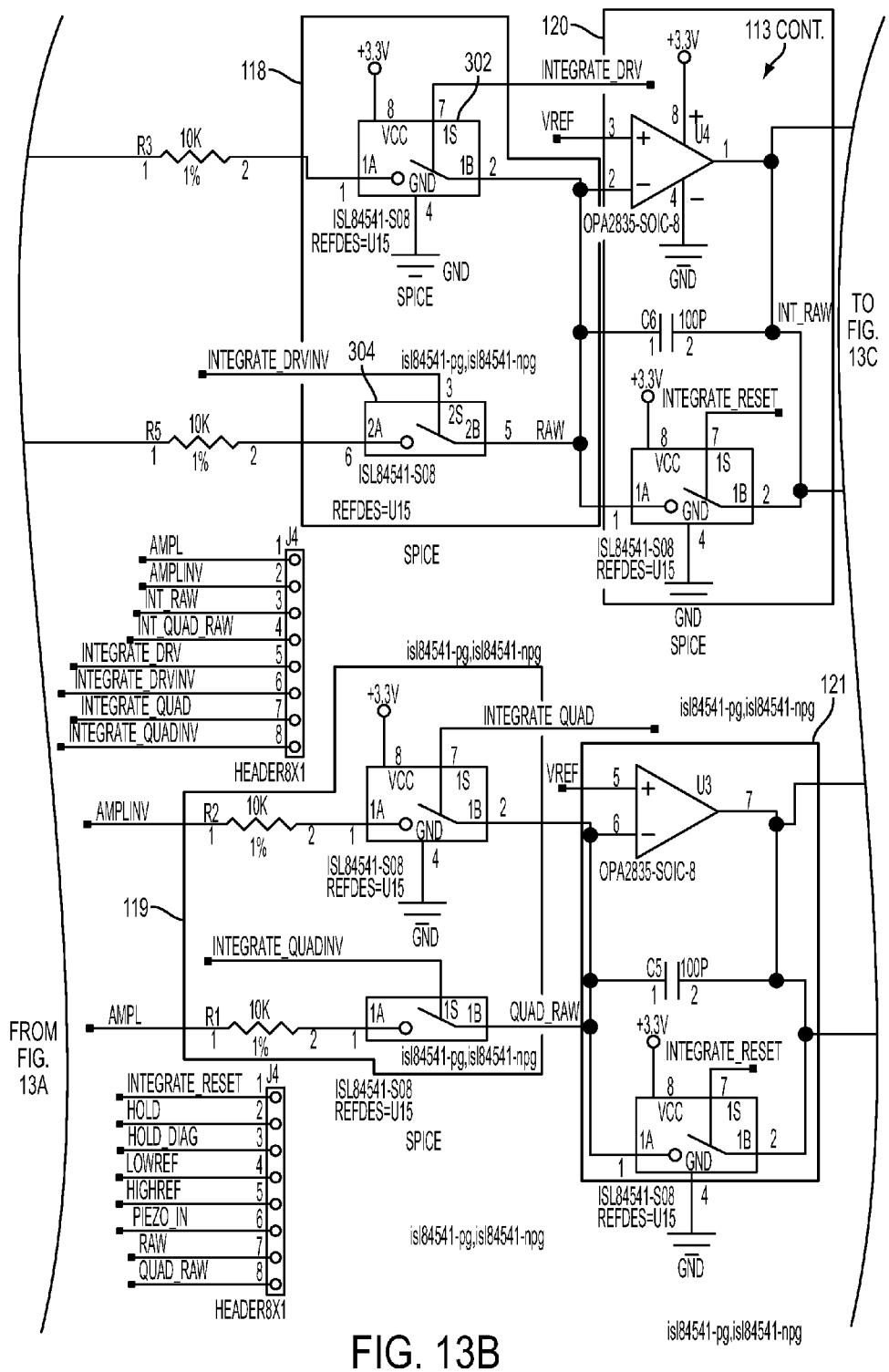
Figure 13C:
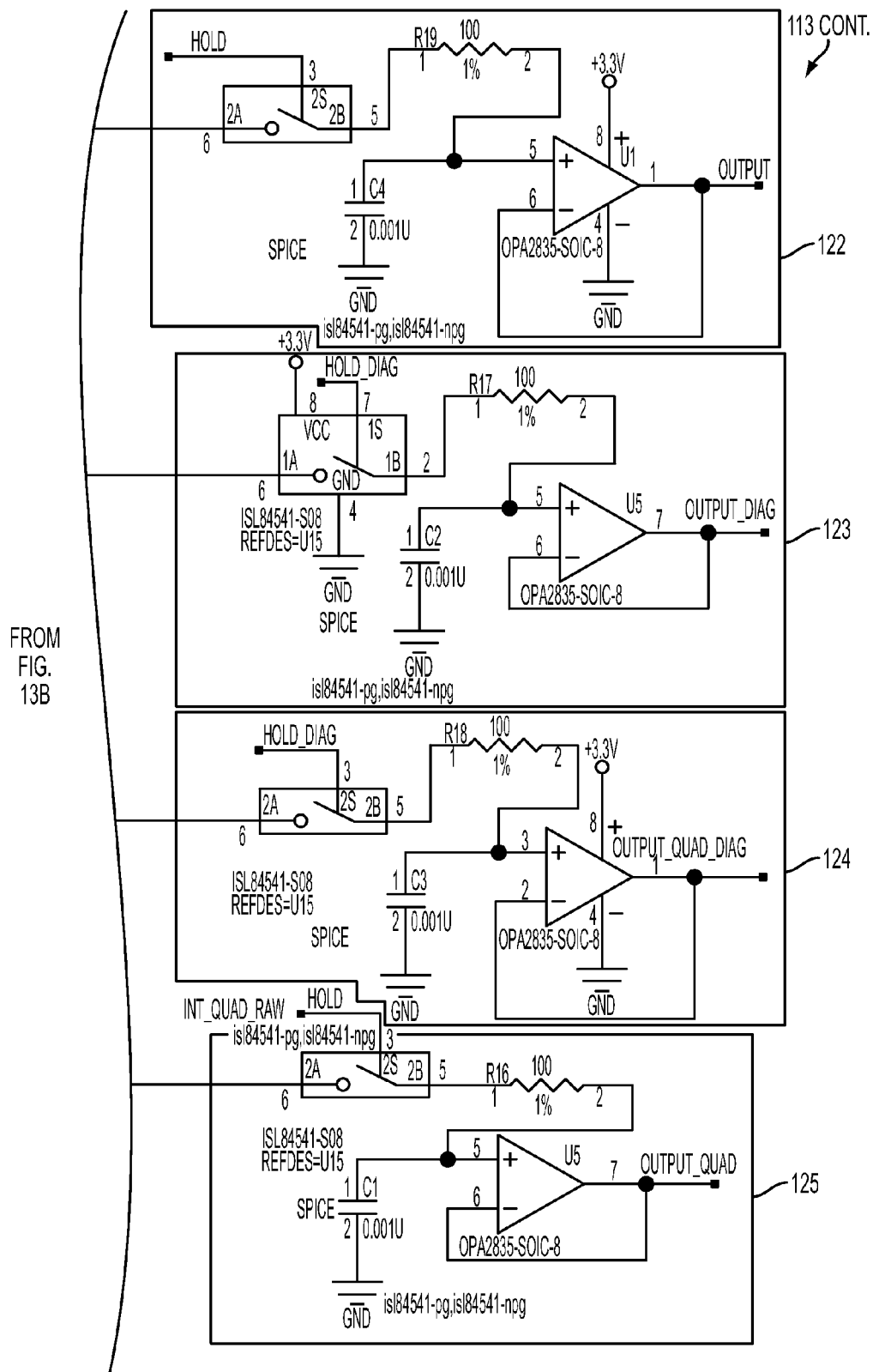
Figure 22A:
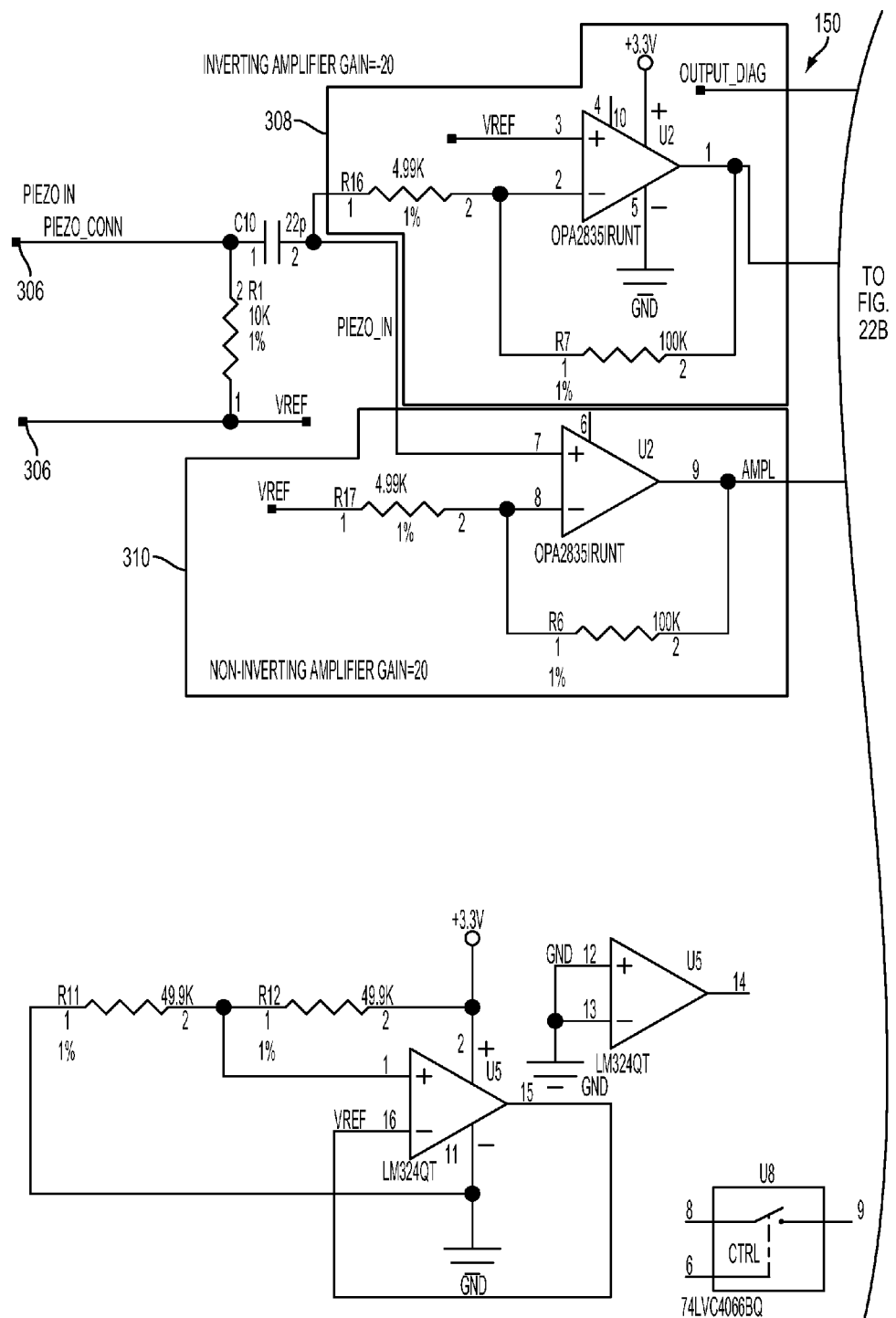
FIGS. 22A-23B show a circuit for detecting the presence of air within a tube in accordance with another embodiment of the present disclosure.
Figure 22B:
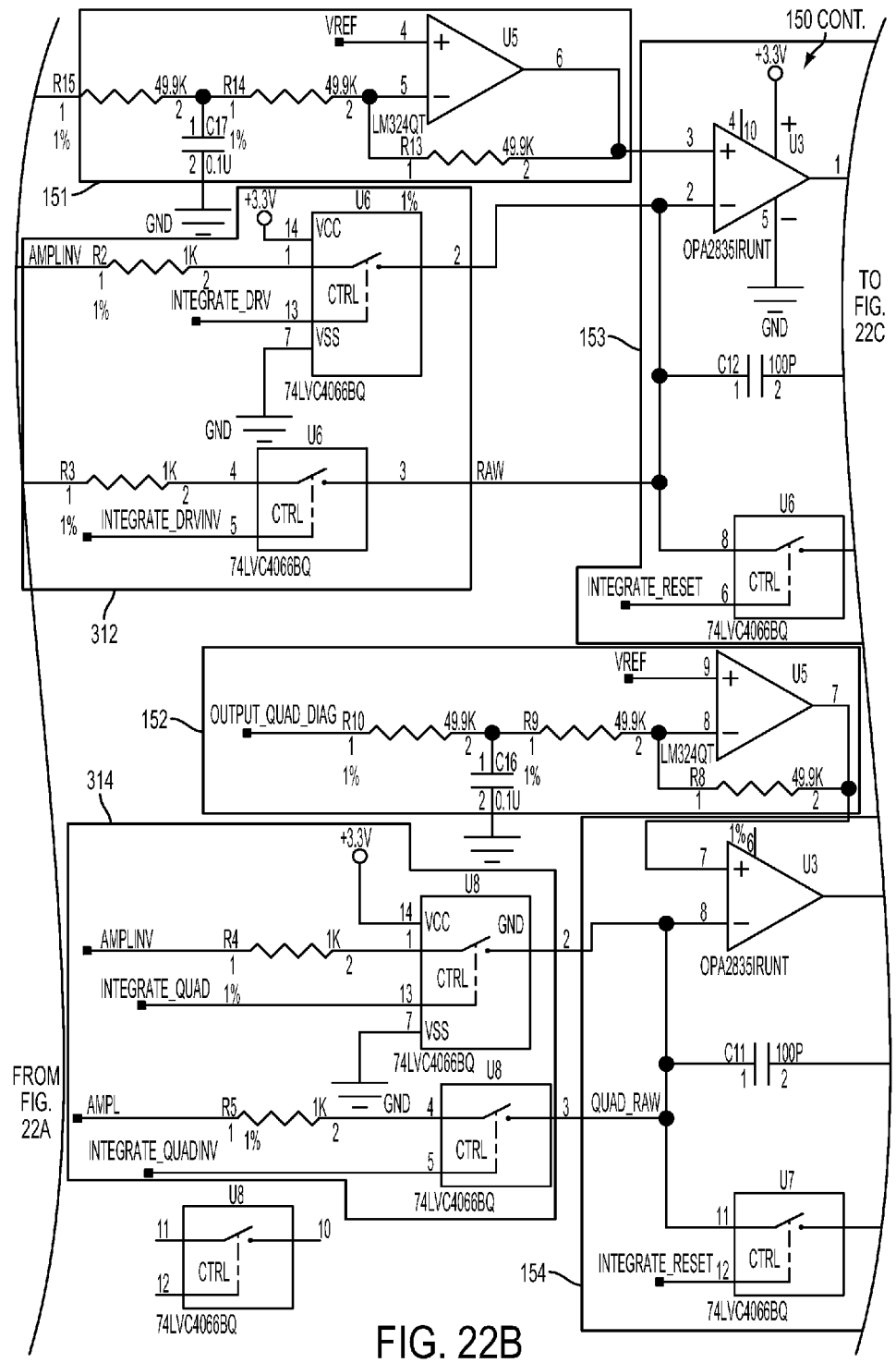
Figure 22C:
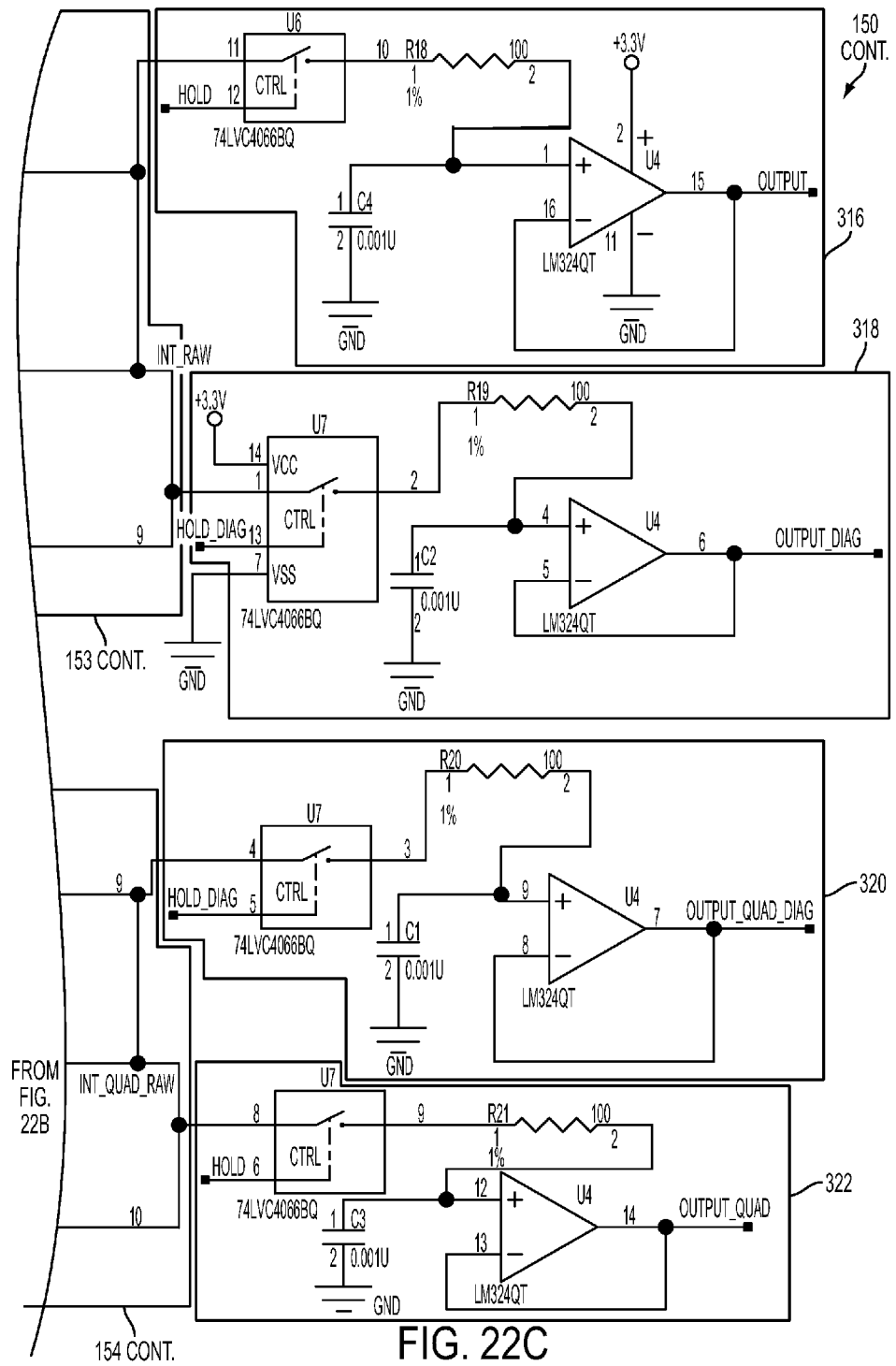
Figure 23A:
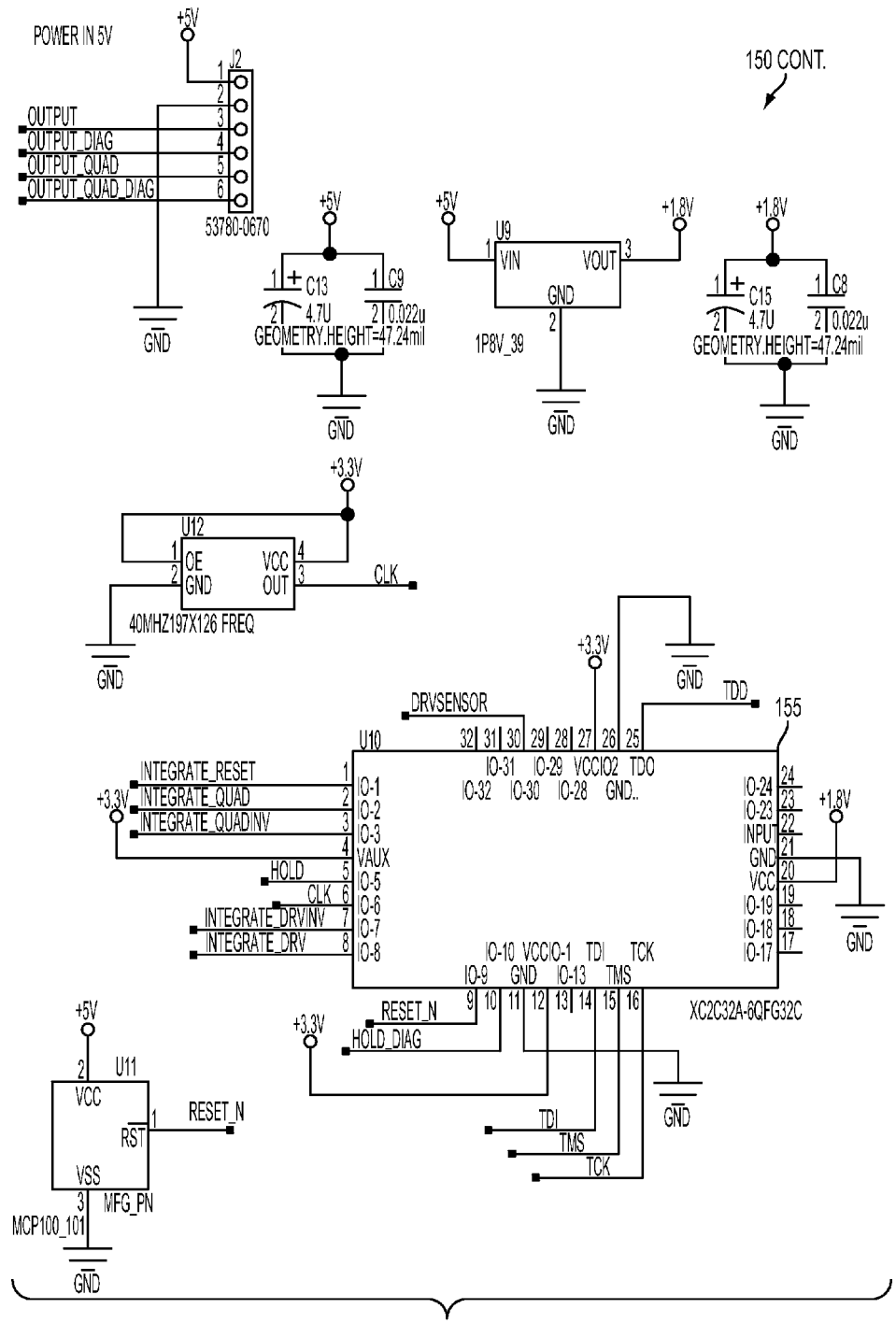
Figure 23B:
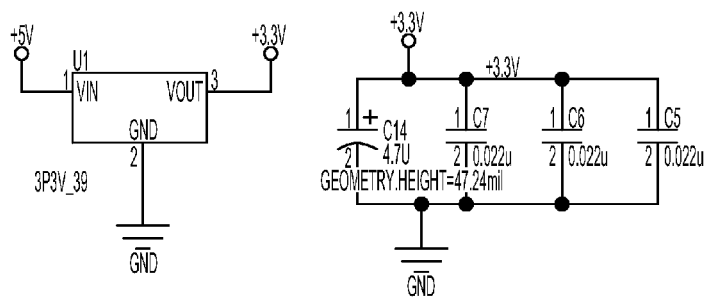
Figure 23B:
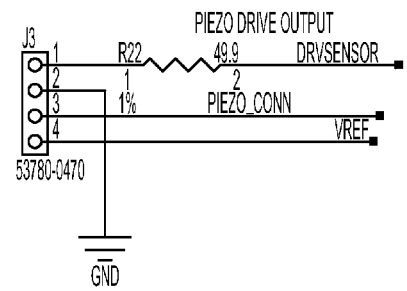
Figure 23B:
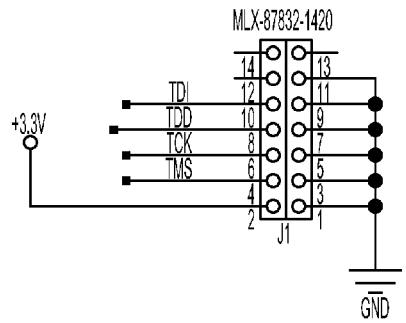
Figure 24A:
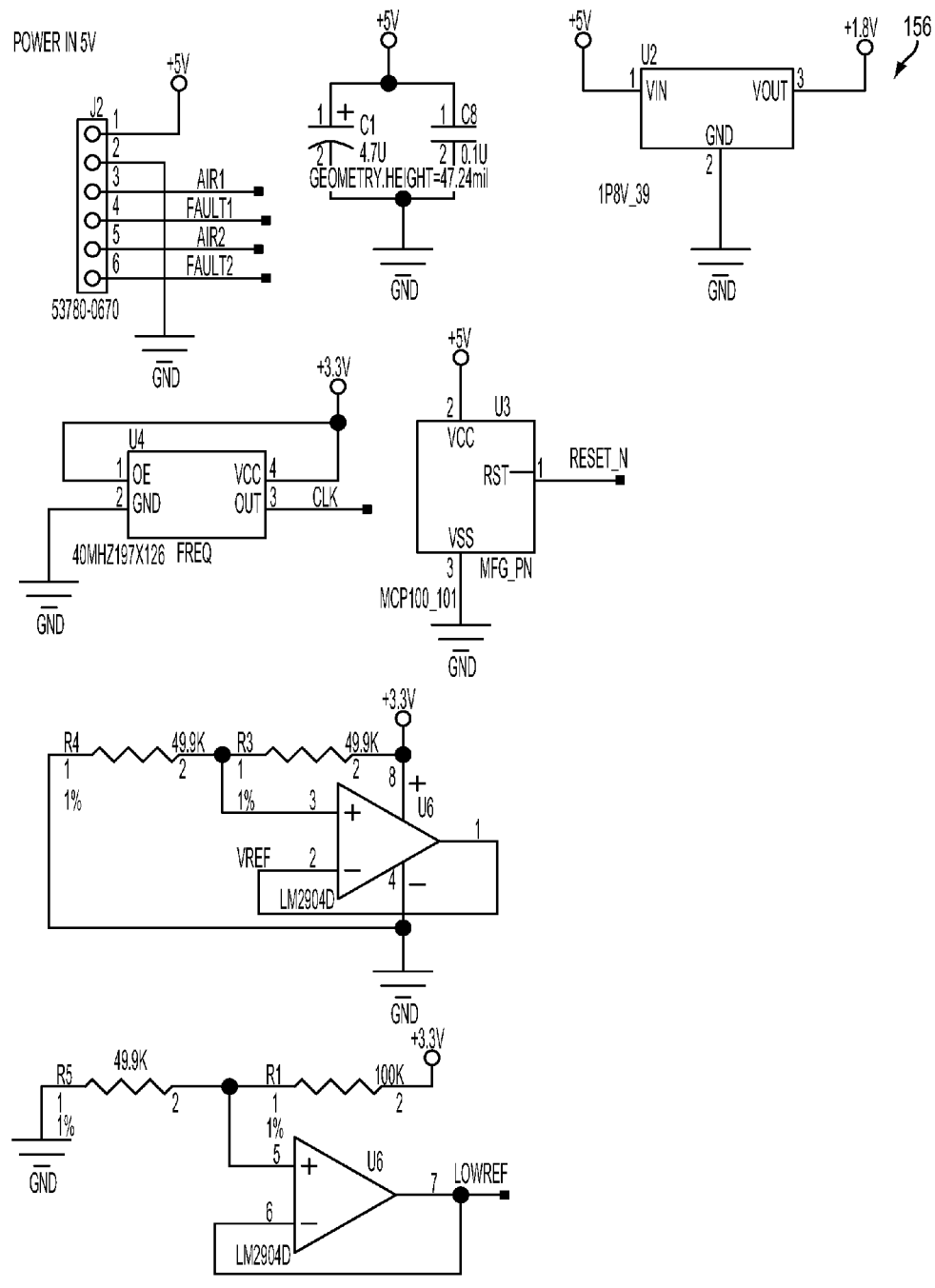
FIGS. 24A-26C show a circuit for detecting the presence of air within two tubes in accordance with another embodiment of the present disclosure.
Figure 24B:
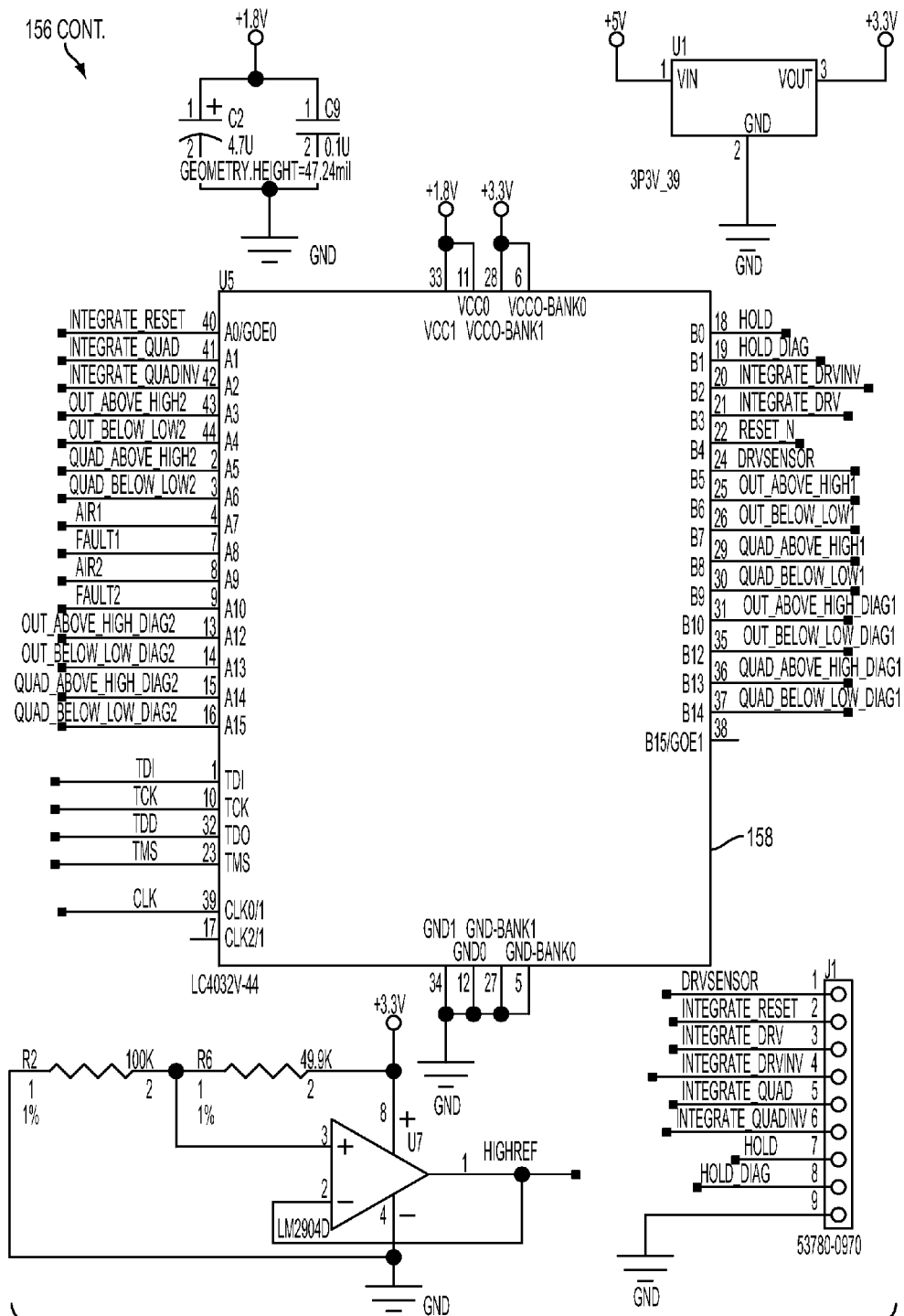
Figure 24C:
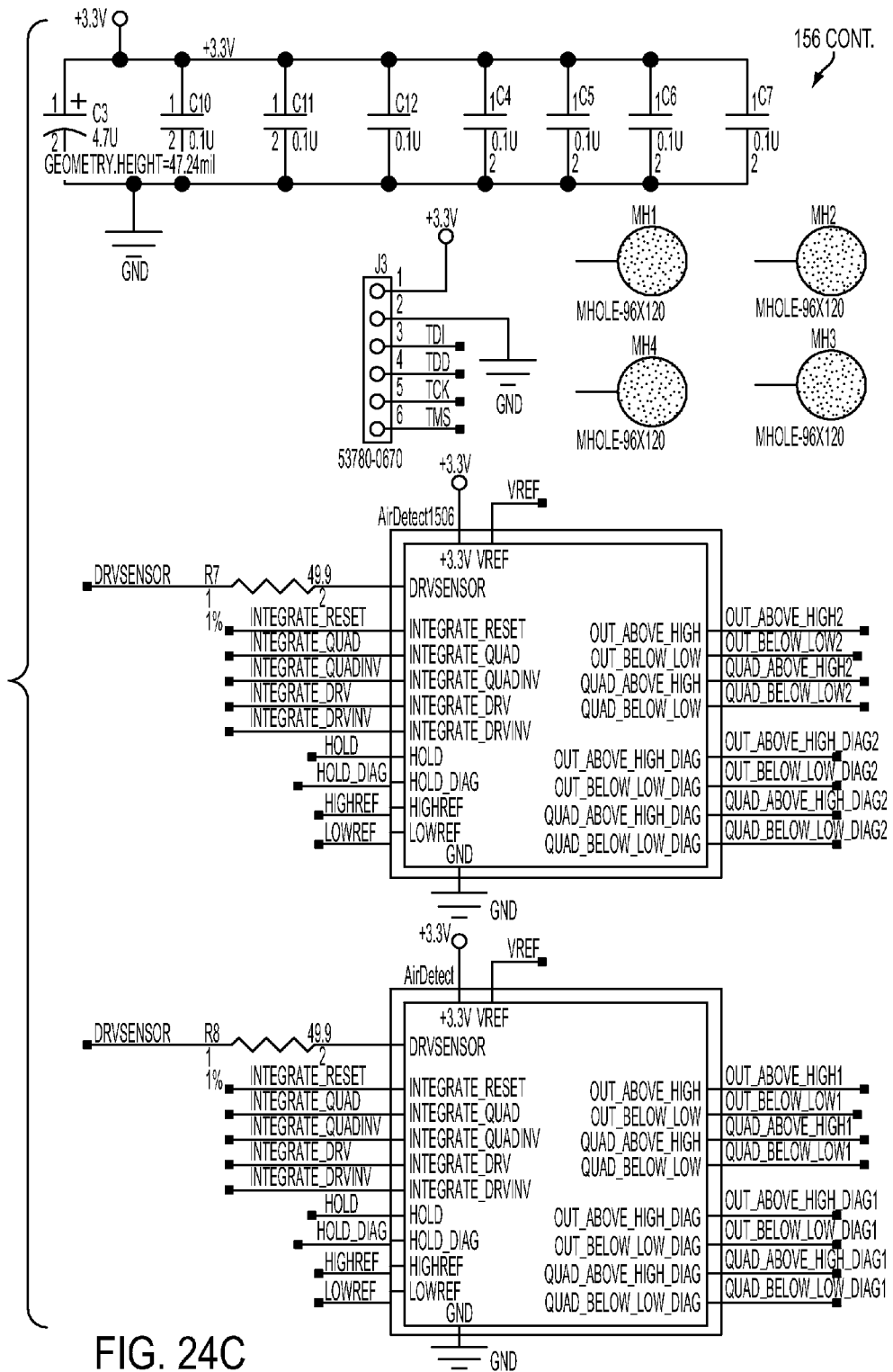
Figure 25A:
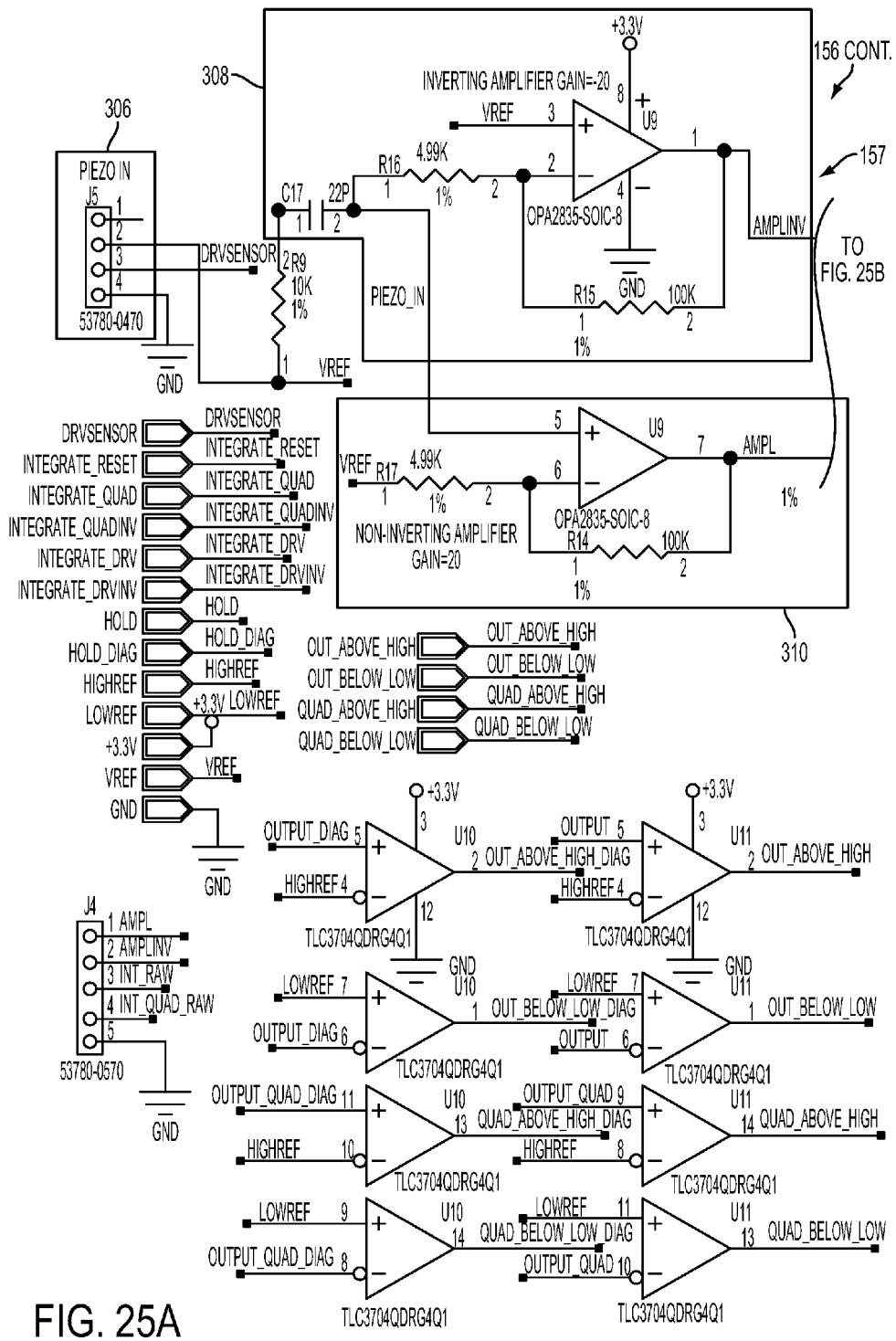
Figure 25B:
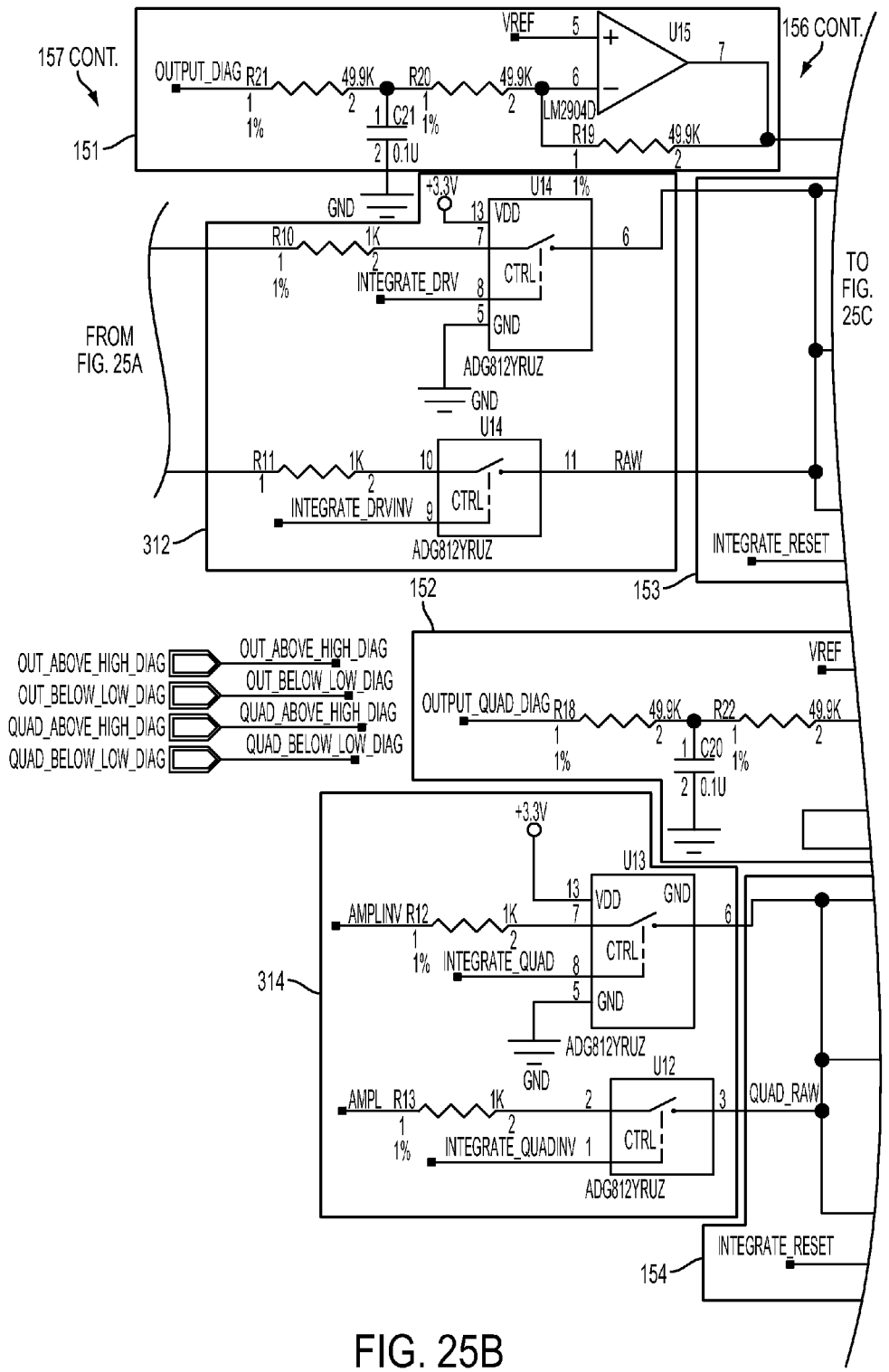
Figure 25C:
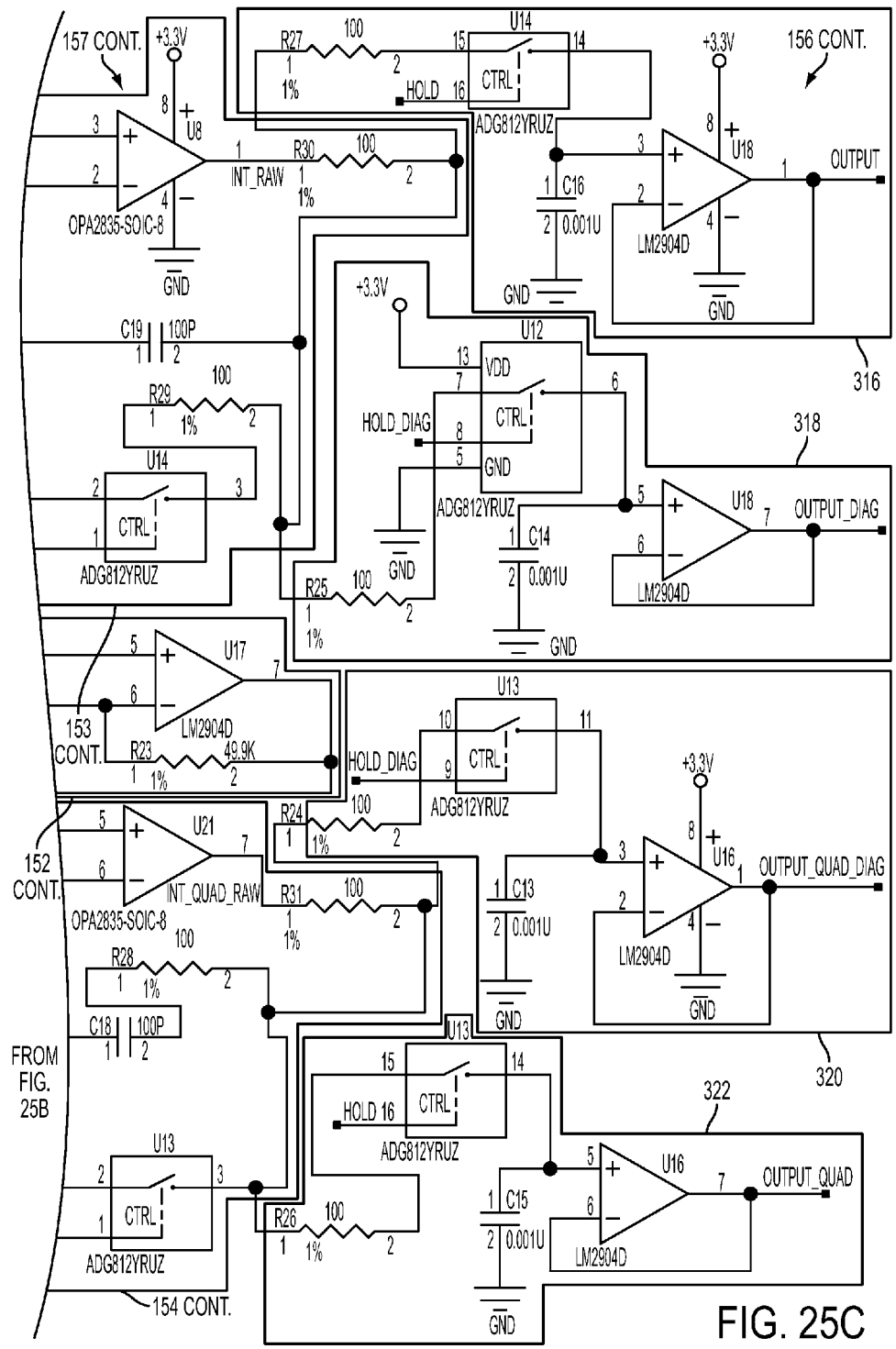
Figure 26A:
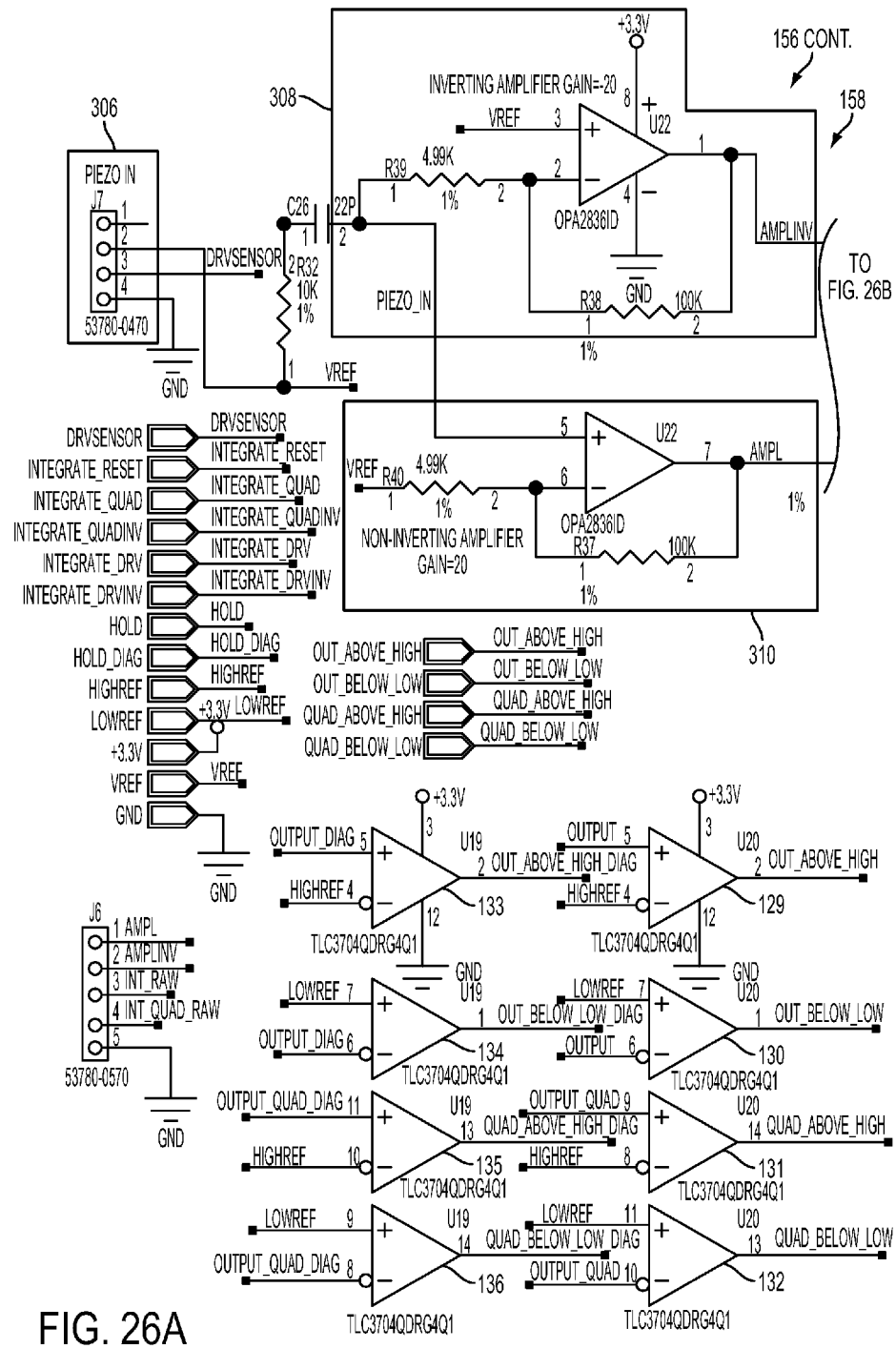
Figure 26B:
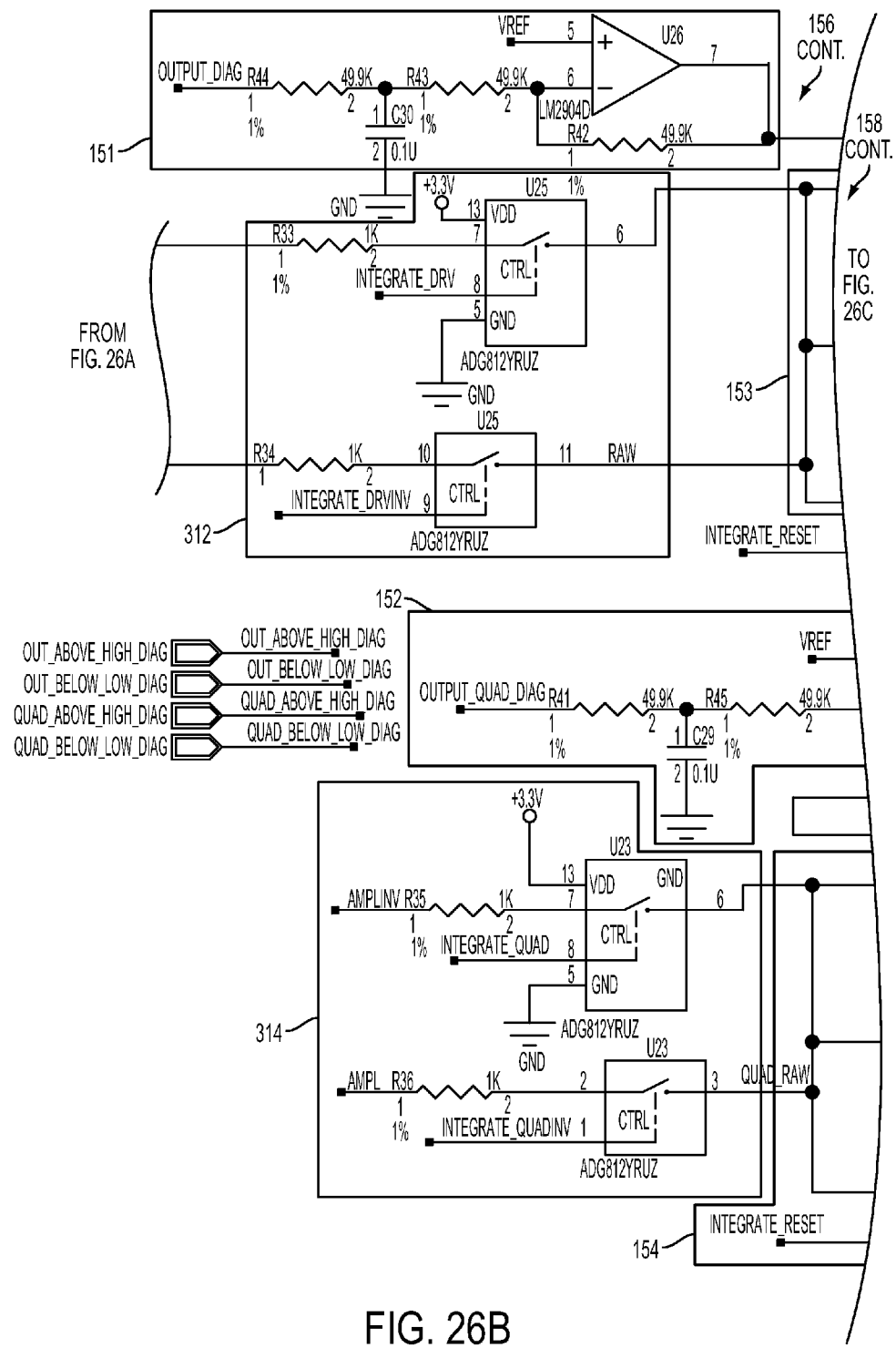
Figure 26C:
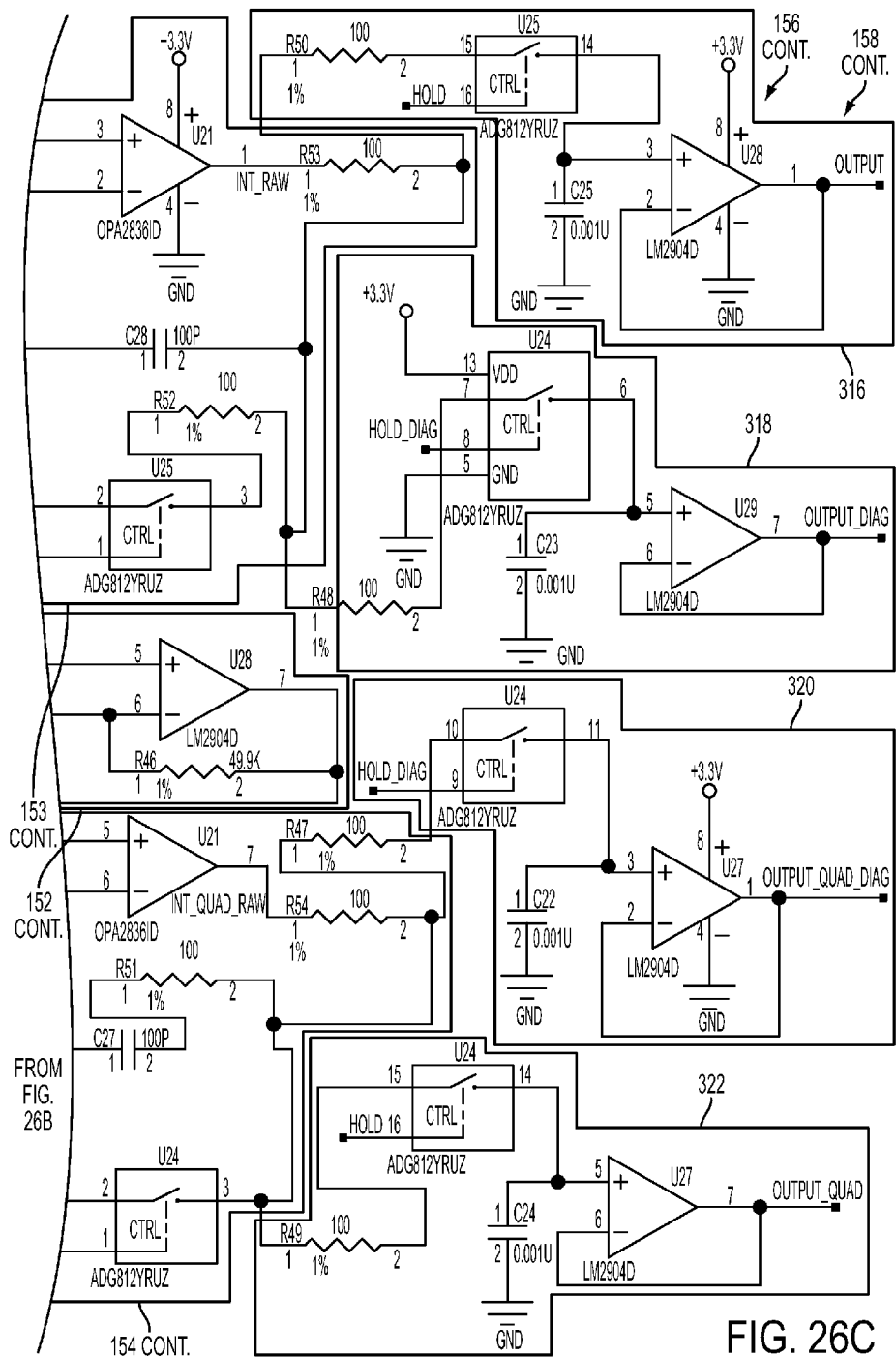

The portion of the circuit 150 shown in FIG. 22A-22C is similar to the circuit 113 shown in FIG. 13; however, the circuit 150 includes an offset adjusting circuit 151 to provide a compensating reference voltage to the first integrator 153, and the circuit 150 also includes another offset adjusting circuit 152 to provide a compensating reference voltage to a second integrator 154. The circuit 151 provides the compensating reference voltage by feeding the output of the sample-and-hold circuit 318 (i.e., the OUTPUT_DIAG signal) thereto. The circuit 152 provides the compensating reference voltage by feeding the output of the sample-and-hold circuit 3120 (i.e., the OUTPUT_QUAD_DIAG) thereto.

The circuit 150 also includes a CPLD 155 to generate the first and second switching signals, control the reset of the first and second integrators 153, 154, control the sample-and-hold circuits 316, 318, 320, 322, receive the outputs of the sample-and-hold circuits 316, 318, 320, 322, and issue an alarm and/or alert based upon any detected air as described herein.

FIGS. 24A-26C show a circuit 156 that can detect air in two tubes. That is, the circuit 156 includes circuitry 157 (see FIGS. 25A-25C) to detect air in a first tube using synchronous rectification. The circuit 156 also includes circuitry 158 (see FIGS. 26A-26C) to detect air in a second tube using synchronous rectification. The operation of the circuit 156 may be controlled by a CPLD 158 shown in FIG. 24B.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or a definite article is used when referring to a singular noun, e.g., "a," "an," or "the," this includes a plural of that noun unless something otherwise is specifically stated or the context clearly indicates otherwise. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and are not necessarily for describing a sequential or chronological order. Likewise, these terms are not for indicating an order of importance or relative criticality of the referred-to elements. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A system for detecting air, the system comprising:
a transmitter configured to transduce a driver signal to ultrasonic vibrations;
a receiver configured to receive the ultrasonic vibrations and transduce the ultrasonic vibrations to provide a receiver signal;
an air-detection circuit in operative communication with the receiver to process the receiver signal to generate a processed signal corresponding to detected air, the air-detection circuit comprising at least one active-rectifying element configured to actively rectify the receiver signal to provide the processed signal;
a first conductive path to provide a first polarity of the receiver signal from the receiver;
a second conductive path to provide a second polarity of the receiver signal from the receiver;
a first switch electrically coupled to the first and second conductive paths, the first switch configured to switch a first switch output to between the first and second polarities of the receiver signal, the first switch defining the at least one active-rectifying element;
a second switch electrically coupled to the first and second conductive paths, the second switch configured to switch a second switch output to between the first and second polarities of the receiver signal;
a first amplifier having a positive input and a negative input, wherein the positive input is coupled to the first switch output and the negative input is coupled to the second switch output, wherein the first amplifier provides a first amplifier output in accordance with the positive and negative inputs; and
a first filter electrically coupled to the first amplifier output of the first amplifier to provide a first filter output.

2. The system according to claim 1, wherein the transmitter and receiver are configured to pass the ultrasonic vibrations through a tube such that the processed signal corresponds to detected air within the tube.

3. The system according to claim 2, wherein the tube is a medical tube.

4. The system according to claim 2, wherein the tube is an intravenous fluid tube.

5. The system according to claim 2, wherein the tube carries blood.

6. The system according to claim 1, wherein the system is configured to be part of an infusion pump.

7. The system according to claim 1, wherein the system is configured to be part of a dialysis apparatus.

8. The system according to claim 1, wherein the air-detection circuit is configured to detect a bubble.

9. The system according to claim 1, wherein the air-detection circuit compares the processed signal to a predetermined threshold to determine if a bubble exists within a tube.

10. The system according to claim 1, the system further comprising an amplifier.

11. The system according to claim 10, wherein the amplifier amplifies the receiver signal.

12. The system according to claim 10, wherein the amplifier amplifies the processed signal.

13. The system according to claim 1, wherein at least one of the receiver signal and the processed signal is a digital signal embodied in a digital circuit.

14. The system according to claim 1, wherein at least one of the receiver signal and the processed signal is an analog signal.

15. The system according to claim 1, further comprising a sample-and-hold circuit configured to sample the processed signal to hold the processed signal for at least a predetermined amount of time.

16. The system according to claim 1, wherein the transmitter and receiver are configured to pass the ultrasonic vibrations through a tube such that the processed signal corresponds to detected air within the tube, wherein the air-detection circuit is configured to calculate a total amount of air that passes through the tube utilizing a flow rate of fluid through the tube and the processed signal.

17. The system according to claim 1, wherein at least one of the receiver signal, the processed signal, the first amplifier output, and a first filter output is a digital signal embodied in a digital circuit.

18. The system according to claim 1, wherein at least one of the receiver signal, the processed signal, the first amplifier output, and a first filter output is an analog signal.

19. The system according to claim 1, wherein the first filter is an integrator.

20. The system according to claim 19, wherein the integrator is reset after a predetermined period of integration time.

21. The system according to claim 1, wherein the first filter is a low-pass filter.

22. The system according to claim 1, wherein at least one of the first and second switches are electronically controlled.

23. The system according to claim 1, wherein the first and second switches are configured to receive a switching signal, wherein the switching signal and the first and second switches are configured to switch a polarity of the electrical coupling between the first amplifier and the receiver in accordance with the switching signal.

24. The system according to claim 1, wherein:
the first and second switches are configured to receive a switching signal,
the first and second switches switch such that the first switch output is coupled to the first polarity of the receiver signal about when the second switch output is coupled to the second polarity,
the first and second switches switch such that the first switch output is coupled to the second polarity of the receiver signal about when the second switch output is coupled to the first polarity, and
the first and second switches switch in response to the switching signal.

25. A method of detecting air, the method comprising:
transmitting ultrasonic energy;
receiving the ultrasonic energy;
transducing, using a circuit, the received ultrasonic energy into a receiver signal;
actively rectifying, using the circuit, the receiver signal to provide a processed signal; and
determining whether the processed signal is less that a predetermined threshold, wherein the circuit comprises:
a first conductive path to provide a first polarity of the receiver signal from a receiver,
a second conductive path to provide a second polarity of the receiver signal from the receiver,
a first switch electrically coupled to the first and second conductive paths, the first switch configured to switch a first switch output to between the first and second polarities of the receiver signal, the first switch defining the at least one active-rectifying element,
a second switch electrically coupled to the first and second conductive paths, the second switch configured to switch a second switch output to between the first and second polarities of the receiver signal,
a first amplifier having a positive input and a negative input, wherein the positive input is coupled to the first switch output and the negative input is coupled to the second switch output, wherein the first amplifier provides a first amplifier output in accordance with the positive and negative inputs, and a first filter electrically coupled to the first amplifier output of the first amplifier to provide a first filter output.

26. The method according to claim 25, wherein the act of actively rectifying the receiver signal to provide the processed signal is synchronously rectifying the receiver signal to provide the processed signal.

27. A circuit comprising:
a receiver connection configured to provide a receiver signal;
an air-detection circuit in operative communication with the receiver connection to process the receiver signal to generate a processed signal corresponding to detected air, the air-detection circuit comprising at least one active-rectifying element configured to actively rectify the receiver signal to provide the processed signal;
a first conductive path to provide a first polarity of the receiver signal from the receiver;
a second conductive path to provide a second polarity of the receiver signal from the receiver;
a first switch electrically coupled to the first and second conductive paths, the first switch configured to switch a first switch output to between the first and second polarities of the receiver signal, the first switch defining the at least one active-rectifying element;
a second switch electrically coupled to the first and second conductive paths, the second switch configured to switch a second switch output to between the first and second polarities of the receiver signal;
a first amplifier having a positive input and a negative input, wherein the positive input is coupled to the first switch output and the negative input is coupled to the second switch output, wherein the first amplifier provides a first amplifier output in accordance with the positive and negative inputs; and
a first filter electrically coupled to the first amplifier output of the first amplifier to provide a first filter output.

28. The circuit according to claim 27, wherein the air-detection circuit compares the processed signal to a predetermined threshold to determine if a bubble exists within a tube.

* * * * *